(12) United States Patent
Srivastava et al.

(10) Patent No.: US 9,206,481 B2
(45) Date of Patent: Dec. 8, 2015

(54) PROSTATE CANCER-SPECIFIC ALTERATIONS IN ERG GENE EXPRESSION AND DETECTION AND TREATMENT METHODS BASED ON THOSE ALTERATIONS

(75) Inventors: Shiv Srivastava, Potomac, MD (US); Albert Dobi, Columbia, MD (US); Taduru Sreenath, Germantown, MD (US); Gyorgy Petrovics, Bethesda, MD (US); Chen Sun, Bethesda, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 555 days.

(21) Appl. No.: 12/081,101

(22) Filed: Apr. 10, 2008

(65) Prior Publication Data
US 2008/0269157 A1 Oct. 30, 2008

Related U.S. Application Data

(63) Continuation-in-part of application No. PCT/US2007/080826, filed on Oct. 9, 2007.

(60) Provisional application No. 60/929,505, filed on Jun. 29, 2007, provisional application No. 60/850,254, filed on Oct. 10, 2006.

(51) Int. Cl.
*C12Q 1/68* (2006.01)

(52) U.S. Cl.
CPC ........ *C12Q 1/6886* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,830,645 A * | 11/1998 | Pinkel et al. | 435/6.11 |
| 6,790,619 B2 | 9/2004 | Meissner et al. | |
| 7,374,927 B2 | 5/2008 | Palma et al. | |
| 2002/0182586 A1* | 12/2002 | Morris et al. | 435/4 |
| 2004/0241707 A1* | 12/2004 | Gao et al. | 435/6 |
| 2005/0031623 A1 | 2/2005 | Pastorek et al. | |
| 2005/0202428 A1 | 9/2005 | Andrews et al. | |
| 2005/0272080 A1 | 12/2005 | Palma et al. | |
| 2007/0048738 A1 | 3/2007 | Donkena et al. | |
| 2007/0050146 A1 | 3/2007 | Bentwich et al. | |
| 2007/0212702 A1 | 9/2007 | Tomlins et al. | |
| 2008/0038743 A1 | 2/2008 | Gocke et al. | |

FOREIGN PATENT DOCUMENTS

| | | |
|---|---|---|
| JP | 2007-535939 | 12/2007 |
| WO | 0129262 A2 | 4/2001 |
| WO | 0210449 A2 | 2/2002 |
| WO | WO 02/10449 A | 2/2002 |
| WO | WO 03/073826 A | 9/2003 |
| WO | 2004048511 A2 | 6/2004 |
| WO | 2005/113816 | 12/2005 |
| WO | WO 2005/113816 A2 | 12/2005 |
| WO | 2007/033187 | 3/2007 |
| WO | WO 2008/063769 A | 5/2008 |

OTHER PUBLICATIONS

Benner et al (Trends in Genetics (2001).*
Cobb et al (Crit Care Med 2002 vol. 30 p. 2711).*
Petrovics et al. (Oncogene 2005 vol. 24 p. 3847).*
Owczarek et al. (Gene 2004 vol. 324 p. 65).*
Enard et al. (Science 2002 vol. 296 p. 340).*
Gala et al. (Ann Hematol 1994 vol. 69 p. 17).*
Pusztai and Hess, Annals of Oncology, vol. 15, pp. 1731-1737, 2004.*
Golub et al (Science, vol. 286, pp. 531-537, Oct. 1999).*
PCT/US2007/08026, International Search Report and Written Opinion of the International Searching Authority (Oct. 30, 2008).
PCT/US2008/004580, Communication Relating to the Results of the Partial International Search (Dec. 8, 2008).
PCT US2008/004580, International Search Report and Written Opinion (Feb. 26, 2009).
European Patent Office Communication from European Patent Application No. 08 742 682.1 dated Jan. 29, 2013, 7 Pages.
Hu, Ying et al., Delineation of TMPRSS2-ERG Splice Variants in Prostate Cancer, Clinical Cancer Research, 2008, vol. 14, No. 15, Aug. 1, 2008, pp. 4719-1725.
Communication Pursuant to Article 94(3) EPC from the European Patent Office for European Patent Application No. 07 868 397.6 dated Sep. 13, 2012, pp. 1-6.
Communication from European Patent Office for European Patent Application No. 12163605.4 dated Sep. 21, 2012, 9 Pages.
Ueki, A. et al., Intramolecular epitope spreading among anti-caspase-8 autoantibodies in patients with silicosis, systemic sclerosis and systemic lupus erythematosus, as well as in healthy individuals, Clinical and Experimental Ummunology, Sep. 1, 2002, pp. 556-561, XP-002374605.
Wang, J. et al., Expression of Variant TMPRSS2/ERG Fusion Messenger RNAs is Associated with Aggressive Prostate Cancer, Cancer Research, vol. 66, No. 17, Sep. 1, 2006, pp. 8347-8351.
Perner, S. et al., TMPRSS2:ERG Fusion-Associated Deletions Provide Insight into the Heterogeneity of Prostate Cancer, Cancer Research, vol. 66, No. 17, Sep. 1, 2006, pp. 8337-8341.
Shand, Randi L. et al., Molecular biology of prostate-cancer pathogenesis, Current Opinion in Urology, vol. 16, No. 3, May 1, 2006, pp. 123-131.

(Continued)

*Primary Examiner* — Katherine Salmon
(74) *Attorney, Agent, or Firm* — MH2 Technology Law Group, LLP

(57) ABSTRACT

Alterations in ERG gene expression can be observed in patients with prostate cancer. Specific ERG isoforms are associated with, or involved in, prostate cancer. Compositions comprising these isoforms provide therapeutic benefit and can be used in methods of detecting, diagnosing, prognosing, and treating prostate cancer. These compositions provide biomarkers for detecting the expression of combinations of the PSA/KLK3, PMEPA1, NKX3.1, ODC1, AMD1, and ERG genes.

5 Claims, 33 Drawing Sheets

(56) References Cited

OTHER PUBLICATIONS

XP-002682957, Oligonucleotide SEQ ID No. 34952 for detecting SNP TSC0011099, Feb. 20, 2002.
XP-002682891, Sequence 14907 from Patent WO0157274, Jan. 21, 2004.
Rinehart, Clifford A., Aging and Cancer: The Role of Stromal Interactions With Epithelial Cells, Molecular Carcinogenesis, 18:187-192 (1997).
Tsay, Yim H. et al., Cloning and Characterization of ERG8, an Essential Gene of Saccharomyces cerevisiae That Encodes Phosphomevalonate Kinase, Molecular and Cellular Biology, Feb. 1991, pp. 620-631.
Zhu, Fleming et al., Screening of Novel Epilepsy-Related Genes and Isolation and Identification of oDNAs, Journal of Tongji Medical University, 2000, vol. 20, pp. 10-12.
Patent Examination Report dated Nov. 8, 2013 from Australian Patent Application No. 2008354371, pp. 1-5.
GenBank Accession AP001426, Jan. 26, 2001, pp. 1-20.
Communication dated Jan. 6, 2014 from European Patent Application No. 08 742 682.1, pp. 1-5.
Srivastava, Shiv. Structure and Function of the Splice Variants of TMPRSS2-ERG, a Prevalent Genomic Alteration in Prostate Cancer. www.dtic.mil., Sep. 2012, pp. 1-32.
Jhavar, Sameer et al. Detection of TMPRSS2-ERG Translocations in Human Prostate Cancer by Expression Profiling Using GeneChip Human Exon 1.0 ST Arrays. Journal of Molecular Diagnostics, Jan. 2008, vol. 10, No. 1, pp. 50-57.
Clark, J. et al. Diversity of TMPRSS2-ERG fusion trasncripts in the human prostate. Oncogene, 2007, vol. 26, pp. 2667-2673.
Tu, Jiangling J, et al. Gene fusions between TMPRSS2 and ETS family genes in prostate cancer. frequency and transcript variant analysis by RT-PCR and FISH on paraffin-embedded tissues. Modern Pathology, 2007, vol. 20, pp. 921-928.
Communication dated Sep. 12, 2013 from European Patent Application No. 07868397.6 filed Oct. 9, 2007, pp. 1-7.
Sun, C. et al. IMPRSS2-ERG fusion, a common genomic alteration in prostate cancer activates C-MYC and abrogates prostate epithelial differentiation. Oncogene, 2008, vol. 27, pp. 5348-5353.
English Translation of Office Action dated May 7, 2013 from Japanese Patent Application No. 2011-503948, pp. 1-5.
Office Action dated Apr. 30, 2014 from Canadian Patent Application No. 2,719,172, pp. 1-4.
C.M. Owczarek et al., "Detailed mapping of the ERG-ETS2 interval of human chromosome 21 and comparison with the region of conserved synteny on mouse chromosome 16," *Gene* 324:65-77 (2004).
G. Petrovics et al., "Frequent overexpression of ETS-related gene-1 (ERG1) in prostate cancer transcriptome," *Oncogene* 24:3847-3852 (2005).
S.A. Tomlins et al., "Recurrent Fusion of TMPRSS2 and ETS transcription factor genes in prostate cancer," *Science* 310:644-648 (Oct. 28, 2005).
Genebank Online Database. Accession No. AY204742.
PCT/US2007/08026, Partial International Search Report.

\* cited by examiner

```
CCCCCGAGGG ACATGAGAGA AGAGGAGCGG CGCTCAGGTT ATTCCAGGAT  50  AY204742  (SEQ ID NO: 62)

CTTTGGAGAC CCGAGGAAAG CCGTGTTGAC CAAAAGCAAG ACAAATGACT 100  AY204742  (SEQ ID NO: 62)

CACAGAGAAA AAAGATGGCA GAACCAAGGG CAACTAAAGC CGTCAGGTTC 150  AY204742  (SEQ ID NO: 62)

TAGGCGCGAG CTAAGCAGGA GGCGGAGGCG GAGGCGGAGG GCGAGGGGCG  50  ERG8      (SEQ ID NO: 30)
TGAACAGCTG GTAGATGGGC TGGCTTACTG AAGGACATGA TTCAGACTGT 200  AY204742  (SEQ ID NO: 62)

GGGAGCGCCG CCTGGAGCGC GGCAGGAAGC CTTATCAGTT GTGAGTGAGG 100  ERG8      (SEQ ID NO: 30)
CCCGGACCCA GCAGCTTCATA TCAAGGAAGC CTTATCAGTT GTGAGTGAGG 250  AY204742  (SEQ ID NO: 62)

ACCAGTCGTT GTTTGAGTGT GCCTACGGAA CGCCACACCT GGCTAAGACA 150  ERG8      (SEQ ID NO: 30)
ACCAGTCGTT GTTTGAGTGT GCCTACGGAA CGCCACACCT GGCTAAGACA 300  AY204742  (SEQ ID NO: 62)

GAGATGACCG CGTCCTCCTC CAGCGACTAT GGACAGACTT CCAAGATGAG 200  ERG8      (SEQ ID NO: 30)
GAGATGACCG CGTCCTCCTC CAGCGACTAT GGACAGACTT CCAAGATGAG 350  AY204742  (SEQ ID NO: 62)

CCCACGCGTC CCTCAGCAGG ATTGGCTGTC TCAACCCCCA GCCAGGGTCA 250  ERG8      (SEQ ID NO: 30)
CCCACGCGTC CCTCAGCAGG ATTGGCTGTC TCAACCCCCA GCCAGGGTCA 400  AY204742  (SEQ ID NO: 62)

CCATCAAAAT GGAATGTAAC CCTAGCCAGG TGAATGGCTC AAGGAACTCT 300  ERG8      (SEQ ID NO: 30)
CCATCAAAAT GGAATGTAAC CCTAGCCAGG TGAATGGCTC AAGGAACTCT 450  AY204742  (SEQ ID NO: 62)
```

Figure 1A

```
CCTGATGAAT GCAGTGTGGC CAAAGGCGGG AAGATGGTGG GCAGCCCAGA  350    ERG8     (SEQ ID NO: 30)
CCTGATGAAT GCAGTGTGGC CAAAGGCGGG AAGATGGTGG GCAGCCCAGA  500    AY204742 (SEQ ID NO: 62)
..........

CACCGTTGGG ATGAACTACG GCAGCTACAT GGAGGAGAAG CACATGCCAC  400    ERG8     (SEQ ID NO: 30)
CACCGTTGGG ATGAACTACG GCAGCTACAT GGAGGAGAAG CACATGCCAC  550    AY204742 (SEQ ID NO: 62)
..........

CCCCAAACAT GACCACGAAC GAGCGCAGAG TTATCGTGCC AGCAGATCCT  450    ERG8     (SEQ ID NO: 30)
CCCCAAACAT GACCACGAAC GAGCGCAGAG TTATCGTGCC AGCAGATCCT  600    AY204742 (SEQ ID NO: 62)
..........

ACGGTATGGA GTACAGACCA TGTGCGGCAG TGGCTGGAGT GGGCGGTGAA  500    ERG8     (SEQ ID NO: 30)
ACGGTATGGA GTACAGACCA TGTGCGGCAG TGGCTGGAGT GGGCGGTGAA  650    AY204742 (SEQ ID NO: 62)
..........

AGAATATGGC CTTCCAGACG TCAACATCTT GTTATTCCAG AACATCGATG  550    ERG8     (SEQ ID NO: 30)
AGAATATGGC CTTCCAGACG TCAACATCTT GTTATTCCAG AACATCGATG  700    AY204742 (SEQ ID NO: 62)
..........

GGAAGGAACT GTGCAAGATG ACCAAGGACG ACTTCCAGAG GCTCACCCCC  600    ERG8     (SEQ ID NO: 30)
GGAAGGAACT GTGCAAGATG ACCAAGGACG ACTTCCAGAG GCTCACCCCC  750    AY204742 (SEQ ID NO: 62)
..........

AGCTACAACG CCGACATCCT TCTCTCACAT CTCCACTACC TCAGAGAGAC  650    ERG8     (SEQ ID NO: 30)
AGCTACAACG CCGACATCCT TCTCTCACAT CTCCACTACC TCAGAGAGAC  800    AY204742 (SEQ ID NO: 62)
..........

TCCTCTTCCA CATTTGACTT CAGATGATGT TGATAAAGCC TTACAAAACT  700    ERG8     (SEQ ID NO: 30)
TCCTCTTCCA CATTTGACTT CAGATGATGT TGATAAAGCC TTACAAAACT  850    AY204742 (SEQ ID NO: 62)
..........
```

Figure 1B

```
CTCCACGGTT AATGCATGCT AGAAACACAG GGGGTGCAGC TTTTATTTTC  750  ERG8      (SEQ ID NO: 30)
CTCCACGGTT AATGCATGCT AGAAACACAG GGGGTGCAGC TTTTATTTTC  900  AY204742  (SEQ ID NO: 62)

CCAAATACTT CAGTATATCC TGAAGCTACG CAAAGAATTA CAACTAGGCC  800  ERG8      (SEQ ID NO: 30)
CCAAATACTT CAGTATATCC TGAAGCTACG CAAAGAATTA CAACTAGGCC  950  AY204742  (SEQ ID NO: 62)

AGGTACGAAA ACACCCCTGT GTGATCTCTT CATTGAGAGA CATCCCAGAT  850  ERG8      (SEQ ID NO: 30)
AGGTACGAAA ACACCCCTGT GTGATCTCTT CATTGAGAGA CATCCCAGAT 1000  AY204742  (SEQ ID NO: 62)

GTCCTGCTGA GATCCGTGCC CTAAGTCACG TGATACAAAG AGAGCTGATC  900  ERG8      (SEQ ID NO: 30)
GTCCTGCTGA GATCCGTGCC CTAAGTCACG TGATACAAAG AGAGCTGATC 1050  AY204742  (SEQ ID NO: 62)

CCGGAGCTGA AGCCAGTCCC AGACAGTCTT ATTCTGCCTC TGTTGATTTG  950  ERG8      (SEQ ID NO: 30)
CCGGAGCTGA AGCCAGTCCC AGACAGTCTT ATTCTGCCTC TGTTGATTTG 1100  AY204742  (SEQ ID NO: 62)

GAGACTAAAT CCACTCAAAC CATTTCATTC AAAGACCACA CTAAAGGAAT 1000  ERG8      (SEQ ID NO: 30)
GAGACTAAAT CCACTCAAAC CATTTCATTC AAAGACCACA CTAAAGGAAT 1150  AY204742  (SEQ ID NO: 62)
```

Figure 1C

```
TAAGAGCAGA TTAGCCCTTT AACTAGCTTT TCAGAAAGAC AGATGGGCAA 1050  ERG8             (SEQ ID NO: 30)
TAAGAGCAGA TTAGCCCTTT AACTAGCTTT TCAGAAAGAC AGATGGGCAA 1200  AY204742         (SEQ ID NO: 62)
..........

AGAAGGCATC CTGGATGCCT GGCAGTTAGG AATAGGCCGA CTTTTGAACT 1100  ERG8             (SEQ ID NO: 30)
AGAAGGCATC CTGGATGCCT GGCAGTTAGG AATAGGCCGA CTTTTGAACT 1250  AY204742         (SEQ ID NO: 62)
..........

AACAGAAGGA TCTGTCCCTC CTCGGGGGAA GAGCACAAAA CAAGGACACT 1150  ERG8             (SEQ ID NO: 30)
AACAGAAGGA TCTGTCCCTC CTCGGGGGAA GAGCACAAAA CAAGGACACT 1300  AY204742         (SEQ ID NO: 62)
..........

CCCCAGATTC ACAGTGACCG ATTATCAGTA TGTCACAAGA AGCCAGTCTT 1200  ERG8             (SEQ ID NO: 30)
CCCCAGATTC ACAGTGACCG ATTATCAGTA TGTCACAAGA AGCCAGTCTT 1350  AY204742         (SEQ ID NO: 62)
..........

GCAGAGCAGA AGCATGCAAC CAGTAGTATT TACATCTGAA TCTTACTGCC 1250  ERG8             (SEQ ID NO: 30)
GCAGAGCAGA AGCATGCAAC CAGTAGTATT TACATCTGAA TCTTACTGCC 1400  AY204742         (SEQ ID NO: 62)
..........

TGTCCTCCAA ATGATTTAAT TAGGTAATAA ATTTACATGC CATTCATGCA 1300  ERG8             (SEQ ID NO: 30)
TGTCCTCCAA ATGATTTAAT TAGGTAATAA ATTTACATGC CATTCATGCA 1450  AY204742         (SEQ ID NO: 62)
..........

AAAATAAACA TCTATCAAGT GCCCATTAGT GCCAAGCGTG GTGTTAGACT 1350  ERG8             (SEQ ID NO: 30)
AAAAAAAAAA                                                   AY204742         (SEQ ID NO: 62)
..........
```

Figure 1D

```
CTGGGAATAT ATAGATGAAC CAGGCTTCAG TAAGCTTCCT GTCTTCAGAA 1400 ERG8   (SEQ ID NO: 30)

AGTTTACTTC TTCATTCAGC TTGGTTTGTT CATTTGCTGA GTGCCTCCTC 1450 ERG8   (SEQ ID NO: 30)

TGTGCCAGCC ACGGATGGTA TGATGGTGAA CAAACCGAAA TGTTTTGCCT 1500 ERG8   (SEQ ID NO: 30)

CCAGTTCTAG ATGTTTCAGT AGAGTGACCT AGAGCCAGAG AGACACATAT 1550 ERG8   (SEQ ID NO: 30)

GTACACATAA ATGTTTTCCC TAATGTGATA GATTTTATGG TAGAGGAACC 1600 ERG8   (SEQ ID NO: 30)

ACTTCTAGCA ATACAGGGCG TAGGAGCAGG GGTGGGGAGG AACTCAATCC 1650 ERG8   (SEQ ID NO: 30)

CCCATGAAAG GCATAAAGTT GCTTTCCAGA GGAATGGCCA CATGGCAAAG 1700 ERG8   (SEQ ID NO: 30)

GGGAATTAGA TGTTTGCCAG ACGAATAATG AGCAGGGAGA GAGGGCATTT 1750 ERG8   (SEQ ID NO: 30)

CCCAGAAGGG TATAGCTTGC CTTTAGCATT TGTCCTCTCC CTGGGACTTA 1800 ERG8   (SEQ ID NO: 30)

CATCAGCCCG ATAAGCTAGG TATCATTGTA CCAGCCTCAC AGCTGATGAC 1850 ERG8   (SEQ ID NO: 30)

ATTGTGTTCA GGGTGGTGGG ATGGTTTCTC CATATTCATA CATGCTTCCA 1900 ERG8   (SEQ ID NO: 30)

GAATTCATGT TAAACTCTAT CACATATCCG GAATACACAA GTCTCAGTTC 1950 ERG8   (SEQ ID NO: 30)
```

Figure 1E

```
GAACTGGTTC AAGATCTAGG CTTGGCAACT ACTCTTTCTT TCTAATGAGA 2000 ERG8   (SEQ ID NO: 30)

AAGACTGGGG GCCCAGGGAG CTAAAGAGAA TGAATGAGGA AGCTTCTCAG 2050 ERG8   (SEQ ID NO: 30)

GCTGTTCAAA TACTGACACT GCCCTGGTTA CTGCCTAGTG ACTTCAGGCT 2100 ERG8   (SEQ ID NO: 30)

GGCAATTTTC TCTTCTCTAA CGTCAGAGAA AAAGTTTACT GTCTTGCTCC 2150 ERG8   (SEQ ID NO: 30)

TGGGAAGCAT GATGGAAAGG CTTAGCAGCT AAGGGGTACT AAGAGGTAGT 2200 ERG8   (SEQ ID NO: 30)

AAGTCATCTC TGTCATGTAA AAGATTTCAC AGGCCATTGA AACATGGGCA 2250 ERG8   (SEQ ID NO: 30)

AGACCCAGTG CCTAGAGTCT GCAAGATTGG TCCTAAAGAC ATCCACCACG 2300 ERG8   (SEQ ID NO: 30)

TGTATTGCGA GTGGAAAATA GAAATTCATG TTTGACTCAA GCTTTAGAGA 2350 ERG8   (SEQ ID NO: 30)

TTTTGTAATT CTGTGAGCAT TTAAAAAATA TTTCCATATA AACTAAAAAA 2400 ERG8   (SEQ ID NO: 30)

ATAAAAACTA TTTCCAAAAA AAAAAAAAAA AAAAACTCGA G          2441 ERG8   (SEQ ID NO: 30)
```

Figure 1F

| Correlation | | No fusion detected | | | ERG Fusion A | | | High ERG fusion A* (Mean=0.61) | | | Low ERG fusion A* (Mean=4.64) | | |
|---|---|---|---|---|---|---|---|---|---|---|---|---|---|
| | | N | R | P value | N | R | P value | N | R | P value | N | R | P value |
| ERG fusion | ERG1 | - | - | - | 59 | 0.49 | <.0001 | 30 | 0.49 | 0.0055 | 29 | 0.33 | 0.079 |
| | AR | - | - | - | 61 | 0.22 | 0.0862 | 30 | 0.4 | 0.0303 | 31 | 0.08 | 0.672 |
| | PSA | - | - | - | 58 | 0.48 | 0.0001 | 31 | 0.56 | 0.0011 | 27 | 0.25 | 0.2037 |
| | PMEPA1 | | | | 50 | 0.55 | <.0001 | 24 | 0.59 | 0.0026 | 26 | 0.36 | 0.0718 |
| | LTF | - | - | - | 45 | 0.12 | 0.439 | 20 | 0.36 | 0.1203 | 25 | -0.11 | 0.6048 |
| ERG1 | AR | 26 | 0.48 | 0.0126 | 56 | 0.38 | 0.0039 | 27 | 0.57 | 0.002 | 29 | 0.06 | 0.7669 |
| | PSA | 27 | -0.01 | 0.9428 | 52 | 0.59 | <.0001 | 28 | 0.67 | 0.0001 | 24 | 0.09 | 0.6807 |
| | PMEPA1 | 22 | 0.28 | 0.1993 | 48 | 0.68 | <.0001 | 23 | 0.78 | <.0001 | 25 | 0.46 | 0.0211 |
| | LTF | 20 | 0.36 | 0.1125 | 43 | 0.01 | 0.9391 | 19 | -0.07 | 0.7717 | 24 | 0.01 | 0.9556 |

* Median split (median=2.635), N=65

Figure 8

A.
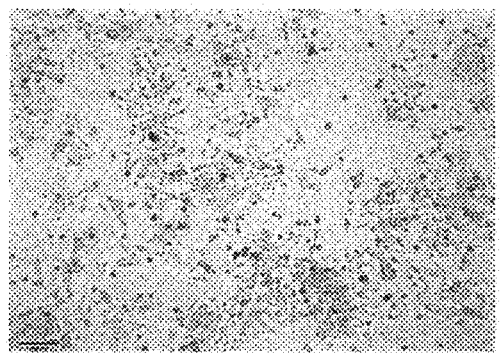
B.
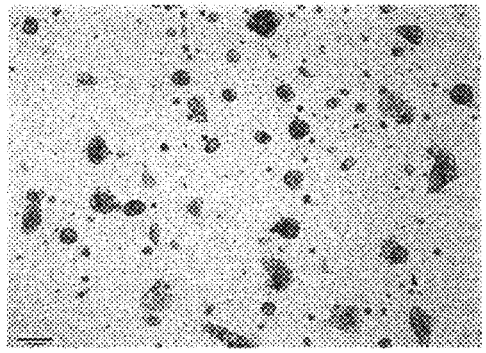
Figure 11

PROSTATE CANCER-SPECIFIC ALTERATIONS IN ERG GENE EXPRESSION AND DETECTION AND TREATMENT METHODS BASED ON THOSE ALTERATIONS

CROSS-REFERENCE TO RELATED APPLICATIONS

This application is a Continuation-in-Part of PCT/US2007/080826, filed Oct. 9, 2007, which in turn claims the benefit of U.S. provisional application No. 60/929,505, filed Jun. 29, 2007, and 60/850,254, filed Oct. 10, 2006. The entire disclosure of each of these applications is relied upon and incorporated by reference.

GOVERNMENT LICENSE RIGHTS

The U.S. Government has a paid-up license in this invention and the right in limited circumstances to require the patent owner to license others on reasonable terms as provided for by the terms of grant R01 DK065977 awarded by the National Institutes of Health.

TECHNICAL FIELD

The invention relates to polynucleotide and polypeptide sequences that are involved in, or associated with, prostate cancer. The invention further relates to therapeutic compositions and to methods of detecting, diagnosing, and treating prostate cancer.

BACKGROUND

ETS Related Gene (ERG), a member of the ETS transcription family, was initially isolated and described in 1987 (Reddy et al., PROC. NATL. ACAD. SCI. USA 84:6131-35 (1987); Rao et al., SCIENCE 237:635-39 (1987)). Like other members of the ETS family, it plays a central role in mediating mitogenic signals transmitted by major cellular pathways, including the MAPK pathway. Proteins in the ETS family show a wide variety of expression patterns in human tissues. ERG is expressed in endothelial tissues, hematopoietic cells, kidney, and in the urogenital track. (Oikawa et al., GENE 303:11-34 (2003).) Expression of ERG has also been detected in endothelial cells (microvessels) of the stroma in a small proportion of prostate cancer. (Gavrilov et al., EUR J CANCER 37: 033-40 (2001).)

The ERG protein participates in the regulation of gene expression by binding both to DNA comprising a 5'-GGA(A/T)-3' consensus sequence and to the Jun/Fos heterodimer. These interactions occur via the highly conserved ETS domain. (Verger et al., J BIOL CHEM 276: 17181-89 (2001).) Splice variants exist, and of the nine that have been reported, ERG6 and ERG9 have multiple stop codons that likely render them non-functional. (Owczarek et al., GENE 324: 65-77 (2004).) ERG7 and ERG8 can be distinguished from ERG1-5 by the absence of exon 16. (Id.) In addition, the ERG8 transcript is unique in its inclusion of a 3' sequence following exon 12, a portion of which forms part of the open reading frame. (Id.) ERG8 had been previously described as a 1460 base pair linear mRNA, with the National Center for Biotechnology Information ("NCBI") Accession No. AY204742. (Owczarek et al. (2004).)

ERG, like other members of the ETS family, is a proto-oncogene with transforming activity. (Oikawa et al., GENE 303:11-34 (2003); Hsu et al., J CELL BIOCHEM 91:896-903 (2004); Reddy et al., PROC NATL ACAD SCI USA, 84:6131-35 (1987); Hart et al., ONCOGENE 10:1423-30 (1995); Sementchenko et al., ONCOGENE 17:2883-88 (1998).) Chromosomal translocations involving ERG have been linked to Ewing sarcoma, myeloid leukemia, and cervical carcinoma. (Oikawa et al., GENE 303:11-34 (2003).) It has recently been shown that ERG1 is the most commonly overexpressed proto-oncogene in malignant prostatic tissue. (Petrovics et al., ONCOGENE 24:3847-52 (2005).) Independently, Tomlins et al., SCIENCE 310:644-48 (2005), described novel gene fusions involving ERG and TMPRSS2, an androgen-sensitive gene, that may provide at least one possible mechanism for ERG1 overexpression. At least two additional studies have confirmed ERG rearrangements in prostate cancer. (Soller et al., GENES CHROMOSOMES CANCER 45:717-19 (2006); Yoshimoto et al., NEOPLASIA 8:465-69 (2006).)

Although prostate cancer is the most common non-skin cancer in North American men and the third leading cause of cancer mortality (Jemal et al., CANCER J CLIN 56:106-30 (2005)) remarkably little is known about critical events in prostatic carcinogenesis. While recent reports of high frequency genomic rearrangements involving the ERG locus and ERG1 overexpression are intriguing, there remains a need in the art to identify and characterize the gene expression products of the ERG locus in prostate cancer. Cancer-derived transcripts, splice variant transcripts, and altered expression ratios between transcripts are highly specific tools that can be used for cancer diagnosis throughout the different stages of cancer development. In addition, targeted inhibition or activation of these products, and/or direct manipulation of cancer-specific promoters, can be used as highly selective therapeutic strategies to target the causative root of cancer. Thus, the identification of molecular alterations specific for prostate cancer would not only permit optimization of diagnosis and prognosis but also would permit establishment of individualized treatments tailored to the molecular profile of the tumor.

In addition, while prostate cancer is increasingly detected early, the prognosis of individual patients remains a challenge. Identification of molecular biomarkers representing functionally relevant pathways that can distinguish between aggressive and indolent forms of prostate cancer at early stages will have tremendous impact in improving prognostic and therapeutic decisions. Other than serum PSA, currently there are no rational (tumor biology based) prognostic or therapeutic molecular biomarkers available in the clinical practice of prostate cancer.

While 80% of prostate cancer patients respond well to surgery, radiation therapy or watchful waiting, about 20% will develop metastasis that is often fatal to patients. Initially, prostate cancer development is driven by the androgen receptor (AR) pathway. (Heinlein et al., ENDOCRINE REV 25:276-308 (2004); Linja et al., J STEROID BIOCHEM MOL BIOL 92: 255-64 (2004); Shaffer et al., LANCET ONCOL 4:407-14 (2003); Chen et al., NAT MED 10: 26-7 (2004).) However, frequent alterations of AR structure and/or function are well recognized during prostate cancer progression especially with metastatic disease. Other genetic pathways that are often altered in these late stage androgen-independent tumors include p53 mutations, BCL2 overexpression and mutations or reduced expression of PTEN. (Shaffer et al., LANCET ONCOL 4:407-14 (2003).) Importantly, both p53 and PTEN pathways may affect AR functions.

Defects in AR-mediated signaling are increasingly highlighted for potential causal roles in prostate cancer progression. (Heinlein et al., ENDOCRINE REV 25:276-308 (2004); Dehm et al., J CELL BIOCHEM 99: 333-344 (2006).) Prostate cancer associated alterations of AR functions by various mechanisms, including AR mutations, AR gene amplification, altered AR mRNA or AR protein levels, changes in AR interaction with co-activators/co-repressors and ligand independent AR activation by growth factors/cytokines, may all contribute to prostate cancer progression. (Gelmann, J CLIN ONCOL 20:3001-15 (2002); Grossman et al., J NATL CANCER INST 93: 1687-97 (2001).) Due to the lack of precise knowledge of AR dysfunctions in pathologic specimens, it is difficult to identify patients with functional defects of AR.

The choice of therapy for late stage prostate cancer is systemic androgen ablation, which eventually fails in most patients. Therefore, the knowledge of AR pathway dysfunctions that are predictive of androgen ablation therapy failure would significantly impact the patient stratification for new emerging therapeutic strategies.

Unlike in breast cancer where estrogen receptor protein status in primary tumor is effectively used in making therapeutic and prognostic decisions (Yamashita et al., BREAST CANCER 13(1):74-83 (2006); Martinez et al., AM J SURG 191 (2):281-3 (2006); Giacinti et al., ONCOLOGIST 11(1):1-8 (2006); Regan et al., BREAST 14(6):582-93 (2005); Singh et al., J CELL BIOCHEM 96(3):490-505 (2005)), AR protein expression status does not appear to be useful in prostate cancer, likely because many factors besides AR protein expression level may affect AR activity. Although AR expression can be detected throughout the progression of prostate cancer, it is heterogeneous and changes over time. Several studies have indicated that AR expression is reduced in poorly differentiated areas with a higher Gleason score. (Heinlein et al., ENDOCRINE REV 25:276-308 (2004); Linja et al., J STEROID BIOCHEM MOL BIOL 92: 255-64 (2004); Shaffer et al., LANCET ONCOL 4:407-14 (2003); Chen et al., NAT MED 10: 26-7 (2004); Gelmann, J CLIN ONCOL 20:3001-15 (2002); Grossman et al., J NATL CANCER INST 93:1687-97 (2001); Krishnan et al., CLIN CANCER RES 6:1922-30 (2000).)

In contrast, some recent reports found that higher AR expression is associated with higher clinical stage, higher Gleason score, and with decreased PSA recurrence-free survival. (Linja et al., CANCER RES 61:3550-55 (2001); Sweat et al., J UROL 161:1229-32 (1999); Li et al., AM J SURG PATHOL 28:928-34 (2004).) Part of the reason for this controversy is the inherent heterogeneity of AR expression in the prostate and the semi-quantitative nature of immunohistochemical evaluations. (Krishnan et al., CLIN CANCER RES 6:1922-30 (2000).) In recent years, our laboratory has established novel insights into the androgen regulated transcriptome and identified AR targets which have promise in defining the role of AR dysfunctions in prostate cancer, as well as in providing novel biology based biomarkers and therapeutic targets during prostate cancer progression. (Xu et al., CANCER RES. 63(15):4299-304 (2003); Segawa et al., ONCOGENE 21(57): 8749-58 (2002); Xu et al., INT J CANCER 92(3):322-8 (2001); Xu et al., GENOMICS 66(3): 257-263 (2000); Masuda et al., J MOL BIOL 353(4):763-71 (2005); Richter et al., PROSTATE CANCER PROSTATIC DIS 10(2):114-8 (2007).

Nevertheless, a need still exists to streamline the functional evaluation of AR defects at early stages of prostate cancer, when the impact of this knowledge on disease management will be more profound. The present application meets this need by providing a read out for the measurement of the expression of carefully selected AR downstream targets. This read out provides information on the in vivo functional status of AR in prostate cancer cells, which helps to stratify patients based on AR signal amplitude and can be used to help prognose prostate cancer and provide new ways of managing and treating these patients.

In particular, a need exists to further characterize the ERG8 protooncogene and its role in prostate cancer. ERG8 provides an untapped source of diagnostic, prognostic, and therapeutic agents applicable to prostate cancer Citation of references herein shall not be construed as an admission that such references are prior art to the present invention.

SUMMARY

Transcription of the ERG gene is altered in prostate cancer cells compared to benign cells. The present application describes for the first time the complete ERG8 nucleotide sequence and also describes the predominant expression of the ERG8 isoform in cancerous cells. It also provides the sequence and characterization of two unique, cancer-specific transcripts of the ERG locus, ERG Prostate Cancer-specific Isoform 1 (EPC1) and EPC2. The disclosed ERG isoforms can be used alone or in combination as biomarkers of prostate cancer, as targets for therapeutic intervention, or to develop therapeutic agents. In addition, the disclosure describes a novel, prostate cancer-specific ERG promoter. The ERG promoter can be used to selectively target expression of therapeutic proteins, such as cellular toxins, to prostate cancer cells. Polynucleotide transcripts produced from this novel promoter can also be detected as biomarkers for prostate cancer diagnosis, or to aid in prognosis of prostate cancer.

In one aspect, the disclosure provides the nucleic acid sequences and encoded protein sequences for cancer-specific gene transcripts of the ERG locus, including ERG8, EPC1, and EPC2. Antibodies to the encoded polypeptides, and to fragments of those polypeptides, are also described. In some embodiments, the antibody binds an epitope of the polypeptide or polypeptide fragment that is linear, whereas in other embodiments the epitope is conformational. In some embodiments, the epitope is contained within, or comprising, the unique carboxy-terminus of the EPC1 or EPC2 polypeptide. Some of the antibodies that bind an epitope in the carboxy terminus of EPC1 or EPC2 also bind the respective EPC1 or EPC2 polypeptide.

The disclosure further provides kits for detecting prostate cancer. These kits can be used to detect (either qualitatively or quantitatively) nucleic acids or proteins that serve as prostate cancer markers. For example, the expression of prostate cancer-specific isoforms of the ERG gene, such as ERG8, EPC1, EPC2, or the transcripts produced by the prostate cancer-specific promoter, when detected in a biological sample from a subject, either alone or in combination with other cancer markers, can be used to indicate the presence of prostate cancer in the subject or a higher predisposition of the subject to develop prostate cancer, or they can be used to predict the severity or stage of prostate cancer, such as whether the cancer is high risk or a moderate risk cancer.

In some embodiments, the kits comprise a nucleic acid probe, such as the probes described elsewhere in the disclosure, that hybridizes under defined conditions to an ERG sequence. The nucleic acid probe can hybridize to SEQ ID NO: 1 (ERG8), SEQ ID NO: 3 (EPC1), SEQ ID NO: 5 (EPC2), SEQ ID NO: 30 (ERG8), or SEQ ID NO: 46 (ERG8) (or sequences complimentary to SEQ ID NO: 1, SEQ ID NO: 3, SEQ ID NO: 5, SEQ ID NO: 30, or SEQ ID NO: 46), or a combination of probes can be used to hybridize to ERG8 and EPC1, ERG8 and EPC2, EPC1 and EPC2, or even ERG8, EPC1, and EPC2. In other embodiments, the kits comprise first and second oligonucleotide primers that hybridize to non-overlapping sequences in ERG8 (SEQ ID NOS: 1, 30, and 46), EPC1 (SEQ ID NO: 3), or EPC2 (SEQ ID NO: 5). In some embodiments, primer pairs that hybridize to ERG8 and EPC1; ERG8 and EPC2; EPC1 and EPC2; or ERG8, EPC1, and EPC2, are used in combination. In such cases, one or more of the ERG8, EPC1, or EPC2 primers may be the same.

The disclosure additionally describes diagnostic kits comprising an anti-ERG isoform-specific antibody, for example, an anti-ERG8 antibody, an anti-EPC1 antibody, or anti-EPC2 antibody. In one embodiment, the disclosure provides an anti-EPC1 antibody that binds an epitope comprising acids amino acids 217 to 220 of SEQ ID NO: 4. In another embodiment, the antibody is an anti-EPC2 antibody that binds an epitope within or comprising amino acids 28 to 97 of SEQ ID NO: 6. In each case, the epitope can be a linear epitope or a conformational epitope. In some embodiments, combinations of antibodies can be included in the kit. For example, a kit can comprise anti-ERG8 and anti-EPC1 antibodies, anti-ERG8 and anti-EPC2 antibodies, anti-EPC1 and anti-EPC2 antibodies, or anti-ERG8, anti-EPC1, and anti-EPC2 antibodies. The antibodies can be, optionally, detectably labeled.

ERG isoform expression can be used to diagnose or prognose prostate cancer. The disclosure therefore also provides methods for detecting the expression of one or more of ERG8, EPC1, or EPC2 in a biological sample, such as prostate tissue, blood, serum, plasma, urine, saliva, or prostatic fluid. For example, in some embodiments, the methods comprise detecting amplification products of ERG8, EPC1, or EPC2 using hybridization-based techniques. In other embodiments, amplification products are size separated and visualized as part of the detection methods. The methods of diagnosing or prognosing prostate cancer can further comprise measuring the expression level (e.g. mRNA or polypeptide) of ERG8, EPC1, or EPC2, and correlating the expression level of the ERG isoform with the presence of prostate cancer or a higher predisposition to develop prostate cancer in the subject, or with the severity or stage of prostate cancer, such as high risk or moderate risk prostate cancer.

In some embodiments, the methods comprise detecting the expression of the ERG8 isoform. In other embodiments, it is the expression of the EPC1 isoform that is detected. In yet other embodiments, the EPC2 isoform is detected. In still other embodiments, the methods comprise detecting the ERG8 and EPC1 isoforms in combination, the ERG8 and EPC2 isoforms in combination, the EPC1 and EPC2 isoforms in combination, or the combination of the ERG8, EPC1, and EPC2 isoforms. In each case, each ERG isoform can be detected and/or measured by detecting and/or measuring the transcript, or by detecting and/or measuring the corresponding polypeptide.

Therapeutic methods of treating prostate cancer and treating disorders of prostate hyperproliferation are also disclosed. For example, the disclosure provides methods of treating prostate cancer comprising destabilizing a prostate cancer-specific ERG gene transcript in prostate cancer cells. In some embodiments, the methods comprise destabilizing one, all, or any combination of ERG8, EPC1, EPC2, ERG1, ERG2, and/or ERG3 transcripts, resulting in degradation of those transcripts and inhibition of expression of the encoded polypeptide(s). In one embodiment, the destabilization employs siRNA. In another embodiment, the methods employ small hairpin RNAs (shRNA). In yet another embodiment, an antisense molecule is used to destabilize the transcript(s). In still another embodiment, a ribozyme is used to cause destabilization. Small molecule inhibitors can also be used to inhibit expression of one or more ERG isoforms. The disclosure also provides methods of using an antibody to one or more ERG isoforms to treat prostate cancer or disorders of prostate hyperproliferation. Thus, in varying embodiments the disclosure provides methods of treating prostate cancer or disorders of prostate hyperproliferation comprising administering an anti-ERG8, an anti-EPC1, an anti-EPC2, an anti-ERG1, and anti-ERG2, an anti-ERG3 antibody, or a combination of those antibodies. In some embodiments, a single antibody may be specific for one or more proteins encoded by the disclosed ERG isoforms.

In another embodiment, the present application provides a panel of biomarkers for prostate cancer, methods and systems for using those biomarkers to diagnose and prognose prostate cancer, and diagnostic and prognostic kits comprising reagents used to detect the biomarkers. In one embodiment the panel comprises a combination of two or more of a set of six androgen inducible/co-regulated genes (PSA/KLK3, PMEPA1, NKX3.1, ODC1, AMD1, and ERG). In some embodiments, the ERG gene is EPC1, EPC2, ERG1, ERG2, ERG3, ERG8, or combinations thereof.

The present application also provides prognostic kits that detect or measure the levels of two or more androgen inducible/co-regulated genes. The prognostic kits are used in methods of predicting the functional status of in vivo androgen receptor signaling or in methods of predicting prostate cancer progression or severity, such as predicting whether the prostate cancer is a moderate risk prostate cancer or a high risk prostate cancer, predicting the prostate cancer stage (e.g., using the T staging system (pTX, pT0, PT1, pT2, pT3, pT4) or the Whitmore-Jewett system (A, B, C, D)), or predicting whether the prostate cancer is progressing, regressing, or in remission. The prognostic kits can also be used to predict disease-free survival following prostatectomy, which can be defined, for example, by serum PSA level equal or higher than 0.2 ng/ml after prostatectomy. In some embodiments, the prognostic panel comprises two or more of the following genes: PSA/KLK3, PMEPA1, NKX3.1, ODC1, AMD1, and ERG. In certain embodiments, the ERG gene is EPC1, EPC2, ERG1, ERG2, ERG3, ERG8, or combinations thereof. Accordingly, assays using the prognostic kits can detect or measure the levels of two or more of these genes. For example, a prognostic kit can be used to measure the levels of two, three, four, five, six, or even more androgen inducible/co-regulated genes.

In certain embodiments, the prognostic assay further comprises detecting or measuring PSA, % PSA, PSA doubling time, PSA velocity, prostate volume or a combination of these indicators.

In prognostic embodiments, the method of prognosing prostate cancer can comprise detecting or measuring in a biological sample from an individual the expression of two or more of genes chosen from PSA/KLK3, PMEPA1, NKX3.1, ODC1, AMD1, and ERG; and comparing, for the expression of each gene detected or measured, the results obtained in (a) with the expression of the same gene in a control sample.

In a prognostic method, the altered expression of the two or more genes in the patient sample relative to the control sample is predictive of disease severity, for example a moderate risk prostate cancer or a high risk prostate cancer. The altered expression may also be predictive of whether the prostate cancer is progressing, regressing, or in remission. Alternatively, a threshold value of gene expression can be selected and used as the control sample. In this case, if the gene expression level is less than the threshold value, it is considered reduced. The threshold value can be determined using known techniques. For example, the value can be determined from the mRNA copy number or the cycle threshold value.

Although increases and decreases of at least 10% relative to a control or threshold value can be used in the prognostic methods, other values may also be used. For example, the increase or decrease may be at least 20, 30, 40, 50, 60, 70, 80, 90, 100, 200, 300, 400, or even 500%. The increase or decrease may also be expressed in terms of statistical significance, where a statistically significant increase or decrease in expression, such as $p<0.05$, $p<0.01$, $p<0.005$, or $p<0.001$, indicates the presence of prostate cancer or a higher predisposition to develop prostate cancer, prostate cancer progression, or disease severity.

In some prognostic embodiments, a decrease in expression levels of the androgen inducible/co-regulated gene(s) is used to predict compromised androgen receptor signaling, which in turn is predictive of the presence or predisposition to develop high risk or advanced stage prostate cancer or a reduced disease-free survival time following prostatectomy.

The disclosure also provides methods of detecting the expression of two or more of PSA/KLK3, PMEPA1, NKX3.1, ODC1, AMD1, and ERG (including EPC1, EPC2, ERG1, ERG2, ERG3 or ERG8) in a biological sample, such as prostate tissue or a biofluid, such as, blood, serum, plasma, urine, saliva, or prostatic fluid. For example, in some embodiments, the methods comprise detecting amplification products of PSA/KLK3, PMEPA1, NKX3.1, ODC1, AMD1, and ERG using hybridization-based techniques. In other embodiments, amplification products are size separated and visualized as part of the detection methods. The methods of prognosing prostate cancer can also comprise measuring the expression level of the proteins encoded by PSA/KLK3, PMEPA1, NKX3.1, ODC1, AMD1, and ERG, for example by using an antibody.

Additional objects will be set forth in part in the description that follows, and in part will be understood from the description, or may be learned by practice of the invention. It is to be understood that both the foregoing general description and the following detailed description are exemplary and explanatory only and are not restrictive of the invention as claimed.

BRIEF DESCRIPTION OF THE DRAWINGS

This application contains two drawings, FIGS. 20 and 21, which are executed in color. Copies of this application publication with color drawings will be provided by the U.S. Patent and Trademark Office upon request and payment of the necessary fee.

FIG. 1 shows the nucleotide sequence of the complete ERG8 gene (SEQ ID NO: 30), aligned with the partial gene sequence of NCBI AY204742 (SEQ ID NO: 62).

FIG. 5 shows the number of copies of the ERG isoforms.

FIG. 8 provides the results of a Pearson correlation analysis of TMPRSS2-ERG fusion A transcript expression with ERG1, AR, PSA, PMEPA1 and LTF expression in tumor tissue.

FIG. 11 shows the results of siRNA inhibition of ERG expression in VCaP prostate cancer cells. FIG. 11A shows a microscope field of control VCaP cells and FIG. 11B shows a microscope field of cells treated with siRNA-1 (SEQ ID NO: 28).

FIGS. 22A and 22B show VCaP and LNCaP cells, respectively, infected with adenoviral ERG ("Ad-ERG") or adenoviral control ("Control") vectors. Cell lysates prepared at 24, 48, and 72 hours post-infection were analyzed by immunoblot using anti-ERG, anti-PSA, and anti-tubulin antibodies.

FIGS. 22C and 22D show ChIP assessment of AR recruitment to the KLK3/PSA gene AREIII enhancer in VCaP and LNCaP cells in response to the transient expression of ERG by adenoviral Ad-ERG or Control vectors. "Input" indicates control genomic DNA amplicons.

DETAILED DESCRIPTION

Definitions

Figure 2:
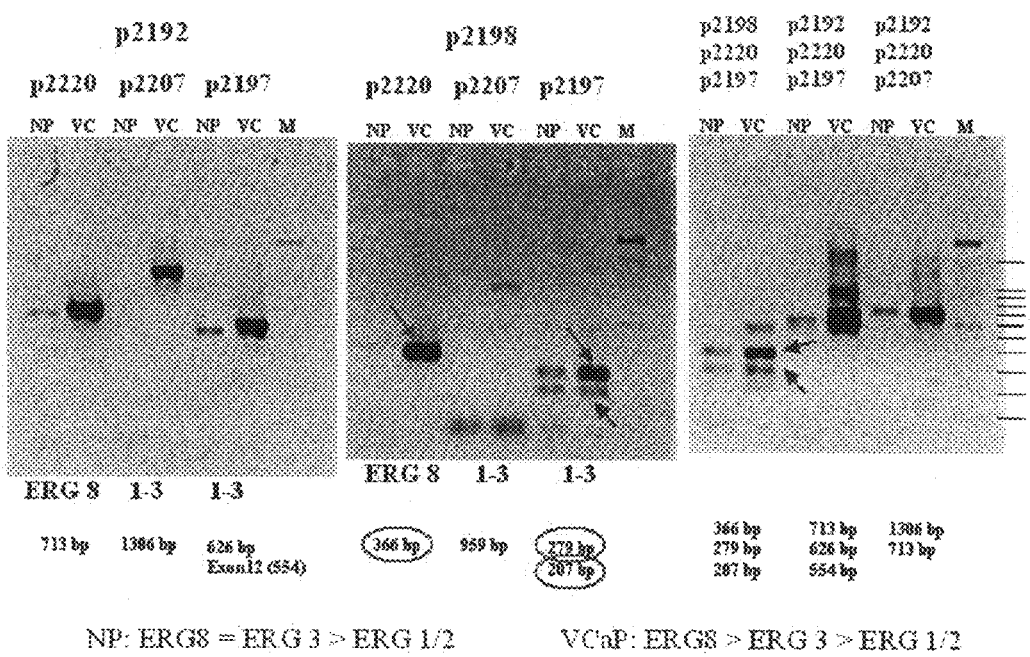
FIG. 2 presents PCR amplification gels of ERG1, ERG2, ERG3, and ERG8 transcripts in normal prostate tissue (NP) and in the prostate cancer cell line VCaP.

The term "ERG" refers to the ERG gene, as well as to the various ERG cDNAs and mRNAs described in the disclosure. Unless a specific isoform or subset of isoforms is indicated, the term ERG includes ERG1, ERG2, ERG3, ERG4, ERG5, ERG6, ERG7, ERG8, ERG9, EPC1, EPC2, and the truncated ERG transcripts that result from activation of the prostate cancer-specific promoter described herein. The phrasing "ERG, but not" one or more specifically mentioned ERG isoforms may be used in embodiments in which several different, but not ail, of the ERG isoforms are contemplated. The cDNA sequence of the ERG1 gene is published in GenBank under the accession number M21535. The cDNA sequence of the ERG2 gene is published in GenBank under the accession number M17254. The term "ERG8" refers to the isoform described, e.g., by SEQ ID NO: 1, SEQ ID NO: 30, and SEQ ID NO: 46. The exon usage of ERG isoforms 1-9 is presented in Owczarek et al., GENE 324:65-77 (2004). When the context does not clearly exclude it, ERG also refers to the various ERG polypeptides encoded by the different isoforms. Further, although italics are generally used to refer to nucleic acids, the use of italics is not to be construed as excluding the encoded polypeptide.

To "destabilize" one or more transcripts means to cause degradation of that/those transcript(s) such that expression of the encoded polypeptide(s) is inhibited or knocked-down. Silent interfering RNA (siRNA), small hairpin RNA (shRNA) (for example, as described by Paddison et al., GENES DEV 16(8):948-58 (2002), antisense molecules, ribozymes, and combinations of these approaches can be used in methods of destabilizing a transcript(s).

A "moderate risk" prostate cancer is cancer in which the patient has, for example, no PSA recurrence, a Gleason score of 6-7, T2a-T3b stage, no seminal vesicle invasion, and well- or moderately-differentiated tumor.

A "high risk" prostate cancer is cancer in which the patient has, for example, PSA recurrence, a Gleason score of 8-9, T3c stage, seminal vesicle invasion, and poor tumor differentiation.

The term "altered expression" refers both to qualitative differences (i.e., that gene or protein expression is detectable versus undetectable) and to quantitative differences (i.e., differences in measured levels of gene or protein expression).

The term "isolated" refers to a molecule that is substantially free of its natural environment. Any amount of that molecule elevated over the naturally occurring levels due to any manipulation, e.g., over expression, partial purification, etc., is encompassed with the definition. With regard to partially purified compositions only, the term refers to an isolated compound that is at least 50-70%, 70-90%, 90-95% (w/w), or more pure.

The phrase "substantially identical," or "substantially as set out," means that a relevant sequence is at least 70%, 75%, 80%, 85%, 90%, 95%, 97, 98, or 99% identical to a given sequence. By way of example, such sequences may be allelic variants, sequences derived from various species, or they may be derived from the given sequence by truncation, deletion, amino acid substitution, or addition. For polypeptides, the length of comparison sequences will generally be at least 20, 30, 50, 100 or more amino acids. For nucleic acids, the length of comparison sequences will generally be at least 50, 100, 150, 300, or more nucleotides. Percent identity between two sequences is determined by standard alignment algorithms such as, for example, Basic Local Alignment Tool (BLAST) described in Altschul et al., J MOL BIOL 215:403-410 (1990), the algorithm of Needleman et al., J MOL BIOL 48:444-453 (1970), or the algorithm of Meyers et al., COMPUT APPL BIOSCI 4:11-17 (1988).

"Protein" is used interchangeably with the terms "peptide" and "polypeptide" and refers to any chain of amino acids, regardless of length or posttranslational modification (e.g., glycosylation or phosphorylation), or source (e.g., species).

The terms "polynucleotide," "oligonucleotide," "nucleic acid," and "DNA" are used interchangeably herein and refer to deoxyribonucleic acid (DNA), and, where appropriate, ribonucleic acid (RNA). The term should also be understood to include nucleotide analogs, and single or double stranded polynucleotides. Examples of polynucleotides include, but are not limited to, plasmid DNA or fragments thereof, viral DNA or RNA, anti-sense RNA, etc. The term "plasmid DNA" refers to double stranded DNA that is circular.

As used herein the term "hybridization under defined conditions," or "hybridizing under defined conditions," is intended to describe conditions for hybridization and washes under which nucleotide sequences that are significantly identical or homologous to each other remain bound to each other. The conditions are such that sequences, which are at least about six and more preferably at least about 20, 30, 40, 50, 100, 150, 300, or more nucleotides long and at least about 70%, more preferably at least about 80%, even more preferably at least about 85-90% identical, remain bound to each other. The percent identity can be determined as described in Altschul et al., NUCLEIC ACIDS RES 25:3389-3402 (1997). Appropriate hybridization conditions can be selected by those skilled in the art with minimal experimentation as exemplified in Ausubel et al., CURRENT PROTOCOLS IN MOLEC BIOL, John Wiley & Sons (2004). Additionally, stringent conditions are described in Sambrook et al. MOLEC CLONING: A LABORATORY MANUAL, $3^{rd}$ ed., Cold Spring Harbor Laboratory Press (2001).

A nonlimiting example of defined conditions of low stringency is as follows: Filters containing DNA are pretreated for six hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in the hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. Other conditions of low stringency well known in the art may be used (e.g., as employed for cross-species hybridizations).

A non-limiting example of defined conditions of high stringency is as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in the prehybridization mixture containing 100 µg/ml denatured salmon sperm DNA and 5-20×10$^6$ cpm of $^{32}$P-labeled probe. Filters are washed for 1 hour at 37° C. in a solution containing 2×SSC, 0.01% PVP, 0.01%-Ficoll, and 0.01% BSA. This is followed by a wash in 0.1×SSC at 50° C. for 45 minutes. Another non-limiting example of defined conditions of high stringency is as follows: Prehybridization of filters containing DNA is carried out for eight hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 12 hours at 65° C. in the prehybridization mixture containing 100 µg/ml denatured salmon sperm DNA and 5-20×10$^6$ cpm of $^{32}$P-labeled probe. Filters are washed for 1 hour at 37° C. in a solution containing 2×SSC, 0.01% PVP, 0.01% Ficoll, and 0.01% BSA. This is followed by a wash in 0.1×SSC at 50° C. for 45 minutes. Other conditions of high stringency well known in the art may be used. An oligonucleotide hybridizes specifically to a target sequence under high stringency conditions.

The term "primer" or "oligonucleotide primer" means an oligonucleotide capable of binding to a region of a target nucleic acid, or its complement, and promoting nucleic acid amplification of the target nucleic acid. Generally, a primer will have a free 3' end that can be extended by a nucleic acid polymerase. Primers also generally include a base sequence capable of hybridizing via complementary base interactions either directly with at least one strand of the target nucleic acid or with a strand that is complementary to the target sequence. A primer may comprise target-specific sequences and optionally other sequences that are non-complementary to the target sequence. These non-complementary sequences may comprise, for example, a promoter sequence or a restriction endonuclease recognition site.

The term "solid support" means a material that is essentially insoluble under the solvent and temperature conditions of the assay method, comprising free chemical groups available for joining an oligonucleotide or nucleic acid. Preferably, the solid support is covalently coupled to an oligonucleotide designed to directly or indirectly bind a target nucleic acid. When the target nucleic acid is an mRNA, the oligonucleotide attached to the solid support is preferably a poly-T sequence. A preferred solid support is a particle, such as a micron- or submicron-sized bead or sphere. A variety of solid support materials are contemplated, such as, for example, silica, polyacrylate, polyacrylamide, a metal, polystyrene, latex, nitrocellulose, polypropylene, nylon or combinations thereof. In some embodiments, the solid support is capable of being attracted to a location by means of a magnetic field, such as a solid support having a magnetite core.

The term "detecting" or "detection" means any of a variety of methods known in the art for determining the presence of a nucleic acid or a protein. For example, hybridizing a labeled probe to a portion of a nucleic acid is one way to detect that nucleic acid. Binding an antibody that is either directly or indirectly labeled to a protein of interest is an example of a method of detecting that protein. Methods for labeling nucleic acids and antibodies (as well as other proteins) are well known in the art. Labels can be either detectable or functional labels, and include radiolabels (e.g., $^{131}$I, $^{125}$I, $^{35}$S, and $^{99}$Tc), enzymatic labels (e.g., horseradish peroxidase or alkaline phosphatase), chemiluminescent labels, and other chemical moieties (e.g., biotin). A labeled probe is an oligonucleotide that specifically binds to another sequence and contains a detectable group which may be, for example, a fluorescent moiety, a chemiluminescent moiety (such as an acridinium ester (AE) moiety that can be detected chemiluminescently under appropriate conditions (as described in U.S. Pat. No. 5,283,174)), a radioisotope, biotin, avidin, enzyme, enzyme substrate, or other reactive group. Other well known detection techniques include, for example, gel filtration, gel electrophoresis and visualization of the amplicons by, for example, staining with ethidium bromide, and High Performance Liquid Chromatography (HPLC). Antibody-based detection methods include ELISA, western blotting, radioimmunoassay (RIA), immunohistochemistry, and other techniques that are well known in the art. As used throughout the specification, the term "detecting" or "detection" includes either qualitative or quantitative detection.

The term "treatment" is used interchangeably herein with the term "therapeutic method" and refers to both therapeutic treatment and prophylactic/preventative measures. Those in need of treatment may include individuals already having a particular medical disorder as well as those who may ultimately acquire the disorder.

The term "effective dose," or "effective amount," refers to that amount of the compound that results in amelioration of symptoms in a patient or a desired biological outcome, e.g., inhibition of cell proliferation. The effective amount can be determined as described in the subsequent sections.

The term "modulatory compound" is used interchangeably with the term "therapeutic" and as used herein means any compound capable of "modulating" either prostate cancer-specific gene expression at the transcriptional, translational, or posttranslational levels or modulating the biological activity of a prostate cancer-specific polypeptide. The term "modulate" and its cognates refer to the capability of a compound acting as either an agonist or an antagonist of a certain reaction or activity. The term modulate, therefore, encompasses the terms "activate" and "inhibit." The term "activate," for example, refers to an increase in the expression of the prostate cancer-specific gene or activity of a prostate cancer-specific polypeptide in the presence of a modulatory compound, relative to the activity of the gene or the polypeptide in the absence of the same compound. The increase in the expression level or the activity is preferably at least about 10%, 20%, 30%, 40%, 50%, 60%, 70%, 80%, 90%, or higher. Analogously, the term "inhibit" refers to a decrease in the expression of the prostate cancer-specific gene or activity of a prostate cancer-specific polypeptide in the presence of a modulatory compound, relative to the activity of the gene or the polypeptide in the absence of the same compound. The decrease in the expression level or the activity is preferably at least about 10%, 20%, 30%, 40%, 50%, 60%, 70%, 80%, 90%, or higher. The expression level of the prostate cancer-specific gene or activity of a prostate cancer-specific polypeptide can be measured as described herein or by techniques generally known in the art.

"Antibody" refers to an immunoglobulin or fragment thereof, and encompasses any polypeptide comprising an antigen-binding fragment or an antigen-binding domain. The term includes but is not limited to polyclonal, monoclonal, monospecific, polyspecific, humanized, human, single-chain, chimeric, synthetic, recombinant, hybrid, mutated, grafted, and in vitro generated antibodies. Unless preceded by the word "intact", the term "antibody" includes antibody fragments such as Fab, F(ab')$_2$, Fv, scFv, Fd, dAb, and other antibody fragments that retain antigen-binding function. Unless otherwise specified, an antibody is not necessarily from any particular source, nor is it produced by any particular method.

The terms "specific interaction," "specific binding," or the like, mean that two molecules form a complex that is relatively stable under physiologic conditions. The term is also applicable where, e.g., an antigen-binding domain is specific for a particular epitope, which is carried by a number of antigens, in which case the specific binding member carrying the antigen-binding domain will be able to bind to the various antigens carrying the epitope. Specific binding is characterized by a high affinity and a low to moderate capacity. Non-specific binding usually has a low affinity with a moderate to high capacity. Typically, the binding is considered specific when the affinity constant $K_a$ is higher than $10^6$ M$^{-1}$, more preferably higher than $10^7$ M$^{-1}$, and most preferably $10^8$ M$^{-1}$. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of antibodies, ionic strength of the solution, temperature, time allowed for binding, concentration of non-related molecules (e.g., serum albumin, milk casein), etc.

Prostate Cancer-Specific ERG Nucleic Acids

The disclosure describes prostate cancer-specific ERG isoform nucleic acids, in particular, ERG8, EPC1, EPC2, and a prostate cancer-specific promoter located within exon 9 of the ERG gene. In the case of ERG8, a partial-length splice variant of the ERG gene has been described (Owczarek et al. (2004)), but the complete ERG8 nucleotide sequence and ERG8 overexpression in the context of prostate cancer was not previously known. ERG8 is herein reported to comprise 2441 nucleotides. It is overexpressed in 60-75% of prostate tumors, thus provides a target for the detection, prognosis, and treatment of prostate cancer.

The protein encoded by ERG8 lacks the DNA binding domain found in ERG1 and ERG2 but retains the entire protein-protein interaction domain. The expression of ERG8, therefore, likely results in the functional nullification of protein interaction partners of ERG-1 and ERG2, resulting in a dominant negative effect.

The disclosure also shows that fusions occur between ERG8 and TMPRSS2. An example of a TMPRSS2-ERG8 fusion transcript is:

| | | | | | |
|---|---|---|---|---|---|
| TAGGCGCGAG | CTAAGCAGGA | GGCGGAGGCG | GAGGCGGAGG | GCGAGGGGCG | 50 |
| GGGAGCGCCG | CCTGGAGCGC | GGCA░░AAGC | CTTATCAGTT | GTGAGTGAGG | 100 |
| ACCAGTCGTT | GTTTGAGTGT | GCCTACGGAA | CGCCACACCT | GGCTAAGACA | 150 |
| GAG*ATG*ACCG | CGTCCTCCTC | CAGCGACTAT | GGACAGACTT | CCAAGATGAG | 200 |
| CCCACGCGTC | CCTCAGCAGG | ATTGGCTGTC | TCAACCCCCA | GCCAGGGTCA | 250 |
| CCATCAAAAT | GGAATGTAAC | CCTAGCCAGG | TGAATGGCTC | AA░░AACTCT | 300 |
| CCTGATGAAT | GCAGTGTGGC | CAAAGGCGGG | AAGATGGTGG | GCAGCCCAGA | 350 |
| CACCGTTGGG | ATGAACTACG | GCAGCTACAT | GGAGGAGAAG | CACATGCCAC | 400 |
| CCCCAAACAT | GACCACGAAC | GAGCGCAGAG | TTATCGTGCC | AGCA░░TCCT | 450 |
| ACGCTATGGA | GTACAGACCA | TGTGCGGCAG | TGGCTGGAGT | GGGCGGTGAA | 500 |
| AGAATATGGC | CTTCCAGACG | TGAACATCTT | GTTATTCCAG | AACATCGATG | 550 |
| GGAAGGAACT | GTGCAAGATG | ACCAAGGACG | ACTTCCAGAG | GCTCACCCCC | 600 |
| AGCTACAACG | CCGACATCCT | TCTCTCACAT | CTCCACTACC | TCAGAGAG░░ | 650 |
| TCCTCTTCCA | CATTTGACTT | CAGATGATGT | TGATAAAGCC | TTACAAAACT | 700 |
| CTCCACGGTT | AATGCATGCT | AGAAACACA░░░GGGTGCAGC | | TTTTATTTTC | 750 |
| CCAAATACTT | CAGTATATCC | TGAAGCTACG | CAAAGAATTA | CAACTAGGCC | 800 |
| A░░TACGAAA | ACACCCCTGT | GTGATCTCTT | CATTGAGAGA | CATCCCAGAT | 850 |
| GTCCTGCTGA | GATCCGTGCC | CTAAGTCACG | TGATACAAAG | AGAGCTGATC | 900 |
| CCGGAGCTGA | AGCCAGTCCC | AGACAGTCTT | ATTCTGCCTC | TGTTGATTTG | 950 |
| GAGACTAAAT | CCACTCAAAC | CATTTCATTC | AAAGACCACA | CTAAAGGAAT | 1000 |
| TAAGAGCAGA | TTAGCCCTTT | AACTAGCTTT | TCAGAAAGAC | AGATGGGCAA | 1050 |
| AGAAGGCATC | CTGGATGCCT | GGCAGTTAGG | AATAGGCCGA | ATTTTGAACT | 1100 |
| AACAGAAGGA | TCTGTCCCTC | CTCGGGGAA | GAGCACAAAA | CAAGGACACT | 1150 |
| CCCCAGATTC | ACAGTGAC | | | | |

(SEQ ID NO: 1). The TMPRSS2-derived sequence at nucleotides 1-75 is shown in bold font. Exon junctions are shown in grey boxes. The initiation codon and stop codon are shown in bold italics. The unique 3' sequence at nucleotides 803-1168 is also shown in bold font. The amino acid sequence of ERG8 is:

| | | | | | |
|---|---|---|---|---|---|
| MTASSSSDYG | QTSKMSPRVP | QQDWLSQPPA | RVTIKMECNP | SQVNGSRNSP | 50 |
| DECSVAKGGK | MVGSPDTVGM | NYGSYMEEKH | MPPPNMTTNE | RRVIVPADPT | 100 |
| LWSTDHVRQW | LEWAVKEYGL | PDVNILLFQN | IDGKELCKMT | KDDFQRLTPS | 150 |
| YNADILLSHL | HYLRETPLPH | LTSDDVDKAL | QNSPRLMHAR | NTGGAAFIFP | 200 |
| NTSVYPEATQ | RITTRPGTKT | PLCDLFIERH | PRCPAEIRAL | SHVIQRELIP | 250 |
| ELKPVPDSLI | LPLLIWRLNP | LKPFHSKTTL | KELRAD | | |

(SEQ ID NO: 2). The unique carboxy terminus of ERG8 is shown in bold font.

The invention provides an isolated double-stranded nucleic acid molecule comprising a nucleic acid molecule with the polynucleotide sequence SEQ ID NO: 1, SEQ ID NO: 30, or SEQ ID NO: 46, or the complement of any of these. The entire nucleotide sequence of the ERG8/TMPRSS fusion molecule is:

| | | | | | |
|---|---|---|---|---|---|
| TAGGCGCGAG | CTAAGCAGGA | GGCGGAGGCG | GAGGCGGAGG | GCGAGGGGCG | 50 |
| GGGAGCGCCG | CCTGGAGCGC | GGCAGGAAGC | CTTATCAGTT | GTGAGTGAGG | 100 |
| ACCAGTCGTT | GTTTGAGTGT | GCCTACGGAA | CGCCACACCT | GGCTAAGACA | 150 |
| GAG*ATG*ACCG | CGTCCTCCTC | CAGCGACTAT | GGACAGACTT | CCAAGATGAG | 200 |
| CCCACGCGTC | CCTCAGCAGG | ATTGGCTGTC | TCAACCCCCA | GCCAGGGTCA | 250 |
| CCATCAAAAT | GGAATGTAAC | CCTAGCCAGG | TGAATGGCTC | AAGGAACTCT | 300 |
| CCTGATGAAT | GCAGTGTGGC | CAAAGGCGGG | AAGATGGTGG | GCAGCCCAGA | 350 |
| CACCGTTGGG | ATGAACTACG | GCAGCTACAT | GGAGGAGAAG | CACATGCCAC | 400 |
| CCCCAAACAT | GACCACGAAC | GAGCGCAGAG | TTATCGTGCC | AGCAGATCCT | 450 |
| ACGCTATGGA | GTACAGACCA | TGTGCGGCAG | TGGCTGGAGT | GGGCGGTGAA | 500 |
| AGAATATGGC | CTTCCAGACG | TCAACATCTT | GTTATTCCAG | AACATCGATG | 550 |
| GGAAGGAACT | GTGCAAGATG | ACCAAGGACG | ACTTCCAGAG | GCTCACCCCC | 600 |
| AGCTACAACG | CCGACATCCT | TCTCTCACAT | CTCCACTACC | TCAGAGAGAC | 650 |
| TCCTCTTCCA | CATTTGACTT | CAGATGATGT | TGATAAAGCC | TTACAAAACT | 700 |
| CTCCACGGTT | AATGCATGCT | AGAAACACAG | GGGTGCAGC | TTTTATTTTC | 750 |
| CCAAATACTT | CAGTATATCC | TGAAGCTACG | CAAAGAATTA | CAACTAGGCC | 800 |
| AGGTACGAAA | ACACCCCTGT | GTGATCTCTT | CATTGAGAGA | CATCCCAGAT | 850 |

-continued

```
GTCCTGCTGA GATCCGTGCC CTAAGTCACG TGATACAAAG AGAGCTGATC   900
CCGGAGCTGA AGCCAGTCCC AGACAGTCTT ATTCTGCCTC TGTTGATTTG   950
GAGACTAAAT CCACTCAAAC CATTTCATTC AAAGACCACA CTAAAGGAAT  1000
TAAGAGCAGA TTAGCCCTTT AACTAGCTTT TCAGAAAGAC AGATGGCAA   1050
AGAAGGCATC CTGGATGCCT GGCAGTTAGG AATAGGCCGA CTTTTGAACT  1100
AACAGAAGGA TCTGTCCCTC CTCGGGGAA  GAGCACAAAA CAAGGACACT  1150
CCCCAGATTC ACAGTGACCG ATTATCAGTA TGTCACAAGA AGCCAGTCTT  1200
GCAGAGCAGA AGCATGCAAC CAGTAGTATT TACATCTGAA TCTTACTGCC  1250
TGTCCTCCAA ATGATTTAAT TAGGTAATAA ATTTACATGC CATTCATGC   1300
           TCTATCAAGT GCCCATTAGT GCCAAGCGTG GTGTTAGACT  1350
CTGGGAATAT ATAGATGAAC CAGGCTTCAG TAAGCTTCCT GTCTTCAGAA  1400
AGTTTACTTC TTCATTCAGC TTGGTTTGTT CATTTGCTGA GTGCCTCCTC  1450
TGTGCCAGCC ACGGATGGTA TGATGGTGAA CAAACCGAAA TGTTTTGCCT  1500
CCAGTTCTAG ATGTTTCAGT AGAGTGACCT AGAGCCAGAG AGACACATAT  1550
GTACACATAA ATGTTTTCCC TAATGTGATA GATTTTATGG TAGAGGAACC  1600

ACTTCTAGCA ATACAGGGCG TAGGAGCAGG GGTGGGGAGG AACTCAATCC  1650
CCCATGAAAG GCATAAAGTT GCTTTCCAGA GGAATGGCCA CATGGCAAAG  1700
GGGAATTAGA TGTTTGCCAG ACGAATAATG AGCAGGGAGA GAGGGCATTT  1750
CCCAGAAGGG TATAGCTTGC CTTTAGCATT TGTCCTCTCC CTGGGACTTA  1800
CATCAGCCCG ATAAGCTAGG TATCATTGTA CCAGCCTCAC AGCTGATGAC  1850
ATTGTGTTCA GGGTGGTGGG ATGGTTTCTC CATATTCATA CATGCTTCCA  1900
GAATTCATGT TAAACTCTAT CACATATCCG GAATACACAA GTCTCAGTTC  1950
GAACTGGTTC AAGATCTAGG CTTGGCAACT ACTCTTTCTT TCTAATGAGA  2000
AAGACTGGGG GCCCAGGGCG CTAAAGAGAA TGAATGAGGA AGCTTCTCAG  2050
GCTGTTCAAA TACTGACACT GCCCTGGTTA CTGCCTAGTG ACTTCAGGCT  2100
GGCAATTTTC TCTTCTCTAA CGTCAGAGAA AAAGTTTACT GTCTTGCTCC  2150
TGGGAAGCAT GATGGAAGG  CTTAGCAGCT AAGGGGTACT AAGAGGTAGT  2200
AAGTCATCTC TGTCATGTAA AAGATTTCAC AGGCCATTGA AACATGGGCA  2250
AGACCCAGTG CCTAGAGTCT GCAAGATTGGT CCTAAAGAC  ATCCACCACG  2300
TGTATTGCGA GTGGAAAATA GAAATTCATG TTTGACTCAA GCTTTAGAGA  2350
TTTTGTAATT CTGTGAGCAT TTAAAAATA  TTTCCATATA AACTAAAAAA  2400
ATAAAAACTA TTTCCAAAAA AAAAAAAAAA AAAAACTCGA G           2441
```

(SEQ ID NO: 30). SEQ ID NO: 1 is identical to nucleotides 1-1168 of SEQ ID NO: 30. The TMPRSS2-derived sequence is shown in bold font and the initiation codon and stop codon are shown in bold italics, also as shown in SEQ ID NO: 1. The shaded region, SEQ ID NO: 48, identifies an adenosine-rich area corresponding to nucleotides 1300-1310 of SEQ ID NO: 30. It aligns with the 3' end of AY204742, as shown below:

```
AAAAATAAACA         (SEQ ID NO: 48)
```

-continued
```
AAAAAAAAAA          (SEQ ID NO: 49)
```

The two bolded nucleotides, T1305 and C1309 of SEQ ID NO: 30, both correspond to adenosines in the AY204742 sequence, suggesting that AY204742 may previously have been erroneously considered to possess a polyA tail at this site.

Nucleotides 802-2415 comprise a region specific to ERG8. This region encodes the unique carboxy terminus and also comprises a non-coding 3' region, as shown below:

```
GTACGAAAAC ACCCCTGTGT GATCTCTTCA TTGAGAGACA TCCCAGATGT    50

CCTGCTGAGA TCCGTGCCCT AAGTCACGTG ATACAAAGAG AGCTGATCCC   100

GGAGCTGAAG CCAGTCCCAG ACAGTCTTAT TCTGCCTCTG TTGATTTGGA   150

GACTAAATCC ACTCAAACCA TTTCATTCAA AGACCACACT AAAGGAATTA   200

AGAGCAGATT AGCCCTTTAA CTAGCTTTTC AGAAAGACAG ATGGGCAAAG   250

AAGGCATCCT GGATGCCTGG CAGTTAGGAA TAGGCCGACT TTTGAACTAA   300

CAGAAGGATC TGTCCCTCCT CGGGGAAGA  GCACAAAACA AGGACACTCC   350

CCAGATTCAC AGTGACCGAT TATCAGTATG TCACAAGAAG CCAGTCTTGC   400

AGAGCAGAAG CATGCAACCA GTAGTATTTA CATCTGAATC TTACTGCCTG   450

TCCTCCAAAT GATTTAATTA GGTAATAAAT TTACATGCCA TTCATGCAAA   500

AATAAACATC TATCAAGTGC CCATTAGTGC CAAGCGTGGT GTTAGACTCT   550

GGGAATATAT AGATGAACCA GGCTTCAGTA AGCTTCCTGT CTTCAGAAAG   600

TTTACTTCTT CATTCAGCTT GGTTTGTTCA TTTGCTGAGT GCCTCCTCTG   650
```

```
                                    -continued
TGCCAGCCAC GGATGGTATG ATGGTGAACA AACCGAAATG TTTTGCCTCC   700

AGTTCTAGAT GTTTCAGTAG AGTGACCTAG AGCCAGAGAG ACACATATGT   750

ACACATAAAT GTTTTCCCTA ATGTGATAGA TTTTATGGTA GAGGAACCAC   800

TTCTAGCAAT ACAGGGCGTA GGAGCAGGGG TGGGGAGGAA CTCAATCCCC   850

CATGAAAGGC ATAAAGTTGC TTTCCAGAGG AATGGCCACA TGGCAAAGGG   900

GAATTAGATG TTTGCCAGAC GAATAATGAG CAGGGAGAGA GGGCATTTCC   950

CAGAAGGGTA TAGCTTGCCT TTAGCATTTG TCCTCTCCCT GGGACTTACA  1000

TCAGCCCGAT AAGCTAGGTA TCATTGTACC AGCCTCACAG CTGATGACAT  1050

TGTGTTCAGG GTGGTGGGAT GGTTTCTCCA TATTCATACA TGCTTCCAGA  1100

ATTCATGTTA AACTCTATCA CATATCCGGA ATACACAAGT CTCAGTTCGA  1150

ACTGGTTCAA GATCTAGGCT TGGCAACTAC TCTTTCTTTC TAATGAGAAA  1200

GACTGGGGGC CCAGGGAGCT AAAGAGAATG AATGAGGAAG CTTCTCAGGC  1250

TGTTCAAATA CTGACACTGC CCTGGTTACT GCCTAGTGAC TTCAGGCTGG  1300

CAATTTTCTC TTCTCTAACG TCAGAGAAAA AGTTTACTGT CTTGCTCCTG  1350

GGAAGCATGA TGGAAAGGCT TAGCAGCTAA GGGGTACTAA GAGGTAGTAA  1400

GTCATCTCTG TCATGTAAAA GATTTCACAG GCCATTGAAA CATGGGCAAG  1450

ACCCAGTGCC TAGAGTCTGC AAGATTGGTC CTAAAGACAT CCACCACGTG  1500

TATTGCGAGT GGAAAATAGA AATTCATGTT TGACTCAAGC TTTAGAGATT  1550

TTGTAATTCT GTGAGCATTT AAAAAATATT TCCATATAAA CTAAAAAAAT  1600

AAAAACTATT TCC                                         1613
```

(SEQ ID NO: 46). The ERG8 specific carboxyl terminus of the encoded polypeptide is:

```
GTKTPLCDLF IERHPRCPAE IRALSHVIQR ELIPELKPVP

DSLILPLLIW RLNPLKPFHS KTTLKELRAD
```

(SEQ ID NO: 47).

EPC1 is an ERG isoform that is selectively expressed in cancerous prostate cells. The nucleic acid sequence of EPC1 is:

```
GCAGGAGGCG GAGGCGGAGG CGGAGGGCGA GGGGCGGGGA GCGCCGCCTG    50
GAGCGCGGCA  AAGCCTTA TCAGTTGTGA GTGAGGACCA GTCGTTGTTT   100
GAGTGTGCCT ACGGAACGCC ACACCTGGCT AAGACAGAGA TGACCGCGTC   150
CTCCTCCAGC GACTATGGAC AGACTTCCAA GATGAGCCCA CGCGTCCCTC   200
AGCAGGATTG GCTGTCTCAA CCCCCAGC   GGGTCACCAT CAAAATGGAA   250
TGTAACCCTA GCCAGGTGAA TGGCTCAAGG AACTCTCCTG ATGAATGCAG   300
TGTGGCCAAA GGCGGGAAGA TGGTGGGCAG CCCAGACACC GTTGGGATGA   350
ACTACGGCAG CTACATGGAG GAGAAGCACA   CCACCCCC AAACATGACC   400
ACGAACGAGC GCAGAGTTAT CGTGCCAGCA GATCCTACGC TATGGAGTAC   450
AGACCATGTG CGGCAGTGGC TGGAGTGGGC GGTGAAAGAA TATGGCCTTC   500
CAGACGTCAA CATCTTGTTA TTCCAGAACA TCGA GGGAA GGAACTGTGC   550
AAGATGACCA AGGACGACTT CCAGAGGCTC ACCC CAGCT ACAACGCCGA   600
CATCCTTCTC TCACA  TCC ACTACCTCAG AGAGACTCCT CTTCCACATT   650
TGACTTCAGA TGATGT GAT AAAGCTTAC AAAACT  CC ACGGTTAATG   700
CATGCTAGAA ACACAGGGGG TGCAGCTTTT ATTTTCCCAA ATACTTCAGT   750
ATATCCTGAA GCTACGCAAA GAATTACAAC TAGGCCAGTC TCTTACAGAT   800
AAAACAACAG AACCAGTGCC AGAAAGCAGC CTTCCCTTAC ATGGGCACTT   850
CTGCCAAGCA TATGAGTTCA TTGCCTTGAA GATCAAAGTC AAAGAGAAAT   900
GGAGAGGGTG TTGAAATGAT CAGCGAAAAT TAAATGTAAA ATATATTCTT   950
ATTGGAAGTC TGATGCTCTA TTATCAATAA AGGACACATA GCAAAGATAA  1000
AAAAAAAAAA AAAAAAAA
```

(SEQ ID NO: 3). In the sequence, the TMPRSS2-derived sequence is shown in bold font. Exon junctions are shown in grey boxes. The initiation codon and stop codon are shown in bold italics. The 3' end of the EPC1 transcript is distinct from all known ERG isoforms. This unique sequence is shown in bold font. The amino acid sequence of EPC1 is:

```
MTASSSSDYG QTSKMSPRVP QQDWLSQPPA RVTIKMECNP SQVNGSRNSP    50

DECSVAKGGK MVGSPDTVGM NYGSYMEEKH MPPPNMTTNE RRVIVPADPT   100

LWSTDHVRQW LEWAVKEYGL PDVNILLFQN IDGKELCKMT KDDFQRLTPS   150

YNADILLSHL HYLRETPLPH LTSDDVDKAL QNSPRLMHAR NTGGAAFIFP   200

NTSVYPEATQ RITTRPVSYR
```

(SEQ ID NO: 4). EPC1 comprises additional nucleotides at its 3' end that encode four unique amino acids at the carboxy terminus of the EPC1 protein. These four unique amino acids are underlined in SEQ ID NO: 4. Because EPC1, like ERG8, lacks the coding sequences for the DNA-binding domain, it may also have a dominant negative effect.

EPC2 is also selectively expressed in cancerous prostate cells. The nucleic acid sequence of EPC2 is:

```
ACATCTTGTT ATTCCAGAAC ATCGATGGGA AGGAACTGTG CAAGATGACC    50
AAGGACGACT TCCAGAGGCT CACCCCCAGC TACAACGCCG ACATCCTTCT   100
CTCACATCTC CACTACCTCA GAGAGAGTAA GCTCCCCCTT CCTCCAAGGA   150
TAGATGGCTG TGGCTATGGT TCTTATGACC CGAGCTTCAG AGGGTTCAAC   200
CAGGTGTGTC GACAGCATCC TCCTGCCCTC GCCCAGTTCC CACTGGGGAT   250
CCGAGGGAGC CACATGCTTG GGTCCTGCGA CCAAGAAGAT GGAATGTCAA   300
AGGGGAAAGG AAGCGTTAAC TGGTCACACA TTAGTTAAGT CTCCATGATA   350
CCCCGAATCA AAATAGAATC ATTAAGGCTT CTCTTTCGTA GGAATTAGGG   400
GGATTATTCT CCCTAAAGCT ACATGAAGCC CCACTTTATA TTCTAACCTG   450
AGCACAGAAC AAGGGAAGTT TTCACTTTGT ATCATGTGAT TCGGCTTAAC   500
CTGACAGAAA GGGATGGCAT GTTGGCATGA ATCCAGAATG TTTGCTGCAT   550
GCTTTAATTT CTACAACGTC CAGCATGGTG AGAAGGAAGT AGTGTGACAG   600
ACAGTGAGGT GGATAAATTC TCCTCCATTG CTTTGCCTGG CATCCCAACC   650
ACTTCTTCCC TGAATTAAAG ACGGGCCCCC ATGTAGGTTT TAACATGCTA   700
ACAAGTAGCA GGTTGCTGGA AATAGTTATA AGCTTCCCAT GATGTTAGTG   750
TGGGAGTGGG GGAACGGTTT CTTTCTTTCT TTTTCTTTCT TTTTTTTTTT   800
TTTTTTT
```

(SEQ ID NO: 5). The initiation codon and stop codon are shown in bold italics. An exon junction is shown in the grey box. The unique 3' sequence is shown in bold font. The amino acid sequence of EPC2 is:

```
MTKDDFQRLT PSYNADILLS HLNYLRESKL PLPPRIDGCG YGSYDPSFRG    50

FNQVCRQHPP ALAQFPLGIR GSHMLGSCDQ EDGMSKGKGS VNWSHIS
```

(SEQ ID NO: 6). The unique carboxy terminus of EPC2 is shown in bold font in SEQ ID NO: 6.

The disclosure also describes the activation of a promoter in prostate cancer cells. Activation of this promoter produces transcripts coding for ERG isoforms lacking the N-terminal protein-protein interaction domain of wild type ERG. Therefore, expression products of this promoter sequence in prostate cancer cells appear to act as dominant negative or gain-of-function molecules. The promoter is located within the following sequence from exon 9 of the ERG gene:

```
TCTGTCGCCA GTCTGGAGTG CAGTGGCATG ATCTCAGCTC ACTGCAACCT  50
CCACCTCCCG GATTCAAGCA ATTTTCCTGC CTCAGCCTCC TGAGTAGCTG 100
GGACTACAGG CATGCCCAGC TAATTTTTGT ATTTTTAGTA GAGACGGGGT 150
TTCACCATGT TGGCCAGGAT GGTCTGGATC TCTTGACCTC ATGATCCGCC 200
CACCTCGGCA TCCCAAAGTG TTGGGACTAC AGGCATGAGC CACGGCACCC 250
CGCCTGTATT TGGCTTTTCA CACTTGTCCT TTCTCCCCCA GTCTCTTCCG 300
CCTTGCCCTT CTTTGGTTCT CTCTGTGTAT TGTGAGAAGT CGATGGAGAC 350
ATGCTCTTTG ATTGCTGTTA TAATGGAAGA ATATTTCTTC TCCTCCAGGA 400
ACTCTCCTGA TGAATGCAGT GTGGCCAAAG GCGGGAAGAT GGTGGGCAGC 450
CCAGACACCG TTGGGATGAA CTACGGCAGC TACATGGAGG AGAAGCACAT 500
GCCACCCCCA AACATGACCA GAACGAGCG CAGAGTTATC GTGCCAGCAG 550
GTCAGGTGCC CACAGCTTCA CTGCCCTCGG CAGATCGCAA CTTCCCCAAG 600
GCTAGGCTGA GCCTCAGGGA GCTCTTCTCC CCCACCTGTG GCATTGATCA 650
```

(SEQ ID NO: 7). In the sequence, the most 3' transcription start site is bolded and shown in a grey box. A sequence comprising at least nucleotides 521 to 650 of SEQ ID NO: 7 retain promoter activity.

Diagnostic Compositions and Methods

The ERG isoform nucleic acids, the polypeptides they encode, and antibodies to those polypeptides can be employed in various diagnostic and prognostic applications for prostate cancer because ERG8, EPC1, EPC2, and the transcripts from the prostate cancer-specific promoter are each associated with prostate cancer.

Accordingly, the disclosure provides methods for detecting prostate cancer in a biological sample, comprising combining the biological sample with at least a first and a second oligonucleotide primer under hybridizing conditions, wherein the first oligonucleotide primer contains a sequence that hybridizes to a first sequence in a target sequence from ERG8, EPC1, EPC2, or the transcripts from the prostate cancer-specific promoter and the second oligonucleotide primer contains a sequence that hybridizes to a second sequence in a nucleic acid strand complementary to the target sequence, wherein the first sequence does not overlap with the second sequence; amplifying a plurality of amplification products when the target sequence is present in the biological sample by adding at least one polymerase activity to the biological sample containing the first and second oligonucleotide primers; immobilizing the plurality of amplification products on a solid support; combining an oligonucleotide probe with the immobilized plurality of amplification products to thereby permit the probe to hybridize to at least one immobilized amplification product; and detecting whether a signal results from hybridization between the oligonucleotide probe and at least one amplification product, wherein detection of the signal indicates the expression of ERG8, EPC1, EPC2, or the transcripts from the prostate cancer-specific promoter and the presence of prostate cancer in the biological sample. Detecting a signal resulting from hybridization between the oligonucleotide probe and the at least one amplification product can be used to diagnose or prognose prostate cancer.

In some embodiments in which the ERG isoform is fused to TMPRSS2, the first oligonucleotide primer contains a sequence that hybridizes to a first sequence in a target sequence from TMPRSS2 and the second oligonucleotide primer contains a sequence that hybridizes to a second sequence in a nucleic acid strand complementary to a target sequence from ERG8, EPC1, EPC2, or the transcripts from the prostate cancer-specific promoter.

Accordingly, the disclosure provides methods for detecting prostate cancer in a biological sample, wherein the target sequence comprises all or part of SEQ ID NO: 1, SEQ ID NO: 3, SEQ ID NO: 5, SEQ ID NO: 7, SEQ ID NO: 30, or SEQ ID NO: 46. In other embodiments, the target sequence comprises nucleotides 75 to 1168 of SEQ ID NO: 1, nucleotides 803 to 1168 of SEQ ID NO: 1, nucleotides 61 to 1019 of SEQ ID NO: 3, nucleotides 788 to 1019 of SEQ ID NO: 3, a nucleic acid molecule comprising SEQ ID NO: 5, nucleotides 127 to 807 of SEQ ID NO: 5, nucleotides 942-1046 of SEQ ID NO: 46, nucleotides 1285-1374 of SEQ ID NO: 46, or nucleotides 1451-1541 of SEQ ID NO: 46.

In some embodiments, the oligonucleotide probe(s), rather than the amplification products, may be optionally fixed to a solid support.

In yet other embodiments, the immobilization and subsequent steps are omitted and the plurality of amplification products are detected by size separation followed by staining with a reagent, such as ethidium bromide, that detects DNA. This embodiment may optionally further comprise photographing the stained DNA to preserve the results. In these embodiments, detection of the amplification products can be used to diagnose or prognose prostate cancer as well.

When detecting ERG isoform expression in a biological sample, the oligonucleotide probe, first oligonucleotide primer, and second oligonucleotide primer, each comprise a nucleic acid sequence that is capable of hybridizing under defined conditions (for example under high stringency hybridization conditions; such as hybridization for 12 hours at 65° C. in 6×SSC followed by a wash in 0.1×SSC at 50° C. for 45 minutes) to a nucleic acid sequence of an ERG isoform. Thus, the oligonucleotide probe, first oligonucleotide primer, and second oligonucleotide primer comprises, for example, a nucleic acid sequence of an ERG isoform, such as SEQ ID NO: 1 (ERG8), SEQ ID NO: 3 (EPC1), SEQ ID NO: 5 (EPC2), SEQ ID NO: 30 (ERG8), SEQ ID NO: 46 (ERG8), a transcript from the prostate cancer-specific promoter (SEQ ID NO: 7), or a nucleic acid molecule comprising a fragment thereof, or a sequence complementary thereto. The oligonucleotide probe, first oligonucleotide primer, or second oligonucleotide primer can be a fragment comprising at least about 15, at least about 20, at least about 30, at least about 40, or at least about 50 contiguous nucleotides of a nucleic acid sequence of ERG8, EPC1, EPC2, or a transcript from the prostate cancer-specific promoter, or a sequence complementary thereto.

In some embodiments, the methods comprise detecting the expression of the ERG8 isoform. In other embodiments, expression of the EPC1 isoform is detected. In yet other embodiments, expression of the EPC2 isoform is detected. While in some embodiments, transcripts from the prostate cancer-specific promoter are detected. In still other embodiments, the methods comprise detecting the ERG8 and EPC1 isoforms in combination, the ERG8 and EPC2 isoforms in combination, the EPC1 and EPC2 isoforms in combination, or the combination of the ERG8, EPC1, and EPC2 isoforms. In other embodiments, the method comprises detecting one or more transcripts from the prostate cancer-specific promoter either alone or in combination with one or more of ERG8, EPC1, or EPC2. In some embodiments, the methods further comprise detecting other prostate cancer-specific markers, such as ERG1, ERG2, PSA, DD3, AMAR, LTF, NPY, SPOCK, CRISP3, PLA2G7, TMEFF2, F5, SMOC, ACPP, TGM4, MSMB, WIF1, OLFM4, PI15, PDGFD, CHGA, CAV1, RLN1, IGFBP7, BGN, FMOD, AGR2, SERPINA3, AZGP1, FAM3B, CD164, or the presence of a TMPRSS-ERG fusion.

Polypeptides encoded by ERG8, EPC1, or EPC2 can also be detected and/or measured in a biological sample. For example, antibodies, optionally labeled, can be used to detect each polypeptide using well known techniques, such as ELISA. The biological sample can be, e.g., prostate tissue, blood, serum, plasma, urine, saliva, or prostatic fluid.

In another aspect, the disclosure provides a method of diagnosing or prognosing prostate cancer, comprising measuring the expression level (e.g. mRNA or polypeptide) of ERG8, EPC1, EPC2 or a transcript from the prostate cancer-specific promoter; and correlating the expression level of an ERG isoform with the presence of prostate cancer or a higher predisposition to develop prostate cancer in the subject.

The skilled artisan will understand how to correlate expression levels or patterns of ERG8, EPC1, EPC2, or a transcript from the prostate cancer-specific promoter with the presence of prostate cancer or a higher predisposition to develop prostate cancer. For example, the expression levels can be quantified such that increased or decreased expression levels relative to a control sample or other standardized value or numerical range indicate the presence of prostate cancer or a higher predisposition to develop prostate cancer.

The increased or decreased expression levels may be measured relative to the expression level of ERG8, EPC1, EPC2, or a transcript from the prostate cancer-specific promoter, or the corresponding polypeptide, in normal, matched tissue, such as benign prostate epithelial cells from the same subject. Alternatively, the expression level of ERG8, EPC1, EPC2, or a transcript from the prostate cancer-specific promoter, or the corresponding polypeptide, may be measured relative to the expression of the gene or polypeptide in other noncancerous samples from the subject or in samples obtained from an individual who does not have cancer. Expression of a gene or the corresponding polypeptide may also be normalized by comparing it to the expression of other cancer-specific markers. For example, a prostate specific marker, such as PSA or TMPRSS2-ERG, can be used as a control to compare and/or normalize expression levels of ERG8, EPC1, EPC2, or a transcript from the prostate cancer-specific promoter, or the corresponding polypeptide.

By way of example, the method of diagnosing or prognosing prostate cancer can comprise measuring the expression levels of the ERG8, EPC1, EPC2, or a transcript from the prostate cancer-specific promoter, isoforms, or any combination thereof, and diagnosing or prognosing prostate cancer, where an increased expression level of ERG8, EPC1, or EPC2 of at least 10%, 20%, 30%, 40%, 50%, 60%, 70%, 80%, 90%, 100%, 200%, or more, as compared to the control sample indicates the presence of prostate cancer or a higher predisposition in the subject to develop prostate cancer, or indicates the severity or stage of prostate cancer, such as whether the cancer is a high risk or a moderate risk prostate cancer.

The expression levels of ERG8, EPC1, EPC2, or a transcript from the prostate cancer-specific promoter (e.g., mRNA or polypeptide expression) can be detected according to the methods described herein or using any other known detection methods, including, without limitation, immunohistochemistry, Southern blotting, northern blotting, western blotting, ELISA, and nucleic acid amplification procedures that include but not limited to PCR, transcription-mediated amplification (TMA), nucleic acid sequence-based amplification (NASBA), self-sustained sequence replication (3SR), ligase chain reaction (LCR), strand displacement amplification (SDA), and loop-mediated isothermal amplification (LAMP).

Nucleic acids are also provided for detecting prostate cancer, and one or more of these nucleic acids may optionally be provided as part of a kit. In some embodiments, the nucleic acid is a nucleic acid probe, such as the probes described elsewhere in the disclosure, that hybridizes to a prostate cancer-specific transcript. For example, in one embodiment, the probe is capable of hybridizing to the desired sequence under high stringency hybridization conditions, such as hybridization for 12 hours at 65° C. in 6×SSC followed by a wash in 0.1×SSC at 50° C. for 45 minutes. The probe can include SEQ ID NO: 1, SEQ ID NO: 30, or SEQ ID NO: 46 itself, or a fragment of SEQ ID NO: 1, SEQ ID NO: 30, or SEQ ID NO: 46 comprising at least about 15, 20, 30, 40, 50, 60, 70, 80, 90, 100, 150, or 200 contiguous nucleotides of SEQ ID NO: 1, SEQ ID NO: 30, or SEQ ID NO: 46, or a sequence complementary thereto. In one embodiment, the fragment comprises all or part of nucleotides 75 to 1168 of SEQ ID NO: 1. For example, the fragment may comprise nucleotides 801 to 1168 of SEQ ID NO: 1, or a nucleic acid molecule comprising at least about 15, 20, 30, 40, 50, 60, 70, 80, 90, 100, 150, or 200 contiguous nucleotides of nucleotides 801 to 1168 of SEQ ID NO: 1. Also by way of example, the fragment may comprise nucleotides 942-1046 of SEQ ID NO: 46, nucleotides 1285-1374 of SEQ ID NO: 46, or nucleotides 1451-1541 of SEQ ID NO: 46.

In some embodiments, the probe selectively hybridizes to the ERG8 isoform but does not hybridize to ERG1, ERG2, ERG3, ERG4, ERG5, ERG6, ERG7, ERG9, EPC1, EPC2, a transcript from the prostate cancer-specific promoter, or TMPRSS2 under defined conditions, including, for example, high stringency hybridization conditions. The length of the probe may vary depending, for example, on the hybridization conditions and the percent identify between the target sequence and the probe, and, therefore can be up to about 6, 10, 20, 30, 40, 50, 100, 150, 200, 300, 400, or 500 nucleotides long.

In some embodiments, therefore, the disclosure provides an isolated nucleic acid comprising at least about 15 contiguous nucleotides of nucleotides 801 to 1168 of SEQ ID NO: 1, wherein the nucleic acid is capable of hybridizing to SEQ ID NO: 1, or the complement thereof, under conditions of high stringency but not to ERG1, ERG2, ERG3, ERG4, ERG5, ERG6, ERG7, ERG9, EPC1, EPC2, a transcript from the prostate cancer-specific promoter, or TMPRSS2. In some embodiments, the nucleic acid is up to about 50 nucleotides long. In other embodiments the probe is capable of hybridizing to the desired sequence under conditions of high stringency comprising hybridization for 12 hours at 65° C. in 6×SSC followed by a wash in 0.1×SSC at 50° C. for 45 minutes.

In another embodiment, the probe hybridizes to SEQ ID NO: 3, or to a sequence within nucleotides 61 to 1019 or 788 to 1068 of SEQ ID NO: 3 (EPC1), or to the complement thereof, under defined hybridization conditions. For example, in one embodiment, the probe is capable of hybridizing to the desired sequence under high stringency hybridization conditions, such as, hybridization for 12 hours at 65° C. in 6×SSC followed by a wash in 0.1×SSC at 50° C. for 45 minutes. The probe can include SEQ ID NO: 3 itself, or a fragment of SEQ ID NO: 3 comprising at least about 15, 20, 30, 40, 50, 60, 70, 80, 90, 100, 150, or 200 contiguous nucleotides of SEQ ID NO: 3, or a sequence complementary thereto. In one embodiment, the fragment comprises all or part of nucleotides 61 to 1019 of SEQ ID NO: 3. For example, the fragment may comprise nucleotides 788 to 1019 of SEQ ID NO: 3, or a nucleic acid molecule comprising at least about 15, 20, 30, 40, 50, 60, 70, 80, 90, 100, 150, or 200 contiguous nucleotides of nucleotides 788 to 1019 of SEQ ID NO: 3. In some embodiments, the probe selectively hybridizes to EPC1 but not to ERG1, ERG2, ERG3, ERG4, ERG5, ERG6, ERG7, ERG8, ERG9, EPC2, a transcript from the prostate cancer-specific promoter, or TMPRSS2 under defined conditions, including, for example, high stringency hybridization conditions. The length of the probe may vary depending, for example, on the hybridization conditions and the percent identify between the target sequence and the probe, and, therefore can be up to about 6, 10, 20, 30, 40, 50, 100, 150, 200, 300, 400, or 500 nucleotides long.

In some embodiments, therefore, the disclosure provides an isolated nucleic acid comprising at least about 15 contiguous nucleotides of nucleotides 788 to 1019 of SEQ ID NO: 3, wherein the nucleic acid is capable of hybridizing to SEQ ID NO: 3, or the complement thereof, under conditions of high stringency but not to ERG1, ERG2, ERG3, ERG4, ERG5, ERG6, ERG7, ERG8, ERG9, EPC2, a transcript from the prostate cancer-specific promoter, or TMPRSS2. In some embodiments, the nucleic acid is up to about 50 nucleotides long. In other embodiments the probe is capable of hybridizing to the desired sequence under conditions of high stringency comprising hybridization for 12 hours at 65° C. in 6×SSC followed by a wash in 0.1×SSC at 50° C. for 45 minutes.

In a further embodiment, the probe hybridizes to SEQ ID NO: 5 (EPC2) or to nucleotides 127 to 807 of SEQ ID NO: 5, or to the complement thereof, under defined hybridization conditions. For example, in one embodiment, the probe is capable of hybridizing to the desired sequence under high stringency hybridization conditions, such as, hybridization for 12 hours at 65° C. in 6×SSC followed by a wash in 0.1×SSC at 50° C. for 45 minutes. The probe can include SEQ ID NO: 5 itself, or a fragment of SEQ ID NO: 5 comprising at least about 15, 20, 30, 40, 50, 60, 70, 80, 90, 100, 150, or 200 contiguous nucleotides of SEQ ID NO: 5 or a sequence complementary thereto. In one embodiment, the fragment comprises all or part of nucleotides 127 to 807 of SEQ ID NO: 5. For example, the fragment may comprise nucleotides 127 to 807 of SEQ ID NO: 5, or a nucleic acid molecule comprising at least about 15, 20, 30, 40, 50, 60, 70, 80, 90, 100, 150, or 200 contiguous nucleotides of nucleotides 127 to 807 of SEQ ID NO: 5. In some embodiments, the probe selectively hybridizes to EPC2 but not to ERG1, ERG2, ERG3, ERG4, ERG5, ERG6, ERG7, ERG8, ERG9, EPC1, a transcript from the prostate cancer-specific promoter, or TMPRSS2 under defined conditions, including, for example, high stringency hybridization conditions. The length of the probe may vary depending, for example, on the hybridization conditions and the percent identify between the target sequence and the probe, and, therefore can be up to about 6, 10, 20, 30, 40, 50, 100, 150, 200, 300, 400, or 500 nucleotides long.

In some embodiments, therefore, the disclosure provides an isolated nucleic acid, comprising at least about 15 contiguous nucleotides of nucleotides 127 to 807 of SEQ ID NO: 5, wherein the nucleic acid is capable of hybridizing to SEQ ID NO: 5, or the complement thereof, under conditions of high stringency but not to ERG1, ERG2, ERG3, ERG4, ERG5, ERG6, ERG7, ERG8, ERG9, EPC2, a transcript from the prostate cancer-specific promoter, or TMPRSS2. In some embodiments, the nucleic acid is up to about 50 nucleotides long. In other embodiments the probe is capable of hybridizing to the desired sequence under conditions of high stringency comprising hybridization for 12 hours at 65° C. in 6×SSC followed by a wash in 0.1×SSC at 50° C. for 45 minutes.

In some embodiments, therefore, the disclosure provides an isolated nucleic acid comprising at least about 15 contiguous nucleotides of nucleotides 942-1056, 1285-1374, or 1451-1541 of SEQ ID NO: 46, wherein the nucleic acid is capable of hybridizing to SEQ ID NO: 46, or the complement thereof, under conditions of high stringency but not to ERG1, ERG2, ERG3, ERG4, ERG5, ERG6, ERG7, ERG9, EPC1, EPC2, a transcript from the prostate cancer-specific promoter, or TMPRSS2. In some embodiments, the nucleic acid is up to about 50 nucleotides long. In other embodiments, the probe is capable of hybridizing to the desired sequence under conditions of high stringency comprising hybridization for 12 hours at 65° C. in 6×SSC followed by a wash in 0.1×SSC at 50° C. for 45 minutes.

A nucleic acid probe may be optionally fixed to a solid support.

In other embodiments, the nucleic acid is an oligonucleotide primer. The disclosure provides a number of oligonucleotide primers and primer pairs, such as those described in the examples. In some embodiments, an oligonucleotide primer pair comprise a first oligonucleotide primer and a second oligonucleotide primer, where the first oligonucleotide primer contains a sequence that hybridizes to a first sequence in SEQ ID NO: 1, SEQ ID NO: 30, and/or SEQ ID NO: 46 and the second oligonucleotide primer contains a sequence that hybridizes to a second sequence in a nucleic acid strand complementary to SEQ ID NO: 1, SEQ ID NO: 30, and/or SEQ ID NO: 46, wherein the first sequence does not overlap with the second sequence. The first and second oligonucleotide primers are capable of amplifying a target sequence of interest in ERG8. Thus, in some embodiments the primer pairs amplify a target sequence comprising all or part of nucleotides 75 to 1168 of SEQ ID NO: 1, all or part of nucleotides 801 to 1168 of SEQ ID NO: 1, all or part of nucleotides 942-1046 of SEQ ID NO: 46, all or part of nucleotides 1285-1374 of SEQ ID NO: 46, or all or part of nucleotides 1451-1541 of SEQ ID NO: 46. In other embodiments, the target sequence comprises a nucleic acid molecule within nucleotides 75 to 1168 of SEQ ID NO: 1, nucleotides 801 to 1168 of SEQ ID NO: 1, or nucleotides 942-1046 of SEQ ID NO: 46, nucleotides 1285-1374 of SEQ ID NO: 46, or nucleotides 1451-1541 of SEQ ID NO: 46.

In some embodiments, the primer pair amplifies a target sequence that selectively hybridizes to the ERG8 isoform but does not hybridize to ERG1, ERG2, ERG3, ERG4, ERG5, ERG6, ERG7, ERG9, EPC1, EPC2, a transcript from the prostate cancer-specific promoter, or TMPRSS2 under defined conditions, including, for example, high stringency hybridization conditions, such as, hybridization for 12 hours at 65° C. in 6×SSC followed by a wash in 0.1×SSC at 50° C. for 45 minutes.

In yet other embodiments, an oligonucleotide primer pair comprise a first oligonucleotide primer and a second oligonucleotide primer, where the first oligonucleotide primer contains a sequence that hybridizes to a first sequence in SEQ ID NO: 3 and the second oligonucleotide primer contains a sequence that hybridizes to a second sequence in a nucleic acid strand complementary to SEQ ID NO: 3, wherein the first sequence does not overlap with the second sequence. The first and second oligonucleotide primers are capable of amplifying a target sequence of interest in EPC1. Thus, in some embodiments the primer pairs amplify a target sequence comprising all or part of nucleotides 61 to 1019 of SEQ ID NO: 3 or all or part of nucleotides 788 to 1019 of SEQ ID NO: 3. In other embodiments, the target sequence comprises a nucleic acid molecule within nucleotides 61 to 1019 of SEQ ID NO: 3 or nucleotides 788 to 1019 of SEQ ID NO: 3. In some embodiments, the primer pair amplify a target sequence that selectively hybridizes to the EPC1 isoform but do not hybridize to ERG1, ERG2, ERG3, ERG4, ERG5, ERG6, ERG7, ERG8, ERG9, EPC2, a transcript from the prostate cancer-specific promoter, or TMPRSS2 under defined conditions, including, for example, high stringency hybridization conditions, such as, hybridization for 12 hours at 65° C. in 6×SSC followed by a wash in 0.1×SSC at 50° C. for 45 minutes.

In still other embodiments, an oligonucleotide primer pair comprise a first oligonucleotide primer and a second oligonucleotide primer, where the first oligonucleotide primer contains a sequence that hybridizes to a first sequence in SEQ ID NO: 5 and the second oligonucleotide primer contains a sequence that hybridizes to a second sequence in a nucleic acid strand complementary to SEQ ID NO: 5, wherein the first sequence does not overlap with the second sequence. The first and second oligonucleotide primers are capable of amplifying a target sequence of interest in EPC2. Thus, in some embodiments the primer pairs amplify a target sequence comprising all or part of SEQ ID NO: 5 or all or part of nucleotides 127 to 807 of SEQ ID NO: 5. In other embodiments, the target sequence comprises a nucleic acid molecule within SEQ ID NO: 5 or nucleotides 127 to 807 of SEQ ID NO: 5. In some embodiments, the primer pair amplify a target sequence that selectively hybridizes to the EPC2 isoform but do not hybridize to ERG1, ERG2, ERG3, ERG4, ERG5, ERG6, ERG7, ERG8, ERG9, EPC1, a transcript from the prostate cancer-specific promoter, or TMPRSS2 under defined conditions, including, for example, high stringency hybridization conditions, such as, hybridization for 12 hours at 65° C. in 6×SSC followed by a wash in 0.1×SSC at 50° C. for 45 minutes.

The oligonucleotide primers and primer pairs can be provided in kit form. In some embodiments, the kits comprise a pair of oligonucleotide primers that is capable of amplifying a target sequence of interest in ERG8, such as those discussed elsewhere in the disclosure, a pair of oligonucleotide primers that is capable of amplifying a target sequence of interest in EPC1, such as those discussed elsewhere in the disclosure, and/or a pair of oligonucleotide primers that is capable of amplifying a target sequence of interest in EPC2, such as those discussed elsewhere in the disclosure. In this and other embodiments, it is not necessary for the oligonucleotide primers to all have different sequences. For example, it is possible to amplify target sequences that are specific for each of ERG8, EPC1, EPC2, or a transcript from the prostate cancer-specific promoter, by selecting an oligonucleotide primer that hybridizes to a nucleotide sequence, or complement thereof, that is unique to ERG8, an oligonucleotide primer that hybridizes to a nucleotide sequence, or complement thereof, that is unique to EPC1, an oligonucleotide primer that hybridizes to a nucleotide sequence, or complement thereof, that is unique to EPC2, an oligonucleotide primer that hybridizes to a nucleotide sequence, or complement thereof, that is unique to a transcript from the prostate cancer-specific promoter, and an oligonucleotide primer that hybridizes to a nucleotide sequence, or complement thereof, that is shared by ERG8, EPC1, and EPC2. Thus, it is possible to use only four oligonucleotide primers to selectively amplify target sequences in each of ERG8, EPC1, and EPC2. Other combinations of primers can be selected to amplify, for example, ERG8 and EPC1, ERG8 and EPC2, EPC1 and EPC2, or one of more of those isoforms in combination with a transcript from the prostate cancer-specific promoter.

The disclosure additionally describes diagnostic kits comprising an anti-ERG isoform-specific antibody, for example, an anti-ERG8 antibody, an anti-EPC1 antibody, or anti-EPC2 antibody. In one embodiment, the disclosure provides an anti-EPC1 antibody that binds an epitope comprising amino acids 217 to 220 of SEQ ID NO: 4. In another embodiment, the antibody is an anti-EPC2 antibody that binds an epitope within or comprising amino acids 28 to 97 of SEQ ID NO: 6. In either case, the epitope can be a linear epitope or a conformational epitope. In some embodiments, combinations of antibodies can be included in the kit. For example, a kit can comprise an anti-ERG8 and an anti-EPC1 antibody, an anti-ERG8 and an anti-EPC2 antibody, an anti-EPC1 and an anti-EPC2 antibody, or an anti-ERG8, an anti-EPC1, and an anti-EPC2 antibody. The antibodies can be, optionally, detectably labeled. The antibodies can be used in both diagnostic and prognostic applications, as described for the nucleic acid probes and primers.

The nucleic acids, polypeptides, and antibodies for use in diagnosing and prognosing prostate cancer are generally formulated with a pharmaceutically acceptable carrier. When a nucleic acid, polypeptide, or antibody is part of a kit, an agent that reduces or inhibits the growth of microorganisms, such as sodium azide, can optionally be included in the formulation.

Therapeutic Compositions and Methods

The ERG isoform (e.g., ERG8, EPC1, EPC2, a transcript from the prostate cancer-specific promoter, ERG1, ERG2, or ERG3) nucleic acids, the polypeptides they encode, and antibodies to those polypeptides can be combined with a suitable pharmaceutical carrier. The resulting pharmaceutical compositions can be used in various applications, such as diagnostic applications already described, and also in therapeutic applications. When the application is therapeutic, the compositions comprise a therapeutically effective amount of the nucleic acid, polypeptide, or antibody and a pharmaceutically acceptable carrier or excipient. Such a carrier includes, but is not limited to, saline, buffered saline, dextrose, water, glycerol, ethanol, and combinations thereof. The formulation should suit the mode of administration.

In therapeutic applications, the ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions will be formulated and dosed in a fashion consistent with good medical practice, taking into account the clinical condition of the individual subject, the site of delivery, the method of administration, the scheduling of administration, and other factors known to practitioners. The effective amount of ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions for purposes herein is thus determined by such considerations.

The disclosure also provides pharmaceutical packs or kits comprising one or more containers filled with one or more of the ingredients of the pharmaceutical compositions described. Associated with such container(s) can be a notice in the form prescribed by a governmental agency regulating the manufacture, use or sale of pharmaceuticals or biological products, which notice reflects approval by the agency of manufacture, use or sale for human administration. In addition, the ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions may be employed in conjunction with other therapeutic compounds.

The pharmaceutical compositions may be administered in a convenient manner such as by the oral, topical, intravenous, intraperitoneal, intramuscular, subcutaneous, intranasal, or intradermal routes. The pharmaceutical compositions are administered in an amount which is effective for treating and/or prophylaxis of the specific indication. In general, they are administered in an amount of at least about 10 micrograms/kg body weight and in most cases they will be administered in an amount not in excess of about 8 milligrams/kg body weight per day.

In pharmaceutical dosage forms, the disclosed compositions can be administered in the form of their pharmaceutically acceptable salts, or they can also be used alone or in appropriate association, as well as in combination, with other pharmaceutically active compounds. The subject compositions are formulated in accordance to the mode of potential administration. Administration of the agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid or gaseous forms, such as tablets, capsules, powders, granules, ointments, solutions, suppositories, enemas, injections, inhalants and aerosols. Methods and excipients mentioned elsewhere in the disclosure are merely exemplary and are in no way limiting.

Compositions for oral administration can form solutions, suspensions, tablets, pills, granules, capsules, sustained release formulations, oral rinses, or powders. For oral preparations, the agents, polynucleotides, and polypeptides can be used alone or in combination with appropriate additives, for example, with conventional additives, such as lactose, mannitol, corn starch, or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

The ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions can be formulated into preparations for injection by dissolving, suspending, or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Other formulations for oral or parenteral delivery can also be used, as conventional in the art.

The ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions can also be introduced into tissues or host cells by other routes, such as viral infection, microinjection, or vesicle fusion. For example, expression vectors can be used to introduce nucleic acid compositions into a cell as described herein. Further, jet injection can be used for intramuscular administration (Furth et al., ANAL BIOCHEM 205:365-368 (1992)). The DNA can be coated onto gold microparticles, and delivered intradermally by a particle bombardment device, or "gene gun" as described in the literature (Tang et al., NATURE 356: 152-154 (1992)), where gold microprojectiles are coated with the DNA, then bombarded into skin cells.

In some embodiments, nucleic acids comprising a sequence encoding an ERG isoform (e.g., ERG8, EPC1, EPC2, a transcript from the prostate cancer-specific promoter, ERG1, ERG2, or ERG3) protein or functional derivative thereof, are administered to promote ERG function, by way of gene therapy. Alternatively, nucleic acids comprising an siRNA, shRNA, or antisense of ERG8, EPC1, EPC2, a transcript from the prostate cancer-specific promoter, ERG1, ERG2, or ERG3 sequence are administered to antagonize ERG expression or function. Any of the methods for gene therapy available in the art can be used. For specific protocols, see Morgan, GENE THERAPY PROTOCOLS, $2^{nd}$ ed., Humana Press (2001). For general reviews of the methods of gene therapy, see Goldspiel et al., CLIN PHARMACY 12:488-505 (1993); Wu et al., BIOTHERAPY 3:87-95 (1991); Tolstoshev, ANN REV PHARMACOL TOXICOL 32:573-596 (1993); Mulligan, SCIENCE 260:926-932 (1993); Morgan et al., ANN REV BIOCHEM 62:191-217 (1993); and May, TIBTECH 11(5):155-215 (1993). Methods commonly known in the art of recombinant DNA technology which can be used are described in Ausebel et al., eds., CURRENT PROTOCOLS IN MOLEC BIOL, John Wiley & Sons, NY (2004); and Kriegler GENE TRANSFER AND EXPRESSION, A LABORATORY MANUAL, Stockton Press, NY (1990).

In some embodiments, the therapeutic comprises an ERG isoform, such as ERG8, EPC1, EPC2, a transcript from the prostate cancer-specific promoter, ERG1, ERG2, or ERG3, or an antisense of one or more of these ERG isoforms. The nucleic acid is part of a vector that has a regulatory sequence, such as a promoter, operably linked to the ERG isoform coding region or antisense molecule, said promoter being inducible or constitutive, and, optionally, tissue-specific. In another embodiment, a nucleic acid molecule is used in which an ERG isoform (e.g., ERG8, EPC1, EPC2, a transcript from the prostate cancer-specific promoter, ERG1, ERG2, or ERG3) coding sequence and any other desired sequences are flanked by regions that promote homologous recombination at a desired site in the genome, thus providing for intrachromosomal expression of the ERG isoform (Koller et al., PROC NATL ACAD SCI USA 86:8932-8935 (1989); Zijlstra et al., NATURE 342:435-438 (1989)).

In some embodiments, the nucleic acid to be introduced for purposes of gene therapy comprises an inducible promoter operably linked to the desired nucleic acids, such that expression of the nucleic acid is controllable by the appropriate inducer of transcription.

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286, which is incorporated herein by reference), or by direct injection of naked DNA, or by use of microparticle bombardment (e.g., a gene gun; Biolistic, DuPont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see, e.g., Wu et al., J Biol Chem 262:4429-4432 (1987)). In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell-specific uptake and expression, by targeting a specific receptor (see, e.g., PCT Pubs. WO 92/06180; WO 92/22635; WO92/20316; WO93/14188; WO 93/20221). Alternatively, the nucleic acid can be introduced intracellularly and incorporated within host cell DNA for expression, by homologous recombination (Koller et al., Proc Natl Acad Sci USA 86:8932-8935 (1989); Zijlstra et al., Nature 342:435-438 (1989)).

In some embodiments, a viral vector that contains an ERG isoform (e.g., ERG8, EPC1, EPC2, a transcript from the prostate cancer-specific promoter, ERG1, ERG2, or ERG3) nucleic acid or antisense nucleic acid is used. For example, a retroviral vector can be used. (Miller et al., Meth Enzymol 217:581-599 (1993)). These retroviral vectors have been modified to delete retroviral sequences that are not necessary for packaging of the viral genome and integration into host cell DNA. The ERG isoform (e.g., ERG8, EPC1, EPC2, a transcript from the prostate cancer-specific promoter, ERG1, ERG2, or ERG3) nucleic acid to be used in gene therapy is cloned into the vector, which facilitates delivery of the gene into a patient. More detail about retroviral vectors can be found in Boesen et al., Biotherapy 6:291-302 (1994), which describes the use of a retroviral vector to deliver the MDRL gene to hematopoietic stem cells in order to make the stem cells more resistant to chemotherapy. Other references illustrating the use of retroviral vectors in gene therapy are: Clowes et al., J Clin Invest 93:644-651 (1994); Kiem et al., Blood 83:1467-1473 (1994); Salmons et al., Hum Gene Ther 4:129-141 (1993); and Grossman et al., Curr Opin Gen Devel 3:110-114 (1993).

Other viral vectors that can be used in gene therapy include adenoviruses, which are capable of infecting non-dividing cells. Kozarsky et al., Curr Opin Gen Devel 3:499-503 (1993) present a review of adenovirus-based gene therapy. Bout et al., Hum Gene Ther 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); and Mastrangeli et al., J Clin Invest 91:225-234 (1993). Adeno-associated virus (AAV) has also been proposed for use in gene therapy (Walsh et al., Proc Soc Exp Biol Med 204:289-300 (1993)).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient. In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler et al., Meth Enzymol 217:599-618 (1993); Cohen et al., Meth Enzymol 217:618-644 (1993); Cline, Pharmac Ther 29:69-92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. The resulting recombinant cells can be delivered to a patient by various methods known in the art.

The prostate cancer-specific transcripts encode protein products that are thought to either directly or indirectly contribute to the development of the cancerous cell. Accordingly, methods that destabilize these transcripts can be used to reduce or prevent expression of the encoded protein product, thereby preserving the cell in a non-cancerous state, or reverting the cell to a non-cancerous phenotype. In some embodiments, therefore, nucleic acids corresponding to ERG8, EPC1, EPC2, ERG1, ERG2, ERG3, or isoforms encoded by transcripts initiated from a prostate cancer-specific promoter (e.g., SEQ ID NO: 7), or a fragment thereof (such as a fragment comprising at least nucleotides 521 to 650 of SEQ ID NO: 7), are used to interfere with the production or translation of their corresponding transcript. In some cases, the nucleic acid is the complement of the transcript sequence. In these cases, the nucleic acids are therapeutic because they modulate the function of nucleic acids encoding an ERG isoform, such as ERG8, EPC1, EPC2, ERG1, ERG2, ERG3, or isoforms encoded by transcripts initiated from a prostate cancer-specific promoter, and thereby alter expression of the encoded isoform.

One method of modulating the function of one or more ERG isoforms is via RNA interference, for example, using siRNA or shRNA against the ERG isoform. The siRNA is a short double stranded RNA molecule of about 18-25 nucleotides that comprises a nucleotide sequence complementary to a region of the target. It can be introduced into a target cell or tissue, for example using an expression plasmid, where it interferes with the translation of an ERG isoform, such as ERG8, EPC1, EPC2, ERG1, ERG2, ERG3, or isoforms encoded by transcripts initiated from a prostate cancer-specific promoter, such as SEQ ID NO: 7 (or a fragment thereof). RNA interference techniques can be carried out using known methods as described, for example, in published U.S. Patent Applications 20060058255, 20040192626, 20040181821, and 20030148519, each of which is incorporated by reference.

Antisense compounds are another class of nucleic acid that is provided by the disclosure for use in modulating the function of nucleic acid molecules encoding one or more ERG isoforms, thereby modulating the amount of the ERG isoform(s) that is produced. This is accomplished by providing antisense compounds that hybridize with one or more nucleic acids encoding an ERG isoform to a cell, for example, by using a gene therapy technique. The nucleic acid can be DNA encoding an ERG isoform (e.g., ERG8, EPC1, EPC2, ERG1, ERG2, ERG3, or isoforms encoded by transcripts initiated from a prostate cancer-specific promoter, such as SEQ ID NO: 7), RNA (including pre-mRNA and mRNA) transcribed from such DNA, and can also be cDNA derived from such RNA. The hybridization of an antisense compound with its target nucleic acid interferes with the normal function of the nucleic acid. The interference can act at the level of replication or transcription of the DNA, translocation of the RNA to the site of protein translation, translation of protein from the RNA, splicing of the RNA to yield one or more mRNA species, or catalytic activity that may be engaged in or facilitated by the RNA. The overall effect of such interference with target nucleic acid function is the modulation of the expression of an ERG isoform, such as ERG8, EPC1, EPC2, ERG1, ERG2, ERG3, or isoforms encoded by transcripts initiated from a prostate cancer-specific promoter, such as SEQ ID NO: 7 (or a fragment thereof, such as a fragment comprising at least nucleotides 521 to 650 of SEQ ID NO: 7).

Antisense oligonucleotides are one form of antisense compound. These often comprise from about 8 to about 30 nucleobases (i.e. from about 8 to about 30 linked nucleosides). In some embodiments, the antisense oligonucleotide comprises from about 12 to about 25, from about 15 to about 22, or from about 18 to about 20 nucleobases. Antisense oligonucleotides can also comprise modified backbones or non-natural internucleoside linkages. Modified oligonucleotides that do not have a phosphorus atom in their internucleoside backbone are also considered oligonucleotides. Examples of modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonzites, phosphinates, phosphoramidates including 3'-amino phosphoramidate and aminoalkylphosphoramidates, thionophosphoiamidates, thionoalkylphosphonates, thionoalkylphosphotriesters, boranophosphates having normal 3'-5' linkages, 2'-5' linked analogs of these, and those having inverted polarity wherein the adjacent pairs of nucleoside units are linked 3'-5' to 5'-3' or 2'-5' to 5'-2', and backbones formed by morpholino linkages.

Peptide nucleic acid (PNA) compounds are also antisense compounds. In a PNA compound, however, the sugar-backbone of an oligonucleotide is replaced with an aminoethylglycine backbone. The nucleobases are retained and are bound directly or indirectly to aza nitrogen atoms of the amide portion of the backbone.

Antisense compounds, methods for their production, and their use to interfere with nucleic acid function are well known in the art. For example, U.S. Pat. No. 6,054,316, which is incorporated by reference, describes the production of antisense compounds for nucleic acids encoding Ets-2 and methods of using these antisense compounds. These same methods can be applied to the production of antisense compounds for nucleic acids encoding an ERG isoform, such as ERG8, EPC1, EPC2, ERG1, ERG2, ERG3, or isoforms encoded by transcripts initiated from a prostate cancer-specific promoter, such as SEQ ID NO: 7 (or a fragment thereof, such as a fragment comprising at least nucleotides 521 to 650 of SEQ ID NO: 7).

In addition to therapeutic applications related to inhibition of expression of ERG isoforms (e.g., ERG8, EPC1, EPC2, ERG1, ERG2, ERG3, or isoforms encoded by transcripts initiated from a prostate cancer-specific promoter, such as SEQ ID NO: 7), antisense compounds are also useful in diagnostic and prognostic methods because these compounds hybridize to nucleic acids encoding ERG isoforms, which can be detected using art-recognized techniques, such as conjugation of an enzyme to the antisense compound, radiolabelling of the antisense compound, or any other suitable detection methods. Kits comprising the antisense compound and a means for detecting it in a sample can also be prepared as described for kits comprising oligonucleotide probes generally.

Antisense modulation of ERG isoform expression can be assayed in a variety of ways known in the art. For example, mRNA levels can be quantitated by, e.g., northern blot analysis, competitive polymerase chain reaction (PCR), or real-time PCR (RT-PCR). RNA analysis can be performed on total cellular RNA or poly(A)+ mRNA. Alternatively or in addition, levels of the encoded protein can be quantitated in a variety of ways well known in the art, such as immunoprecipitation, western blot analysis (immunoblotting), ELISA, or fluorescence-activated cell sorting (FACS).

It is also possible to kill or slow the growth of prostate cancer cells by delivering to those cells a cytotoxic or cytostatic gene product expressed under the control of a prostate cancer-specific promoter, such as the promoter sequence set forth in SEQ ID NO: 7. Truncations and variation of the nucleotide sequence set forth in SEQ ID NO: 7 can also be used, so long as they are sufficient to support expression of an operatively linked reporter gene in prostate cancer cells. Examples include promoter sequences comprising at least nucleotides 521 to 650, 404 to 650, or 138 to 650 of SEQ ID NO: 7. Gene therapy can be used to introduce a vector comprising the prostate cancer-specific promoter operably linked to a nucleic acid encoding the cytotoxic or cytostatic protein into a prostate cancer cell. Such gene therapy methods are described herein. When the prostate cancer-specific promoter is used in the gene therapy vector, however, the promoter is only active in the prostate cancer cells so that the cytotoxic or cytostatic protein is only expressed in the prostate cancer cells, irrespective of the cellular range of the gene therapy vector.

There are many different cytotoxic or cytostatic proteins that can be expressed by placing a heterologous gene under the control of a prostate cancer-specific promoter. Examples of such genes include genes encoding bacterial toxins, such as diphtheria toxin, pseudomonas toxin, ricin, cholera toxin, and PE40; tumor suppressor genes, such as APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, and Gene 21 (NPRL2); genes encoding apoptosis-inducing proteins, such as CD95, caspase-3, Bax, Bag-1, CRADD, TSSC3, bax, hid, Bak, MKP-7, PERP, bad, bcl-2, MST1, bbc3, Sax, BIK, BID, and mda7; and genes encoding drug metabolizing enzymes that convert a pro-drug into a cytotoxic product, such as thymidine kinase (from herpes simplex or varicella zoster viruses), cytosine deaminase, nitroreductase, cytochrome p-450 2B1, thymidine phosphorylase, purine nucleoside phosphorylase, alkaline phosphatase, carboxypeptidases A and G2, linamarase, β.-lactamase and xanthine oxidase.

Accordingly, the disclosure provides a method of treating prostate cancer comprising administering to a subject in need thereof an expression vector comprising a polynucleotide encoding a cytotoxic or cytostatic gene product operably linked to a promoter sequence comprising SEQ ID NO: 7 or a fragment of the nucleotide sequence set forth in SEQ ID NO: 7 that is sufficient to support expression of an operatively linked reporter gene in prostate cancer cells, including, for example, a sequence comprising at least nucleotides 521 to 650 of SEQ ID NO: 7. In another embodiment, the disclosure provides a method of reducing the growth of a prostate cancer cell comprising administering to the cell an expression vector comprising a polynucleotide encoding a cytotoxic or cytostatic gene product operably linked to a promoter sequence comprising SEQ ID NO: 7 or a fragment of the nucleotide sequence set forth in SEQ ID NO: 7 that is sufficient to support expression of an operatively linked reporter gene in prostate cancer cells, including, for example, a sequence comprising at least nucleotides 521 to 650 of SEQ ID NO: 7. In either embodiment, the cytotoxic or cytostatic gene product is chosen from bacterial toxins, tumor suppressor gene products, apoptosis-inducing proteins, and drug metabolizing enzymes that convert a pro-drug into a cytotoxic product.

Another way to kill a prostate cancer cell or to inhibit or slow its growth is by modulating the activity of proteins within the cell. For example, an antibody that binds a protein encoded by an ERG isoform can be used to inhibit or stimulate the function of that protein. In some embodiments, the antibody binds an epitope that is present in proteins encoded by more than one ERG isoforms. Other embodiments involve an antibody that binds the protein encoded by a particular ERG isoform, such as ERG8, EPC1, EPC2, ERG1, ERG2, ERG3, or an isoform encoded by a transcript initiated from a prostate cancer-specific promoter, such as SEQ ID NO: 7 (or a fragment thereof, such as a fragment comprising at least nucleotides 521 to 650 of SEQ ID NO: 7). Thus, in one embodiment the disclosure provides an antibody that binds an epitope comprising amino acid residues 217 to 220 of SEQ ID NO: 4. In another embodiment, the antibody binds an epitope within or comprising amino acids 28 to 97 of SEQ ID NO: 6. The antibody or combination of antibodies can be expressed intracellularly using gene therapy, as described herein. In another example, the antibody binds an epitope within or comprising amino acid residues 28 to 97 of SEQ ID NO: 6, and it also binds the protein consisting of SEQ ID NO: 6.

These various antibodies can be produced using techniques known in the art. For example, the protein(s) encoded by one or more ERG isoform (e.g., ERG8, EPC1, EPC2, ERG1, ERG2, ERG3, or an isoform encoded by a transcript initiated from a prostate cancer-specific promoter, such as SEQ ID NO: 7) can be used as an immunogen and then one or more antibodies with the desired specificity and functional properties can be selected. Such antibodies include, but are not limited to, polyclonal antibodies, monoclonal antibodies, chimeric antibodies, single chain antibodies, and antibody fragments. The antibodies may be from mice, rats, rabbits, hamsters, goats, llamas, humans, or other species.

Various procedures known in the art can be used for the production of polyclonal antibodies to one or more epitopes of a secreted protein. Rabbits, mice, rats, goats, llamas, etc. can be immunized with the native protein, a synthetic version of the protein, or a derivative (e.g., fragment) of the protein. Various adjuvants may be used to increase the immunological response, depending on the host species. Examples of adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For the preparation of monoclonal antibodies, any of a number of art-recognized techniques can be utilized. For example, monoclonal antibodies can be produced using the hybridoma technique (e.g., Kohler et al., NATURE 256:495-97 (1975); and as described in Harlow et al., eds., ANTIBODIES: A LABORATORY MANUAL, Cold Spring Harbor Laboratory, (1988); Colligan et al., eds., CURRENT PROTOCOLS IN IMMUNOLOGY, Chpt. 2, John Wiley & Sons, Inc. (2006)). Antibodies can also be produced using recombinant DNA methods (e.g., U.S. Pat. No. 4,816,567) or using phage display antibody libraries (e.g., Clackson et al., NATURE 352: 624-28 (1991); Marks et al., J MOL BIOL 222: 581-97 (1991)). If desired, chimeric antibodies can be produced using methods known in the art (e.g., Morrison et al., PROC NATL ACAD SCI USA 81:6851-55 (1994); Neuberger et al., NATURE 312:604-08 (1984); Takeda et al., NATURE 314:452-54 (1985)). Single chain antibodies can also be produced (e.g., U.S. Pat. No. 4,946,778). Human antibodies can be prepared using human hybridomas (Cote et al., PROC NATL ACAD SCI USA 80:2026-30 (1983)), by transforming human B cells with EBV virus in vitro (Cole et al., MONOCLONAL ANTIBODIES AND CANCER THERAPY, Alan R. Liss, pp. 77-96 (1985)), or by preparing hybridomas from animals transgenic for one or more human immunoglobulin genes (e.g., U.S. Pat. No. 5,939,598). A monoclonal antibody can be readily expressed using its encoding DNA sequence(s), and methods for such expression, including gene therapy methods, are well known in the art.

Antibody fragments can also be generated using known techniques. Fragments include but are not limited to F(ab')$_2$ fragments, which can be produced by pepsin digestion of the antibody molecule; Fab' fragments, which can be generated by reducing the disulfide bridges of the F(ab')$_2$ fragment; Fab fragments, which can be generated by treating the antibody molecule with papain and a reducing agent; and Fv fragments, including single chain Fv (scFv) fragments.

Following the production of antibodies by, for example, hybridoma technology, screening for the desired antibody can be accomplished by techniques known in the art, e.g., ELISA, and involve no more than routine techniques (e.g., Harlow et al., eds., ANTIBODIES: A LABORATORY MANUAL, Cold Spring Harbor Laboratory, (1988); Colligan et al., eds., CURRENT PROTOCOLS IN IMMUNOLOGY, Chpt. 2, John Wiley & Sons, Inc., 2006). Thus, an antibody can be selected that binds a linear epitope or a conformational epitope. An antibody also can be selected for the property of binding both to a polypeptide fragment of a larger protein, and to the intact (e.g., full length or wild-type) protein.

When it is necessary to produce an antibody to a protein encoded by an ERG isoform (e.g., ERG8, EPC1, EPC2, ERG1, ERG2, ERG3, or an isoform encoded by a transcript initiated from a prostate cancer-specific promoter, such as SEQ ID NO: 7), the protein, its fragment, or other derivative, can be produced using standard techniques. Methods of manipulating nucleic acids to express proteins are well known in the art, and include those described in MOLEC CLONING, A LABORATORY MANUAL (2nd Ed., Sambrook, Fritsch and Maniatis, Cold Spring Harbor) and CURRENT PROTOCOLS IN MOLEC BIOL (eds. Ausubel, Brent, Kingston, More, Feidman, Smith and Stuhl, Greene Publ. Assoc., Wiley-Interscience, N.Y., N.Y., (1992)).

Generally, in order to express the protein encoded by an ERG isoform (e.g., ERG8, EPC1, EPC2, ERG1, ERG2, ERG3, or an isoform encoded by a transcript initiated from a prostate cancer-specific promoter, such as SEQ ID NO: 7), a suitable cell line is transformed with a DNA sequence encoding that protein under the control of known regulatory sequences. The transformed host cells are cultured and the protein recovered and isolated from the culture medium. The isolated expressed proteins are substantially free from other proteins with which they are co-produced as well as from other contaminants. Suitable cells or cell lines may be mammalian cells, such as Chinese hamster ovary cells (CHO), the monkey kidney COS-1 cell line, or mammalian CV-1 cells. The selection of suitable mammalian host cells and methods for transformation, culturing, amplification, screening, product production and purification are known in the art. (See, e.g., Gething and Sambrook, NATURE 293:620-625 (1981); Kaufman et al., MOL CELL BIOL 5(7): 1750-1759 (1985); Howley et al., U.S. Pat. No. 4,419,446.))

Bacterial cells may also be used as suitable hosts for expression of the secreted proteins. For example, the various strains of *E. coli* (e.g., HB101, MC1061) are well-known as host cells in the field of biotechnology. Various strains of *B. subtilis, Pseudomonas*, other bacilli and the like may also be used. For expression of a protein in bacterial cells, DNA encoding the propeptide is generally not necessary.

Many strains of yeast cells known to those skilled in the art may also be available as host cells for expression of the secreted protein biomarkers. Additionally, where desired, insect cells may be utilized as host cells in the method of the present invention. See, e.g., Miller et al., GENETIC ENGINEERING 8:277-298, Plenum Press (1986).

In some embodiments, the protein encoded by an ERG isoform (e.g., ERG8, EPC1, EPC2, ERG1, ERG2, ERG3, or an isoform encoded by a transcript initiated from a prostate cancer-specific promoter, such as SEQ ID NO: 7) is expressed using a vector that contains a full length DNA sequence encoding the protein and appropriate expression control sequences. Expression control sequences for such vectors are known to those skilled in the art and may be selected depending upon the host cells. Such selection is routine. In other embodiments, the secreted protein biomarker is expressed as a fusion protein comprising the protein sequence of the biomarker and, for example, a tag to stabilize the resulting fusion protein or to simplify purification of the secreted protein biomarker. Such tags are known in the art. Representative examples include sequences which encode a series of histidine residues, the epitope tag FLAG, the Herpes simplex glycoprotein D, beta-galactosidase, maltose binding protein, streptavidin tag or glutathione S-transferase.

In some embodiments, therefore, it is desirable that protein expression of ERG8, EPC1, EPC2, ERG1, ERG2, ERG3, or an isoform encoded by a transcript initiated from a prostate cancer-specific promoter, such as SEQ ID NO: 7, is entirely by an in vitro method. Of course, as already discussed, in other embodiments it is desirable that the protein expression occurs in vivo.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Moreover, advantages described in the body of the specification, if not included in the claims, are not per se limitations to the claimed invention.

It is to be understood that both the foregoing general description and the following detailed description are exemplary and explanatory only and are not restrictive of the invention, as claimed. Moreover, it must be understood that the invention is not limited to the particular embodiments described, as such may, of course, vary. Further, the terminology used to describe particular embodiments is not intended to be limiting, since the scope of the present invention will be limited only by its claims. The claims do not encompass embodiments in the public domain.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference in their entireties.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

The specification is most thoroughly understood in light of the references cited herein. Each of these references is hereby incorporated by the reference in its entirety.

ERG Isoform Identification and Expression in Prostate Cancer Tissue and Cell Lines Example 1

Identification of ERG8

ERG1 is the most commonly overexpressed proto-oncogene in malignant prostatic tissue. (Petrovics et al., ONCOGENE 24: 3847-52 (2005).) This overexpression may be due to the fusion of the TMPRSS2 gene with the ERG gene. (Tomlins et al., SCIENCE 310:644-48 (2005).) Alternative splicing generates multiple ERG isoforms. (Owczarek et al., GENE 324:65-

77 (2004).) Thus, it is possible that other isoforms of ERG are also overexpressed, or are selectively expressed, in prostate cancer.

In an initial experiment, we sought to detect the ERG8 isoform in cDNA derived from laser microdissected (LCM) prostate tumor cells. The cDNA was amplified using a primer pair from the genomic sequence of exon 1 of the TMPRSS2 gene (primer p2178: 5'-TAGGCGCGAGCTAAGCAGGAG-3'-SEQ ID NO: 8) and from the ERG coding sequence (primer p2220: 5'-CCAGGATGCCTTCTTTGCCCATC-3'-SEQ ID NO: 9). The TMPRSS2 gene is often fused to the ERG gene in prostate cancer. The p2718 primer corresponds to nucleotides 1 to 21 of SEQ ID NO: 1, while p2220 corresponds to the reverse complement of nucleotides 1042 to 1062 of SEQ ID NO: 1. This primer pair resulted in a PCR product and sequencing confirmed it was ERG8.

ERG8 cDNA can also be amplified using primer pairs directed to ERG8 specific regions of SEQ ID NO: 30 and SEQ ID NO: 46. For example, the primer pair

```
                                    (SEQ ID NO: 35)
     Mid-E8N-F:  5'-GGCATTTCCCAGAAGGGTAT-3'

(SEQ ID NO: 36)
     Mid-E8N-R:  5'-CATCAGCTGTGAGGCTGGTA-3'
``` amplifies nucleotides 1744-1848 of SEQ ID NO: 30 and nucleotides 942-1056 of SEQ ID NO: 46. The primer pair

```
                                    (SEQ ID NO: 37)
     Down-E8N-F:  5'-AGTGACTTCAGGCTGGCAAT-3'

(SEQ ID NO: 38)
     Down-E8N-R:  5'-GCTAAGCCTTTCCATCATGC-3'
``` amplifies nucleotides 2087-2176 of SEQ ID NO: 30 and nucleotides 1285-1374 of SEQ ID NO: 46. The primer pair

```
                                    (SEQ ID NO: 39)
     PoA-E8N-F:  5'-ACCCAGTGCCTAGAGTCTGC-3'

(SEQ ID NO: 40)
     PoA-E8N-R:  5'-AAGCTTGAGTCAAACATGAATTTCT-3'
``` amplifies nucleotides 2253-2343 of SEQ ID NO: 30 and nucleotides 1451-1541 of SEQ ID NO: 46.

The novel full-length ERG8 cDNA of the invention was derived from total RNA isolated from the prostate tissue of a prostate cancer patient. ERG and TMPRSS2 positive cDNA clones were amplified from the CPDR human prostate cancer Lambda ZAP phage cDNA library. To amplify the clones, 12 μl of 2×Pful enzyme/buffer mixture (Stratagene, La Jolla, Calif.) was combined with 7 μl of HPLC-grade water, 2 μl (5 pmol) T3 primer, 2 μl (5 pmol) T7 primer (both primers from Lofstrand Labs, Bendigo, Australia), and 1 μl ERG-positive Lambda phage clones identified from the library. The reaction conditions were the following: 35 cycles at 94° C. for 1 min, 50° C. for 1 min, and 72° C. for 4 min. The thermal cycles were followed by a 7 min incubation at 72° C. and storage at 4° C. The PCR product of this reaction was purified using Performa Spin Columns-33617 (Edge Biosystems, Gaithersburg, Md.).

Nucleotide sequencing was performed by primer extension using the BigDye Sequencing method (Applied Biosystems, Foster City, Calif.). Four μl of BigDye Terminator, 2 μl of 5× Sequencing Buffer, 2 μl (5 pmol) of T7 sequencing primer, 2 μl of the PCR product (the template), and 10 μl of water were added into a total reaction volume of 20 μl. The mixture was incubated at 96° C. for 60 sec, followed by 25 cycles of 96° C. for 10 sec, 50° C. for 5 sec and 60° C. for 4 min. The DNA sequencing reaction mixture was then analyzed on an ABI 3700 Sequence Analyzer. The observed DNA sequences were compared to NCBI databases searching for matches to cDNA sequences and expressed sequence tags (EST). The analysis revealed a 100% match in the overlapping region of the identified clone with the NCBI AY204742 ERG8 cDNA.

The sequence was confirmed with the following internal primers:

```
5'-GAGCGCCGCCTGGAGCGCGGCAG-3'        (SEQ ID NO: 31)

5'-TTCAGAAAGACAGATGGGC-3'            (SEQ ID NO: 32)

5'-CACGGATGGTATGATGGTG-3'            (SEQ ID NO: 33)
```

The results of the sequencing demonstrated that the DNA sequences of the identified prostate cancer cDNA clones extend beyond the 3' end of the AY204742 ERG8 sequence. The primer

```
5'-AGCAATACAGGGCGTAGGAG-3'           (SEQ ID NO: 34)
``` was designed to cover the 3' end of the cDNA sequences, reaching the Lambda ZAP polycloning sequences.

The entire ERG8 nucleotide sequence is shown as SEQ ID NO: 30 in FIG. 1. It corresponds to nucleotides 150-1460 of NCBI Accession No. AY204742, with the exception that the adenosine residues identified at nucleotide positions 1455 and 1459 in AY204742, are identified herein as thymidine at position 1455 and cytosine at position 1459. The ERG8 sequence of SEQ ID NO: 30 comprises a 20-mer polyA tail at nucleotides 2416-2435 (FIG. 1).

Example 2

ERG8 is Selectively Expressed in Prostate Cancer Tissue

We then undertook a more thorough examination of the expression ratios of the ERG1, ERG2, ERG3, and ERG8 isoforms in normal prostate cells and in the prostate cancer-derived cell line VCaP (American Type Culture Collection ("ATCC"), Rockville, Md.). We isolated mRNA from normal prostate of 11 individuals and from prostate cancer-derived VCaP cells, respectively. After converting the mRNA to cDNA, we assessed ERG isoform ratios by comparing the intensities of isoform-specific PCR products in a semi-quantitative multiplex PCR approach. FIG. 2 presents the results of the multiplex PCR analysis. The ERG primers used for the PCR were as follows: p2192 (exon 9): 5'-ACCGTTGGGAT-GAACTACGGCA-3' (SEQ ID NO: 10, which corresponds to nucleotides 352 to 373 of SEQ ID NO: 1); p2220: (ERG8 specific): 5'-CCAGGATGCCTTCTTTGCCCATC-3' (SEQ ID NO: 11, which corresponds to the reverse complement of nucleotides 1042 to 1064 of SEQ ID NO: 1); p2207: (exon 16): 5'-CCCTCCCAAGAGTCTTTGGATCTC-3 (SEQ ID NO: 12); p2197: (exon 15): 5'-CCTGGATTTGCAAGGCG-GCTACT-3' (SEQ ID NO: 13); and p2198: (exon 11): 5'-CTCTCCACGGTTAATGCATGCTAG-3' (SEQ ID NO: 14, which corresponds to nucleotides 699 to 722 of SEQ ID NO: 1).

Primer pair p2192-p2220 results in a 713 bp PCR product when ERG8 is present. The combination of primers p2192 and p2207 amplifies ~1300 bp products representing ERG isoforms 1, 2 and 3. When p2192 (Exon 9) is paired with primer p2197 (Exon 15), that primer combination amplifies one or more of ERG isoforms 1, 2 and 3. Primer pair p2198-p2220 is also specific to the ERG8 isoform, and this primer pair amplifies a 366 bp PCR product when ERG8 is present. The combination of p2198 (Exon 11) and p2207 (Exon 16) results in a 959 bp product detecting ERG isoforms 1, 2 and 3, while the p2198-p2197 combination yields products of 279 bp (isoform 3) and 207 bp (isoforms 1 and 2).

In FIG. 2, the normal prostate samples are labeled "NP", while samples using the VCaP cells are labeled "VC". ERG8 is the predominant isoform detected in VCaP cells (FIG. 2, right photograph, upper arrow). It is also present at higher levels than ERG1 and ERG2 in normal prostate, but its level in normal prostate is comparable to that of ERG3.

Figure 3:
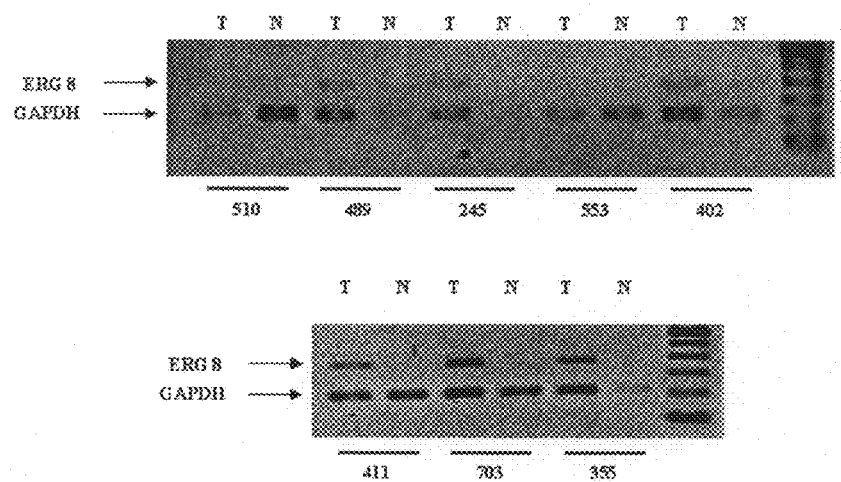
FIG. 3 shows the PCR amplification results for ERG8 transcript expression in tumor cells (T) and benign epithelial cells (N) from eight patients.

We have also assayed the expression of ERG8 transcripts in RNA specimens extracted from laser microdissected (LCM) tumor and benign epithelial cells of 14 individual prostate cancer patients. Primers specifically recognizing the ERG8 isoform (p2198-p2220) were used together with GAPDH primers as internal controls in the same RT-PCR reaction tubes. FIG. 3 shows a photograph of a PCR gel with data for eight of the patients. Tumor cell samples are labeled "T", while the benign epithelial cell samples from each patient are labeled "N". ERG8 expression was detected in the tumor cell samples of 11 of the 14 prostate cancer patients tested. We did not detect ERG8 expression in the benign cells of any patient in this cohort. Thus, ERG8 isoform detection indicates the presence of cells with a cancerous phenotype. In FIG. 3, the level of ERG8 is below the detection limit in the normal samples, which include only epithelial cells. The difference between ERG8 detection in FIG. 2 and FIG. 3, therefore, can be explained by the presence of the other cell types (e.g., stroma and endothelial cells) included in the pooled prostate tissue used for the analysis in FIG. 2.

Interestingly, the ERG8 transcript (SEQ ID NO: 1, SEQ ID NO: 30, and SEQ ID NO: 46) is a fusion between TMPRSS2 and ERG8. The open reading frame, however, is entirely encoded by the ERG8 sequence (nucleotides 75 to 1168 of SEQ ID NO: 1 and SEQ ID NO: 30). The encoded protein (SEQ ID NO: 2), therefore, does not contain any amino acid sequences from TMPRSS2.

Cancer cells gain growth advantage by activating cell growth promoting genes and by silencing inhibitory genes of cell proliferation. Certain genes in these cell growth or proliferation pathways may produce alternative transcript that counteract the function of natural transcriptional products. In the case of ERG8, the encoded protein product lacks the DNA binding domain of, for example, ERG1 and ERG2, but it retains the entire protein-protein interaction domain. Overexpression of ERG8 in the context of prostate cancer, therefore, likely results in the functional nullification of protein interaction partners of ERG1 and ERG2, resulting in a dominant negative effect. ERG8 could also represent an oncogenic "gain of function" isoform.

The finding that ERG8 is selectively expressed in prostate cancer cells provides a powerful therapeutic option, as this oncogenic ERG8 product can be inhibited by selective targeting through its distinct 3' sequences. This selective targeting for cancer therapy can be accomplished using siRNA, shRNA, and other nucleic acid-based products capable of targeting the ERG8-specific sequence. At the protein level, antibodies and therapeutic agents such as small inhibitory peptides can be used to inhibit the activity of the protein produced by ERG8 or to target that protein for degradation. Moreover, ERG8 can differentiate tumor cells from normal epithelial cells in prostate specimens. Accordingly, detection of ERG8 using, for example, amplification primers or hybridization-based methods, can also be used to diagnose and prognose prostate cancer.

Example 3

EPC1 and EPC2 are Newly Identified Transcripts that are Selectively Expressed in Prostate Cancer Tissue To identify tumor specific ERG transcripts, we pooled prostate tumor tissue samples from six patients and extracted total RNA. Polyadenylated RNA (mRNA) was then isolated, converted into cDNA, and packaged into the Lambda Zap express system (Stratagene) to obtain a bacteriophage library. We screened phage plaques by hybridization of radioactively labeled ERG2 probes. The ERG2 sequence includes exons used by all other ERG isoforms; accordingly, it can be used as a general ERG probe. Hybridization was performed with $1 \times 10^6$ cpm $^{32}$P-radiolabelled human ERG2 cDNA/ml hybridization solution at 65° C. for overnight. Following hybridization, the membranes were washed sequentially with 2×SSC supplemented with 0.1% SDS, then 0.2×SSC supplemented with 0.1% SDS, at 65° C. Before we isolated DNA for sequencing, we subjected hybridization positive clones to two more rounds of plaque screening to obtain single plaques.

Two clones yielded novel ERG isoform transcripts. Each clone has a unique 3' sequence. Because these ERG transcripts have only been observed in prostate cancer tissue, we called the clones "EPC1" and "EPC2" for ERG Prostate Cancer-Specific Isoform 1 and 2.

The nucleic acid sequence of the EPC1 clone is set forth in SEQ ID NO: 3. This transcript is also a fusion between exons of TMPRSS2 and ERG. The TMPRSS2 derived sequence occurs at the 5' end upstream of the initiation methionine (ATG at position 140 to 142 of SEQ ID NO: 3). The last four carboxy-terminal amino acids of the EPC1 amino acid sequence (SEQ ID NO: 4) are not found in any ERG exon, and they appear to be derived from an ERG intronic sequence. The unique 3' end of EPC1 corresponds to nucleotides 788 to 1019 of SEQ ID NO: 3 and can be used in both nucleic acid (e.g., amplification and hybridization-based) and protein (e.g., antibody-based) detection methods for the detection of cancer cells or precancerous cells in specimens and biofluids.

The nucleic acid sequence of the EPC2 clone is set forth in SEQ ID NO: 5. The amino acid sequence of EPC2 is set forth in SEQ ID NO: 6. The unique 3' sequence corresponds to nucleotides 127 to 807 of SEQ ID NO: 5. The 5' end corresponds to sequences within ERG exon 10, and the sequence appears to continue into the adjacent 3' exon without splicing, resulting in a unique transcript sequence.

We next investigated the expression of EPC1 transcripts in RNA specimens extracted from laser microdissected (LCM) tumor and benign epithelial cells of 14 prostate cancer patients using RT-PCR. We selected primers specifically recognizing the EPC1 isoform (p2301-p2302) and used them together with GAPDH primers (p2135-p2144) as internal controls in the same reaction tubes. The EPC1 primer sequences were: p2302: 5'-CAGAAAGCAGCCTTC-CCTTA-3' (SEQ ID NO: 15, corresponding to nucleotides 820 to 839 of SEQ ID NO: 3); and p2301: 5'-TTGATAATA-GAGCATCAGACTTCCA-3 (SEQ ID NO: 16, corresponding to the reverse complement of nucleotides 953 to 977 of SEQ ID NO: 3).

Figure 4:
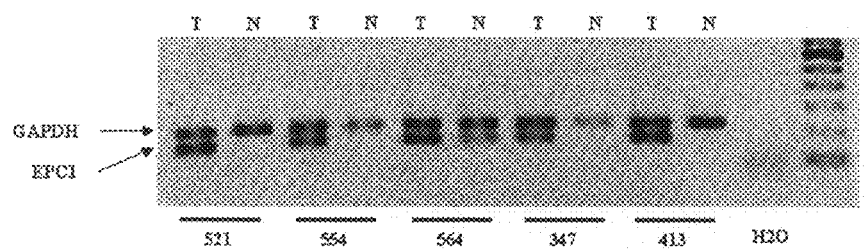
FIG. 4 shows the PCR amplification results for EPC1 transcript expression in tumor cells (T) and benign epithelial cells (N) from five patients.

FIG. 4 shows a photograph of a PCR gel with data for five of the 14 patients. Tumor cell samples are labeled "T," while the benign epithelial cell samples from each patient are labeled "N." EPC1 expression was measured, along with the control gene GAPDH. EPC1 expression detected in the tumor cells of 11 of the 14 prostate cancer patients tested. In seven patients, EPC1 expression could be detected only in their prostate tumor cells, while in four patients, EPC1 expression could be detected in both their tumor and benign epithelial cells. In those instance where EPC1 was detected in both tumor and benign epithelial cells, EPC1 expression was increased in tumor cells relative to benign epithelial cells.

EPC1 and EPC2 are ERG isoforms that are uniquely expressed in cancerous prostate. At the transcript level, the 3' end of each transcript is unique and distinct from all known ERG isoforms. It may be therapeutically beneficial to degrade EPC1 and/or EPC2 mRNA (e.g., using siRNA or shRNA) or to inhibit the EPC1 and/or EPC2 protein by using antibodies raised against each distinct C-terminal region.

Example 4

The ERG8 and EPC1 Isoforms are Abundantly Expressed

Figure 5A:
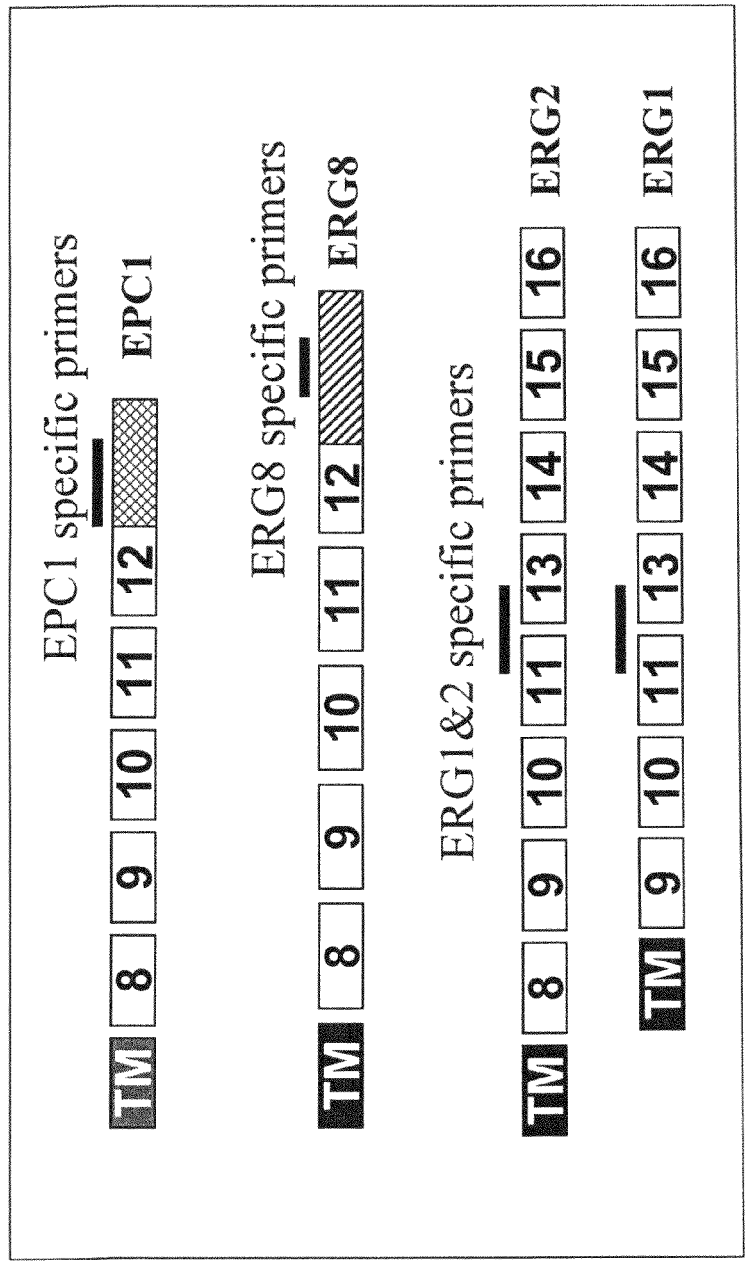
FIG. 5A presents a schematic diagram of the primer positions for EPC1, ERG8, and ERG1&2 specific primers.

In order to compare the relative abundance of ERG8 and EPC1 isoforms to that of ERG1, we prepared samples from prostate cancer-derived VCaP cells as well as from microdissected tumor cells from prostate cancer patients. We then used quantitative PCR to determine the copy numbers using primer pairs specific for EPC1, ERG8, and for a sequence in common between ERG1 and ERG2. The positions of the various primers and the domain structure of the ERG isoforms are shown in FIG. 5A. In the schematic diagram, "TM" denotes TMPRSS2 and the boxes numbered 8-16 correspond to exons, numbered according to Owczarek et al., GENE 324:65-77 (2004)). The ERG8 specific primers and probe were as follows:

```
ERG8 forward primer:
                                    (SEQ ID NO: 17)
TTCAGAAAGACAGATGGGCAAA;

ERG8 reverse primer:
                                    (SEQ ID NO: 18)
GTTCAAAAGTCGGCCTATTCCTAA;

ERG8 probe:
                                    (SEQ ID NO: 19)
AAGGCATCCTGGATGCCTGGCA;

EPC1 forward primer:
                                    (SEQ ID NO: 20)
GCACTTCTGCCAAGCATATGAGT;

EPC1 reverse primer:
                                    (SEQ ID NO: 21)
CGCTGATCATTTCAACACCCT;

EPC1 probe:
                                    (SEQ ID NO: 22)
TGCCTTGAAGATCAAAGTCAAAGAGAAATGGA;

ERG1/2 Ex 11-13 forward primer:
                                    (SEQ ID NO: 23)
TTCAGATGATGTTGATAAAGCCTTACA;

ERG1/2 Ex 11-13 reverse primer:
                                    (SEQ ID NO: 24)
TCCAGGCTGATCTCCTGGG;

ERG 1/2 Ex 11-13 probe:
                                    (SEQ ID NO: 25)
ATGCATGCTAGAAACACAGATTTACCAT.
```

Figure 5B:
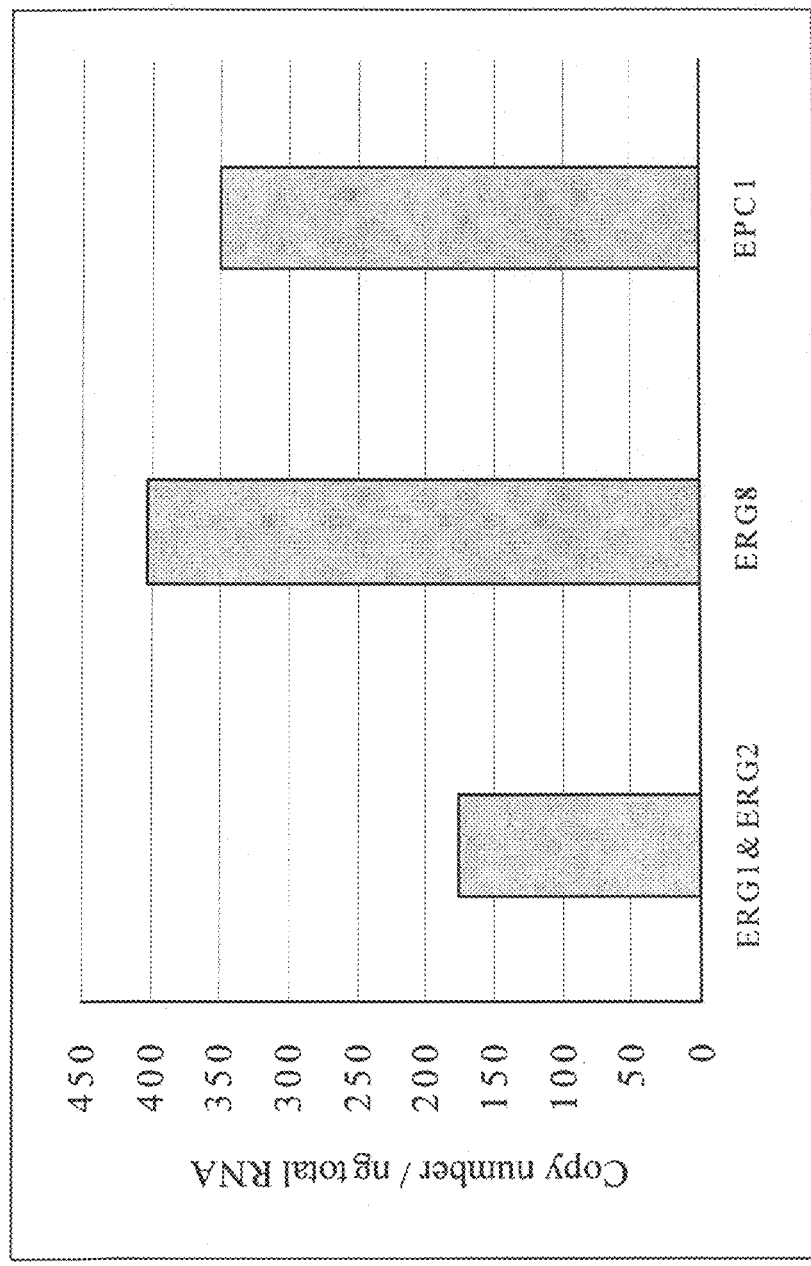
FIG. 5B presents the copy numbers of ERG1&2, ERG8, and EPC1 in VCaP cells.
Figure 5C:
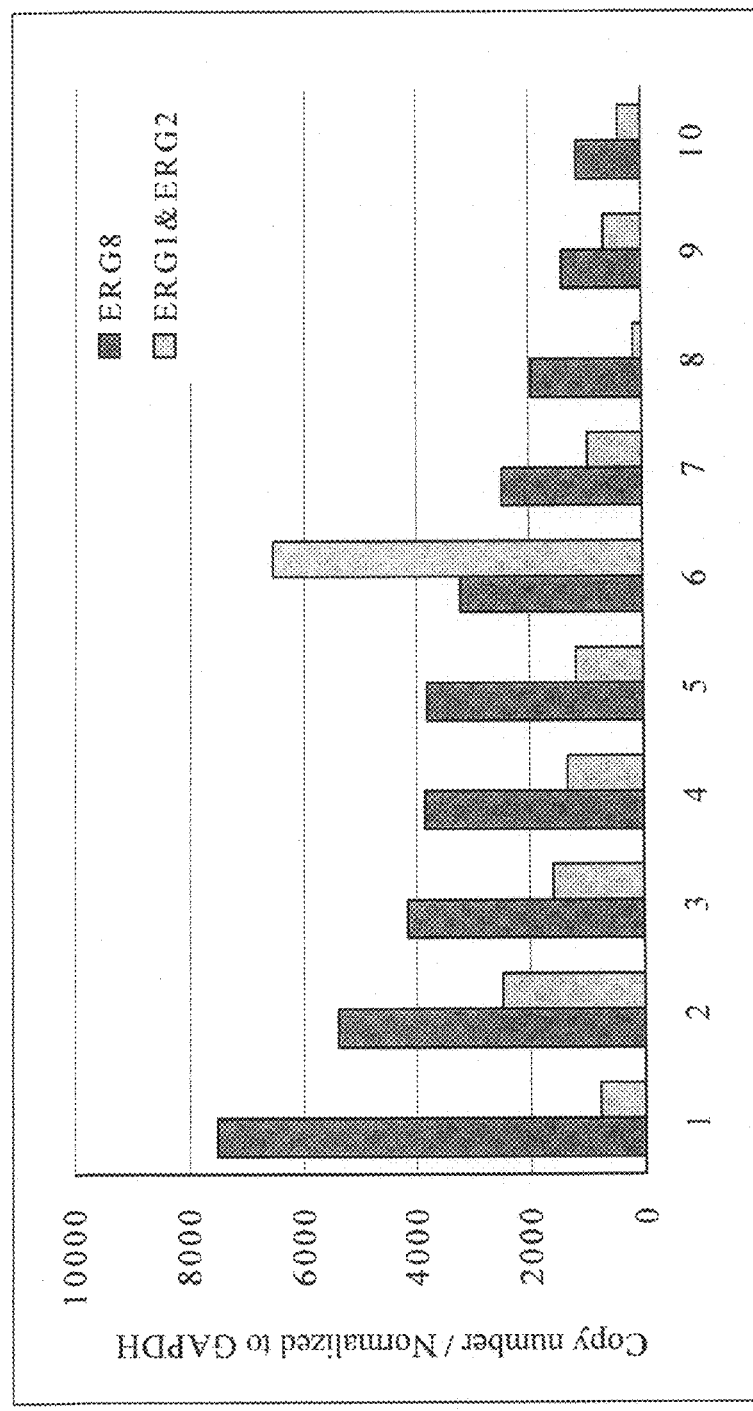
FIG. 5C presents the copy numbers of ERG8 and ERG1&2 using microdissected tumor cells from ten prostate cancer patients.

The number of copies of different ERG isoforms was determined in VCaP cells by TaqMan QRT-PCR using the specific primers and probes shown in FIG. 5A and the results are shown in FIG. 5B. Plasmid constructs comprising a target gene (different ERG isoforms) insert were used to generate standard dilution series in which the copy number of plasmids in the dilution series is known. A formula was derived from the standard curve to correlate the Ct value with the target gene copy number. Using this formula and the standard curve, we calculated the copy numbers of the target genes in the samples. As shown in FIG. 5B, the copy number of both ERG8 and EPC1 is two-fold or more greater than the copy number of the combination of ERG1 and ERG2 in VCaP cells. In addition, microdissected tumor cells of nine of ten prostate cancer patients exhibited a higher copy number for ERG8 than for the ERG1 and ERG2 combination (FIG. 5C). These data indicate that the ERG8 and EPC1 isoforms are abundantly expressed and accordingly provide potential targets in diagnostic and prognostic applications.

Example 5

Combined Detection of ERG8 and EPC1 is Inclusive of all TMPRSS2-ERG Fusions Examined and Results in a Robust Detection System for Prostate Cancer Our finding that ERG8 is overexpressed in prostate cancer and that EPC1 is selectively expressed in prostate cancer tissue can be used to develop a particularly robust diagnostic and prognostic assays because these two genes possess unique 3' ends. The 3' end of an mRNA transcript is relatively resistant to degradation compared to its 5' end, making it possible to detect sequences near the 3' end in clinical samples that might be difficult to detect if they were located toward the 5' end of the sequence. Thus, although one mechanism of over- or selective expression of ERG8, EPC1, and EPC2 may involve a 5' fusion to TMPRSS2, the 3' portion of the ERG8, EPC1, and EPC2 sequences should be more stable and readily detectable in clinical samples than the 5' TMPRSS2 sequence. As a result, detecting the 3' end of ERG8, EPC1, and EPC2 transcripts can reduce false negatives compared to detecting 5' sequences such as the 5' TMPRSS2 sequence in TMPRSS2-ERG fusion transcripts. In addition, biofluids, such as urine, serum, plasma, saliva, and prostatic fluid that are easier and cheaper to obtain but more prone to mRNA degradation, can be used to detect 3' sequences of ERG8, EPC1, and EPC2.

Accordingly, we developed a simple PCR assay that detects aberrant expression due to any type of ERG fusion event. We tested an assay that utilizes three pairs of PCR primers. Namely, we used p2302 (SEQ ID NO: 15) and p2301 (SEQ ID NO: 16) to detect EPC1; p2220 (SEQ ID NO: 11) and p2198 (SEQ ID NO: 14) to detect ERG8; and p2236 and p2237, described in Petrovics et al., ONCOGENE 24:3847-3852 (2005), to detect the 3' UTR of ERG1/2. These primer combinations detect sequences in the 3' end that are retained following any 5' fusion, such as with TMPRSS2, and that are relatively resistant to degradation.

We used these three primer pairs to test the presence or absence of ERG isoforms in LCM selected prostate cancer cells. We divided the samples into two groups, based upon whether we could detect a TMPRSS2-ERG fusion transcript. Table 1 presents the results.

TABLE 1

| FP | ERGfusionA | ERGfusionA | EPC1 | ERG8 | ERG1 | Combined Signal |
|---|---|---|---|---|---|---|
| FP347 | 0.865 | Yes | T | T | | YES |
| FP411 | 8.07 | Yes | T | T | | YES |
| FP413 | 2.52 | Yes | T | T | | YES |
| FP473 | 5.105 | Yes | T | T | T | YES |
| FP480 | 12.005 | Yes | T | no | | YES |
| FP519 | 1.44 | Yes | T | T | | YES |
| FP521 | 1.07 | Yes | T | T | T | YES |
| FP554 | 3.9 | Yes | T | no | | YES |
| FP564 | 2.24 | Yes | T and N | T | | YES |
| FP703 | 2.66 | Yes | T and N | T | | YES |
| FP245 | −3.305 | Yes | T and N | T | | YES |
| FP349 | 1.315 | Yes | T | T | | YES |
| FP355 | 2.12 | Yes | T | T | T | YES |
| FP391 | 2.16 | Yes | T | T | | YES |
| FP402 | 3.595 | Yes | T | T | T (and N) | YES |
| FP430 | 2.77 | Yes | T | T | | YES |
| FP441 | 6.2 | Yes | T and N | no | | YES |
| FP489 | 3.6 | Yes | T | T | | YES |
| FP504 | 5.435 | Yes | | T | | YES |
| FP510 | 4.47 | Yes | T | no | | YES |
| FP553 | 2.94 | Yes | T | no | | YES |
| FP320 | | No | no | no | | |
| FP326 | | No | no | no | | |
| FP346 | | No | no | no | | |
| FP393 | | No | no | no | | |
| FP513 | | No | no | no | | |
| FP535 | | No | no | no | | |
| FP573 | | No | no | no | | |
| FP590 | | No | no | no | | |
| FP598 | | No | no | no | | |
| FP620 | | No | no | no | | |
| FP257 | | No | T and N | no | | YES |
| FP260 | | No | no | no | | |
| FP318 | | No | | no | | |
| FP394 | | No | no | no | | |
| FP446 | | No | no | no | | |
| FP488 | | No, has fusionC | T and N | T | | YES |
| FP491 | | No | no | no | | |
| FP493 | | No | no | | | |
| FP495 | | No | no | no | | |
| FP508 | | No | no | | | |
| FP523 | | No | no | no | | |
| FP575 | | No, has fusionC | T | T | | YES |

In Table 1, the "FP" numbers in the left column are the coded specimen numbers. The first 21 samples presented are those in which we could detect the "A type" TMPRSS2-ERG fusion transcript. ERG fusion A is the most frequent fusion (95% of all fusion transcripts) and involves fusion of the first exon of TMRPSS2 to ERG exon 8. The numeric values in the first column labeled "ERGfusionA" indicate the threshold cycle numbers, normalized to GAPDH, in a quantitative RT-PCR analysis. In 22 samples, we were unable to detect ERG fusion A, but in two samples, FP488 and FP575, we detected ERG fusion C. Fusion "C" is a rare fusion between TMPRSS2 exon 1 and ERG exon 9. In the EPC1, ERG8, and ERG1 columns, "T" indicates detection in tumor cells, "N" indicates detection in normal epithelial cells, and "no" indicates that no signal was detected. The "combined signal" column summarizes the cumulative detection of ERG products ("YES"=expression of any of isoforms EPC1, ERG8, or ERG1).

By using this combined signal approach, we could detect an amplification product in all samples bearing an ERG fusion. In addition, in those samples in which EPC1 was detected but ERG8 was not (e.g., FP480), we still obtained a combined signal. Although we examined ERG1 expression in several samples to validate the assay, the results show that it is not necessary to include ERG1 in the analysis. Instead, the combined signal from EPC1 and ERG8 was all that was needed to detect all fusion events. Accordingly, the combined signal approach can help to minimize false negatives that could arise by looking only at a particular ERG transcript. In addition, we expect that the combined approach can be readily used in clinical samples, such as biofluids, that would be inappropriate for use with primers for the more 5' TMPRSS2-ERG fusion event.

Example 6

A Novel ERG Promoter is Activated in Prostate Cancer

Figure 6:
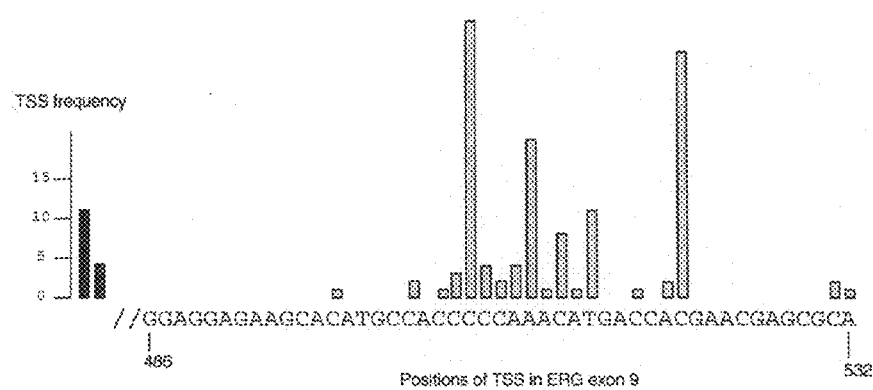
FIG. 6 shows a map of alternative transcription start sites in ERG exon 9 (nucleotides 486 to 532 of SEQ ID NO: 7).

To determine whether there are additional alterations that occur in the ERG locus in prostate cancer, we systematically evaluated transcription initiation sites within the ERG locus using the 5' oligocapping method. This information was used to map cancer-specific ERG alternative transcription start sites. We isolated total RNA from prostate cancer tissues of six patients with verified ERG gene rearrangements, pooled the RNA, then treated it with dephosphatases to degrade non-capped RNA molecules, thereby enriching 5' cap protected mRNA molecules. An RNA oligonucleotide adapter was ligated to substitute the 5' capping structure and cDNA was generated by reverse transcription. We then used the oligocap adaptor and internal primers from ERG exon 10 to amplify 5' ERG sequences. In the first amplification we used ERG primer p2181: 5'-GGCGTTGTAGCTGGGGGTGAG-3' (SEQ ID NO: 26). In the second amplification, we used ERG primer p2268: 5'-CAATGAATTCGTCTGTACTC-CATAGCGTAGGA-3' (SEQ ID NO: 27). The resulting PCR products were cloned into the pUC19 vector, then sequenced. DNA sequences indicating transcription initiation sites from ERG sequences in tumor tissue were matched to the ERG locus and analyzed by generating a score that represented the frequency of individual transcription start sites within the locus. The 5' capping frequency map (CapMap) of ERG gene transcripts is shown in FIG. 6. Of the 152 clones sequenced, 137 of the 5' capping clones had novel, prostate cancer-specific transcription initiation sites within a 23 bp ERG exon 9 region.

In a separate oligocapping experiment, 5' cap sites were assessed in RNA from normal prostates pooled from 11 individuals (AMBION) with a negative prostate cancer diagnosis. In this experiment, we terminated our analysis after 30 clones because the products were homogenous. The results indicated that transcription initiation in normal prostate uniformly occurs in ERG exon 5, in sharp contrast to the multiple exon 9 initiation sites we observed in the tumor specimens. Transcription initiation in ERG exon 5 indicates that ERG isoform 3 is expressed in normal prostate. Also, our results suggest that ERG isoforms 1, 2, 5, 6, 7, 8 and 9 are either not expressed in normal prostate, or they are present only at low levels.

The transcription initiation sites detected in the prostate cancer samples indicated that the central segment of ERG exon 9 is a cancer-specific promoter site. The promoter region is defined as the area between −520 bp and +130 bp relative to the most 3' transcription initiation site detected in the mapping experiment. The promoter sequence is set forth below:

```
TCTGTCGCCA  GTCTGGAGTG  CAGTGGCATG  ATCTCAGCTC  ACTGCAACCT   50
CCACCTCCCG  GATTCAAGCA  ATTTTCCTGC  CTCAGCCTCC  TGAGTAGCTG  100
GGACTACAGG  CATGCCCAGC  TAATTTTTGT  ATTTTTAGTA  GAGACGGGGT  150
TTCACCATGT  TGGCCAGGAT  GGTCTGGATC  TCTTGACCTC  ATGATCCGCC  200
CACCTCGGCA  TCCCAAAGTG  TTGGGACTAC  AGGCATGAGC  CACGGCACCC  250
CGCCTGTATT  TGGCTTTTCA  CACTTGTCCT  TTCTCCCCCA  GTCTCTTCCG  300
CCTTGCCCTT  CTTTGGTTCT  CTCTGTGTAT  TGTGAGAAGT  CGATGGAGAC  350
ATGCTCTTTG  ATTGCTGTTA  TAATGGAAGA  ATATTTCTTC  TCCTCCAGGA  400
ACTCTCCTGA  TGAATGCAGT  GTGGCCAAAG  GCGGGAAGAT  GGTGGGCAGC  450
CCAGACACCG  TTGGGATGAA  CTACGGCAGC  TACATGGAGG  AGAAGCACAT  500
GCCACCCCCA  AACATGACCA  GAACGAGCG   CAGAGTTATC  GTGCCAGCAG  550
GTCAGGTGCC  CACAGCTTCA  CTGCCCTCGG  CAGATCGCAA  CTTCCCCAAG  600
GCTAGGCTGA  GCCTCAGGGA  GCTCTTCTCC  CCCACCTGTG  GCATTGATCA  650
```

(SEQ ID NO: 7). In the sequence, the most 3' transcription start site that is frequently used is bolded and boxed.

Figure 7:
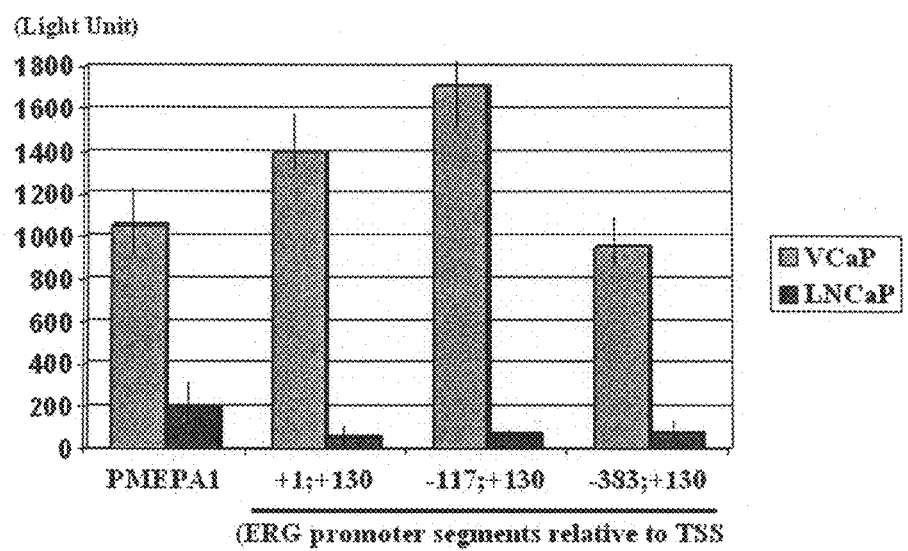
FIG. 7 plots the ability of three segments of the prostate cancer-specific ERG promoter to support expression of a luciferase report construct in the VCaP cell line in comparison to the LNCaP cell line.

The putative TATA-less promoter is predicted at −20; −40 bp from the transcription initiation site. Interestingly, there is also a MED (Multiple Elements of Initiation Downstream) in the +130 region, which may explain the multiple start sites we observed. We have verified that this promoter is functional by operably linking it to the luciferase reporter gene. FIG. 7 demonstrates that the prostate cancer-specific promoter is able to direct expression of luciferase protein in prostate cancer-derived VCaP cells (light grey bars), which contain a TMPRSS2-ERG fusion, but not in LNCaP cells (dark grey bars). A promoter fragment from −117 to +130 (nucleotides 404 to 650 of SEQ ID NO: 7) yielded the greatest expression levels in the luciferase assay, followed by the +1 to +130 fragment (nucleotides 521 to 650 of SEQ ID NO: 7), then the −383 to +130 fragment (nucleotides 138 to 650 of SEQ ID NO: 7).

Activation of a dormant promoter within the ERG gene locus in a cancer specific manner produces transcripts coding for N-terminal deletion mutants. The encoded protein products lack the protein-protein interaction domain of wild type ERG. Therefore, expression products of this dormant promoter may act as dominant negative or gain-of-function molecules. Nucleic acid or protein-based products that manipulate the activity of this promoter can therefore be used for prostate cancer therapy. In addition, the prostate-specific expression of this promoter means that expression vectors in which the promoter is operably linked to a gene encoding a toxin or other inhibitor of cell growth can be used to selectively express the encoded protein in prostate cancer cell.

Example 7

A Regulatory Loop Exists Between ERG and the Androgen Receptor

Gene rearrangements involving the fusion of the androgen receptor-regulated TMPRSS2 gene promoter and ERG occur at a high frequency (~60%) in prostate cancer and are likely to be a direct cause of prostate cell transformation, but the mechanism by which the genomic alteration leads to prostate cancer is thus far unexplained. It is likely that this genomic alteration is responsible for, or at least contributes to, the overexpression of ERG1 in prostate cancer. It is also known that androgen receptor function is central to the growth and differentiation of the normal prostate gland. Further, androgen receptor dysfunction favors the growth and survival of prostate cancer cells and appears to play a role in prostate cancer progression. It is unclear, however, how these alterations interact to result in prostate cancer.

To investigate whether ERG protein contributes to prostate cancer by interfering with androgen receptor signaling, we correlated the expression of TMPRSS2-ERG fusion transcripts with ERG1, androgen receptor (AR), PSA, and the androgen-regulated gene PMEPA1. LTF was also analyzed as a negative control. The results of this analysis are shown in FIG. 8, which compares the quantitative RT-PCR data for the TMPRSS2-ERG fusion to quantitative RT-PCR data obtained by amplifying the 3' untranslated regions of ERG ("ERG1").

Figure 9A:
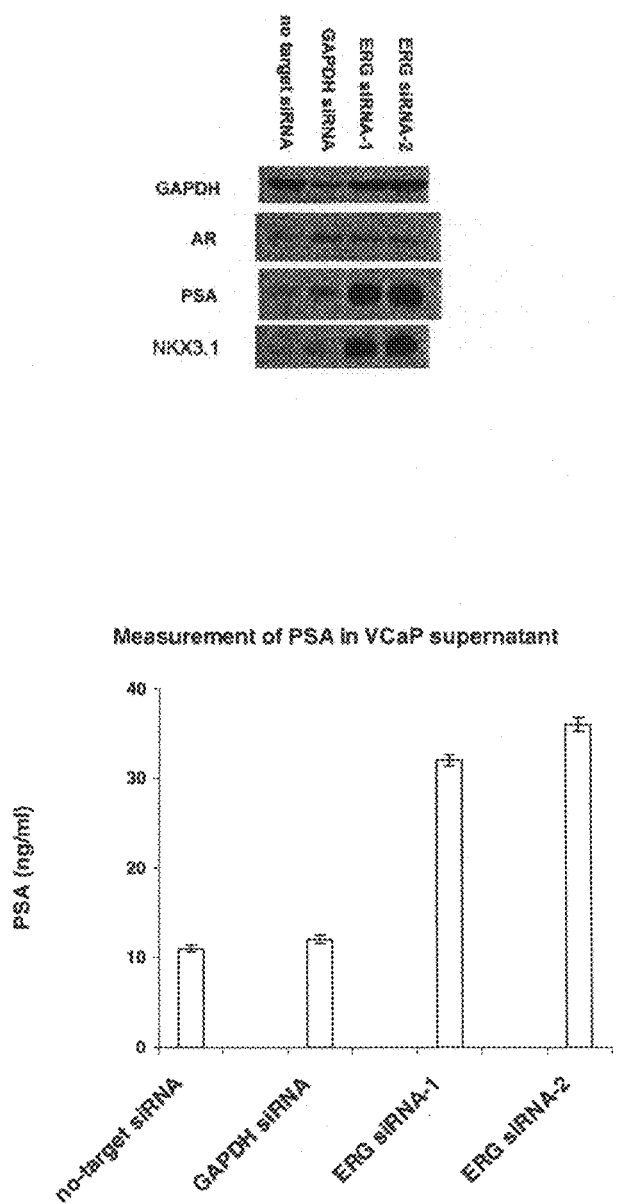
FIG. 9A shows that downregulating ERG increases the expression of androgen receptor responsive genes. The top panel shows a gel demonstrating that inhibition of ERG with two different siRNAs results in increased expression of androgen-inducible PSA and NKX3.1 transcripts. The bottom panel shows that PSA levels also increase in the culture supernatant of VCaP cells when ERG is inhibited with siRNAs.

We next investigated the effect of ERG expression on transcriptional targets of the androgen receptor. We introduced two different ERG siRNAs into the VCaP prostate cancer cell line. The sequence of the siRNAs is: siRNA-1 (p2094): TGATGTTGATAAAGCCTTA (SEQ ID NO: 28), which targets exon 11, and siRNA-2 (p2095): CGACATCCTTCTCT-CACAT (SEQ ID NO: 29), which targets exon 10. VCaP cells possess a TMPRSS2-ERG fusion and overexpress ERG. The results of these experiments are shown in FIG. 9A. Introduction of either siRNA led to the up regulation of NKX3.1 and PSA/KLK3 (FIG. 9A, top panel). The upregulation of PSA/KLK3 could also be detected as increased PSA levels in the VCaP culture supernatant (FIG. 9A, bottom panel).

Figure 9B:
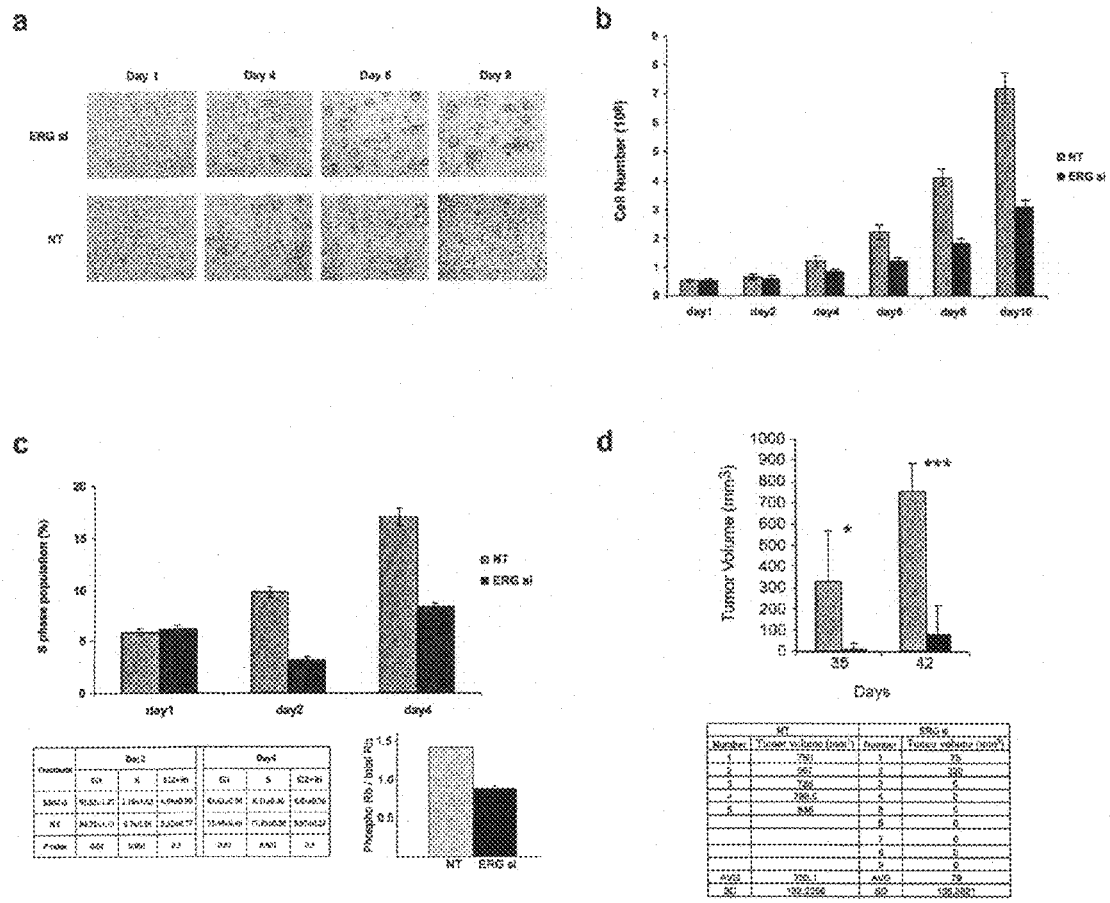
FIG. 9B shows that ERG knockdown inhibits prostate tumor cell growth both in vitro and in an in vivo SCID mouse tumorigenicity assay. The top left panel shows the morphology of VCaP cells transfected with 50 nM ERG siRNA or control ("NT") RNA. The top right panel shows the inhibitory effect of ERG siRNA (dark grey bars) on VCaP cell proliferation, compared to control RNA (light grey bars). The bottom left panel shows a cell cycle analysis demonstrating the inhibitory effect of ERG siRNA (dark grey bars) on the number of cells in S phase, compared to control RNA (light grey bars). The table shows a redistribution of the number of cells in G1, S and G2+M phases as a result of ERG siRNA treatment, measured by FACS analysis. The bottom right panel shows the inhibitory effect of ERG siRNA (dark grey bars) on in vivo tumor volume, compared to control RNA (light grey bars).
Figure 9C:
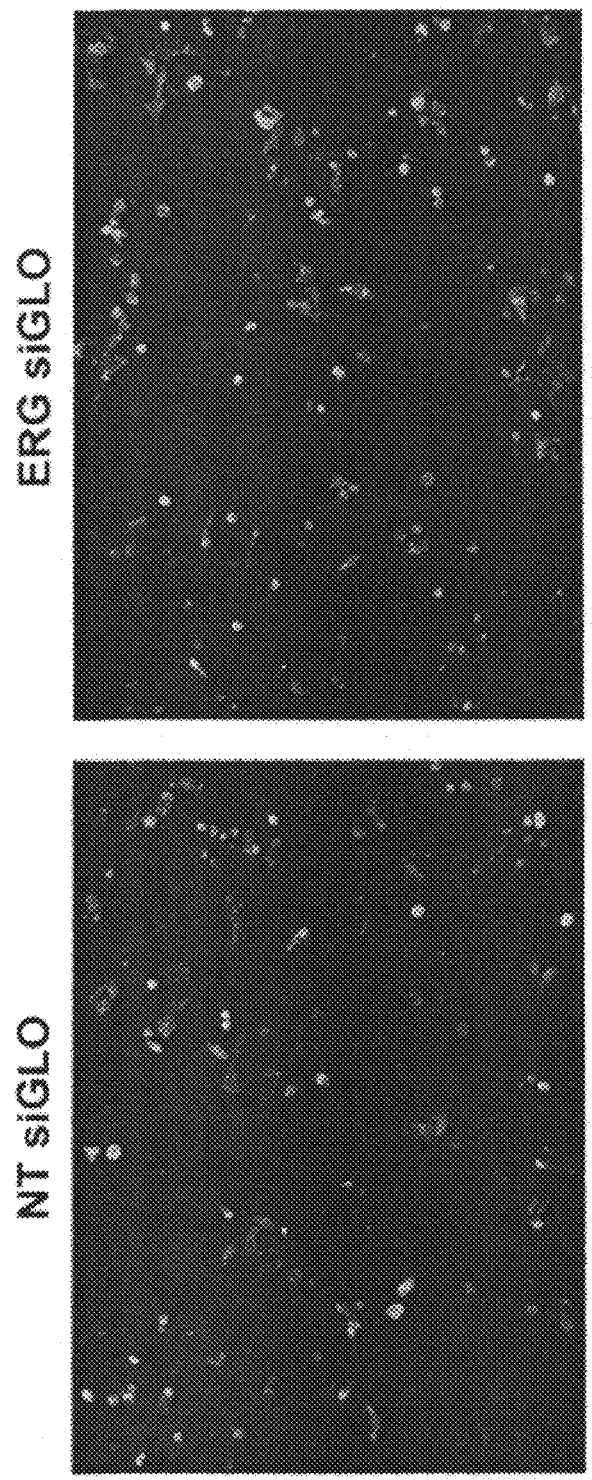
FIG. 9C demonstrates that the transfection efficiency of VCaP cells transfected with 50 nM of ERG siGLO or NT siGLO (both from Dharmacon Research, Lafayette, Colo.) and cultured for two days was nearly 100%.

ERG knockdown also inhibited prostate tumor cell proliferation in vitro and in vivo. FIG. 9B shows the morphology of VCaP cells transfected with 50 nM ERG siRNA, compared to controls ("NT"). Experiments were performed in triplicate and the cell morphology monitored on days 1, 4, 6, and 8 post transfection (FIG. 9B, top left panel).

ERG siRNA inhibited VCaP cell proliferation, decreasing the number of cells present in the cultures compared to cells treated with control RNA (FIG. 9B, top right panel). Cells transfected with ERG siRNA were counted in triplicate at days 1, 2, 4, 6, 8, and 10 post transfection, and observed to grow at a slower rate than control cells ($p=0.001$).

Fluorescent activated cell sorting ("FACS") analysis of the cell cycle demonstrated a inhibitory effect of ERG siRNA on the number of cells in S phase, compared to control RNA. The population of cells in S phase and the distribution of cells in G1, S and G2+M phases was assessed by analyzing the cells at the indicated time points from three independent experiments. Phospho-Rb to total Rb ratios were measured at day four by Western blot assay. ERG siRNA induces a redistribution of the number of cells in G1, S and G2+M phases, significantly increasing the number of cells in S phase.

Inhibiting ERG expression with ERG siRNA drastically reduced the growth of VCaP cells injected into severe combined immunodeficient ("SCID") mice. Male SCID mice (Harlan Sprague-Dawley, National Cancer Institute, Frederick, Md.) 4-6 weeks old and weighing 18 to 20 g, housed in sterile filter-capped cages, fed and given water ad libitum, were injected subcutaneously with VCaP cells. All animal studies were carried out according to NIH-approved protocols, in compliance with the Guide for the Care and Use of Laboratory Animals.

The injected VCaP cells were treated with ERG siRNA or NT control RNA, trypsinized, washed, and three million cells in a volume of 0.2 ml were injected into the flanks of the SCID mice. Tumor formation was assessed bi-weekly for up to seven weeks. Tumor growth analysis was performed by determining tumor volume (LW2/2), as described by Polverino et al., CANCER RES 66:8715-21, whereby L and W represent the length and the width of the tumor.

FIG. 9B, lower right panel, shows the tumor growth at days 35 ($p=0.0072$) and 42 ($p=0.0072$). Standard deviation (SD) and average tumor volumes (AVG) at day 42 are shown in the table. All of the animals treated with ERG siRNA had a reduced tumor load compared to the control animals and some had no tumor load (FIG. 9B, lower right panel).

Figure 19:
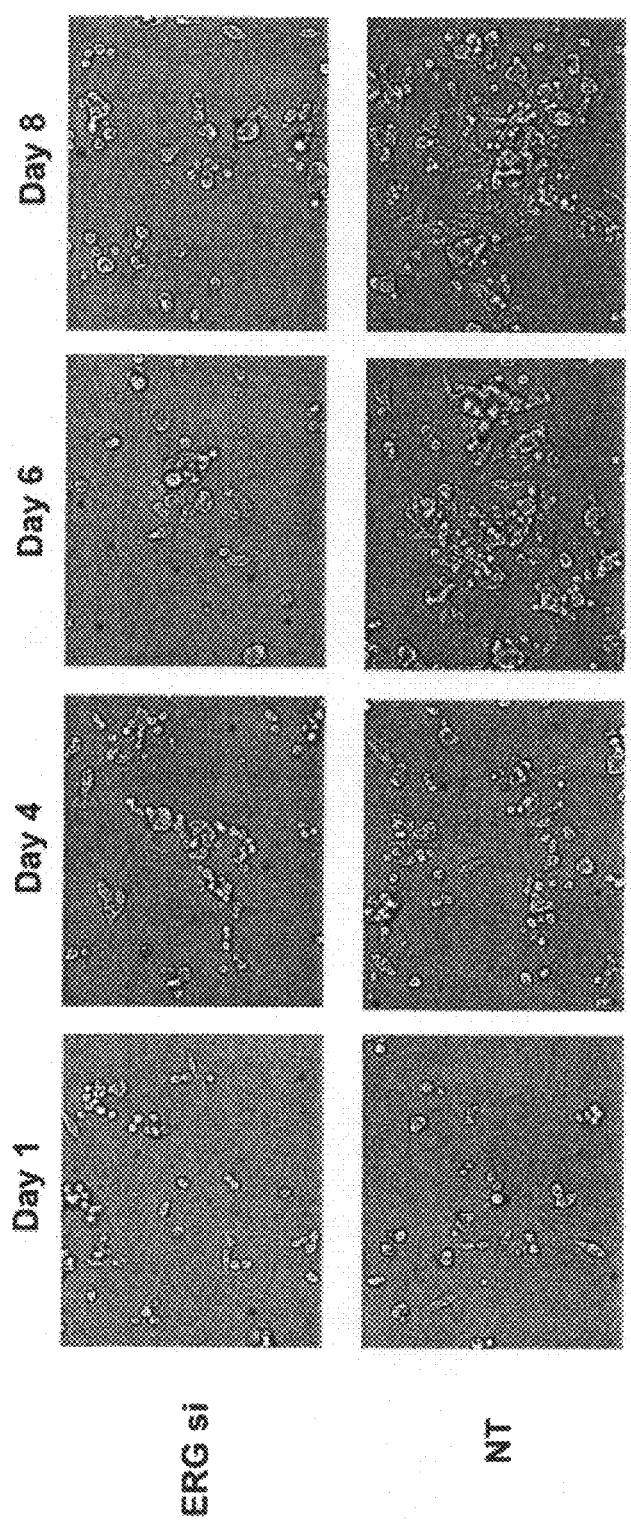
FIG. 19 shows the effect of ERG siRNA on the density and morphology of VCaP cells, compared to NT control cells.

ERG knockdown inhibited VCaP cell growth in complete medium. VCaP cells seeded into 10 cm tissue culture dishes in medium comprising 10% cFBS were cultured for three days, then transfected with ERG siRNA or control RNA. Cells from triplicate experiments were examined on day 1, 4, 6, and 8 by microscopy, as shown in FIG. 19.

Figure 10:
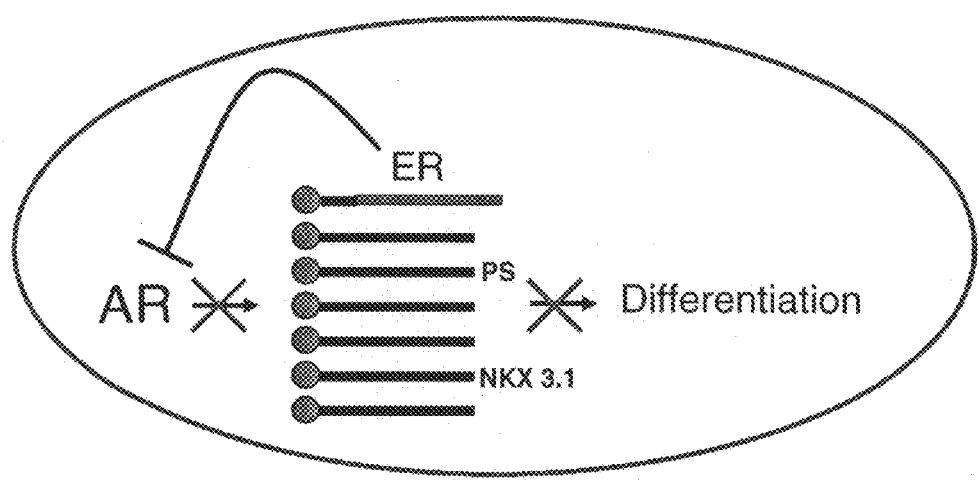
FIG. 10 is a diagram showing that ERG expression can result in inhibition of the androgen receptor responsive genes PSA and NKX3.1, thereby inhibiting cellular differentiation.

These data demonstrate a relationship between the in vivo expression of TMPRSS2-ERG or ERG and the expression of other androgen-regulated genes, such as PSA/KLK3 and NKX3.1. Because downregulation of ERG expression correlates with increased expression of NKX3.1 and PSA/KLK3, this indicates that these androgen-regulated genes are downregulated by ectopic ERG expression. NKX3.1 is a tumor suppressor gene and also a transcriptional target of the androgen receptor. Suppression of NKX3.1 by ERG overexpression in prostate cancer cells may therefore interfere with androgen receptor-mediated cell differentiation and negative regulation of cell growth. A schematic of this model is shown in FIG. 10.

As an example of an application for the use of inhibitory molecules in targeting transcripts of the ERG locus for degradation, we used siRNA-1 to inhibit ERG expression in VCaP prostate cancer cells. As noted, siRNA-1 targets exon 11, which is found in ERG1, ERG2, ERG3, ERG8, EPC1, and EPC2 transcripts and in the predicted products of the alternative internal promoter. VCaP cells respond to androgen hormone treatment, therefore, the effect of ERG inhibition on cell growth can be tested by stimulating the cells with androgen hormone.

To perform the siRNA inhibition, cells were first plated to 30% confluence in 100 mm cell culture dishes. Growth was synchronized by incubating the cells in hormone depleted serum (cFBS) containing media for three days. Then the cells were transfected with siRNA-1 and non-targeting (NT) control siRNA using the lipofectamine 2000 reagent (Invitrogen, Carlsbad, Calif.). After transfection 0.1 nM of R1881 synthetic androgen (New England Nuclear, Boston, Mass.) was added to the media. The cells were incubated for nine days, with a media change every three days. Cell cultures were then photographed and 100× magnification of representative view fields were captured.

A microscopic view of VCaP cells is shown in FIG. 11. Cells treated with the control NT siRNA are shown in FIG. 11A, while FIG. 11B shows cells treated with siRNA-1. VCaP cells treated with siRNA-1 exhibited a robust reduction in cell numbers. In addition, striking changes in cell morphology were also apparent. Thus, we were able to show that siRNA-1 treatment inhibited androgen-stimulated growth of VCaP cells.

Taken together, these data suggest that there is a regulatory loop between ERG and the androgen receptor and that negative regulation of the androgen receptor by ERG may contribute to prostate tumorigenesis. Accordingly, there are several therapeutic interventions that can be applied in an early stage prostate cancer (such as well to moderately differentiated tumors) harboring a TMPRSS2-ERG fusion or ERG overexpression. For example, ERG-siRNA, shRNA, or other small molecules can be used to reduce ERG expression in early stage prostate cancer, which is the most common stage of prostate cancer identified in post-PSA screening era. Alternatively or in addition, the androgen receptor can be selectively inhibited with beneficial effects.

It should be again noted that in the context of therapeutic interventions, any mention of "ERG" includes not only ERG8, EPC1, ECP2, and transcript products from the prostate cancer-specific promoter described herein, but also ERG1, ERG2, and ERG3, as well as their combinations, unless specifically indicated to the contrary by context or by an explicit exclusion of one or more of those isoforms. Thus, although we have exemplified inhibition of androgen-stimulated growth with an siRNA specific for exon 11, which is shared by ERG1, ERG2, ERG3, ERG8, EPC1 and EPC2 transcripts, siRNA, shRNA, or other small molecule inhibitors targeted to only one, or any combination of more than one, of those isoforms may also be employed. Such siRNA, shRNA, or other inhibitors that are specific for only one of ERG1, ERG2, ERG3, ERG8, EPC1, EPC2, or a transcript product from the prostate cancer-specific promoter, or that inhibit combinations of those isoforms, can be designed using the sequence data provided elsewhere in the Examples and may include the various primer and probe sequences mentioned.

For example, ERG8 gene expression can be blocked by targeting ERG8 specific nucleotide sequences with inhibitory nucleic acids. Examples of sense-strand specific sites suitable for targeting are:

```
5'-GGAACCACTTCTAGCAATA-3'      (SEQ ID NO: 41)

5'-CGAATAATGAGCAGGGAGA-3'      (SEQ ID NO: 42)

5'-CCAGGGAGCTAAAGAGAAT-3'      (SEQ ID NO: 43)

5'-CTGGGAAGCATGATGGAAA-3'      (SEQ ID NO: 44)

5'-GACTCAAGCTTTAGAGATT-3'      (SEQ ID NO: 45)
```

SEQ ID NO: 41 corresponds to nucleotides 1595-1613 of SEQ ID NO: 30; SEQ ID NO: 42 corresponds to nucleotides 1722-1740 of SEQ ID NO: 30; SEQ ID NO: 43 corresponds to nucleotides 2013-2031 of SEQ ID NO: 30; SEQ ID NO: 44 corresponds to nucleotides 2150-2168 of SEQ ID NO: 30; and SEQ ID NO: 45 corresponds to nucleotides 2334-2352 of SEQ ID NO: 30.

Progressive tumors that do not express ERG, or express ERG only at low levels, reflect an escape from an intact androgen receptor signaling network. These tumors may be treated by selective upregulation of androgen-regulated genes (e.g., tumor suppressors or cell differentiation and growth inhibitors, such as NKX3.1 and PMEPA1), so as to restore the protective component of the feedback regulation between ERG and the androgen receptor.

Example 8

The Androgen Receptor Function Index

The readout of androgen receptor ("AR") regulated genes ultimately reflects the status of in vivo AR function (ARF) in primary prostate cancer tissue, and consequently carries important information regarding prognosis and rational therapeutic decision making. Assessing the status of AR function in prostate cancer samples can provide early warning signs of androgen independence (van Gils et al., EUR UROL 48(6):1031-41 (2005)). Well characterized, annotated, and preserved human tissues (with long term follow-up data) from the CPDR Biospecimen Bank were used in high throughput screens to identify and validate prostate cancer biomarker genes.

In recent years, we have analyzed cell type specific gene expression from microdissected matched tumor and benign prostate epithelial cells. We found a general decrease in androgen regulated gene expression with prostate cancer progression. (Petrovics et al., ONCOGENE 24:3847-52 (2005).) Others have also recently noted a signature of attenuated AR function in late stage, especially in metastatic prostate cancer in human specimens (Tomlins et al., NAT GENET 39(1):41-51 (2007)), as well as in a xenograft model system (Hendriksen et al., CANCER RES 66(10):5012-20 (2006)). As part of a 12-gene panel, PSA was found to be underexpressed in aggressive prostate cancer. (Bismar et al., NEOPLASIA 8(1):59-68 (2006).) It should be noted, however, that several laboratories reported high AR expression, amplification, or activity in late stage metastatic prostate cancer. (Heinlein et al., ENDOCRINE REV 25:276-308 (2004); Chen et al., NAT MED 10:26-7 (2004); Dehm et al., J CELL BIOCHEM 99:333-344 (2006); Linja et al., CANCER RES 61:3550-55 (2001); Li et al., AM J SURG PATHOL 28:928-34 (2004).) These different findings underline the heterogeneous nature of late stage, especially androgen independent, metastatic prostate cancer. (Shah et al., CANCER RES. 64(24):9209-16 (2004).)

To develop an in vivo readout of AR functional status in prostate cancer cells, we have been pursuing parallel quantitative measurements of various AR regulated genes in carefully isolated benign and tumor cells of over 200 specimens as shown in Example 8. Quantitative expression analyses of androgen regulated genes at the mRNA level, such as PSA/KLK3, PMEPA1, PCA3, as well as androgen independent genes (AMACR, LTF), representing over 2000 data points, suggest that PSA/KLK3 and other androgen regulated genes reflect in vivo functional status of the AR and that their expression levels can be used to measure positive or negative correlation with aggressiveness of prostate cancer, as defined, for example, by Gleason grade, pathological stage, and/or biochemical recurrence. Initially we chose to focus on PSA/KLK3 mRNA as it is one of the most robust direct transcriptional targets of AR and is easily detectable in prostate cancer cells. (Kim et al., J CELL BIOCHEM 93(2):233-41 (2004).)

Our most recent data show that quantitative gene expression patterns of a panel of AR regulated genes in primary prostate cancer provide prognostic fingerprints. Using high-throughput assays as well as rational candidate gene strategies, we defined a set of six androgen inducible/co-regulated genes (PSA/KLK3, PMEPA1, NKX3.1, ODC1, AMD1, and ERG). Different combinations of two or more of these six genes, or their isoforms, can be used to provide a quantitative measure of in vivo AR function in prostate cancer specimens, i.e., the androgen receptor function index, or ARF index (ARFI). Although real time, quantitative PCR (QRT-PCR) was used to measure the expression levels of these genes, other techniques known in the art, such as immunohistochemistry, can be used to detect RNA or protein levels.

The ARFI readout can be converted into a single number index representing the overall in vivo AR activity, which in turn can be incorporated into nomograms, such as the one created by Kattan et al. that demonstrated the importance of PSA, Gleason sum, extra-capsular extension, surgical margins, seminal vesicle invasion, lymph node involvement, treatment year, and adjuvant radiotherapy in predicting 10-year probability of prostate cancer recurrence after radical prostatectomy. The nomograms can be used to model time-to-event data, including prediction of prostate cancer progression, combined with established clinical and pathological characteristics that predict this endpoint. The concordance index, C, can be used to assess the improvement in model fit upon inclusion of ARFI. (Harrell et al., JAMA 247(18):2543-6 (1982).) Current nomogram calculators incorporate measurable patient factors in an attempt to use such factors to predict an outcome, such as PSA recurrence following surgery, to aid in treatment decision making in advance of invasive procedures.

The ARFI genes are either direct targets of AR or are tightly regulated by AR, and cover major biological functions regulated by AR in prostate cancer. The gene set includes five androgen regulated genes and ERG. Our original observations of frequent overexpression of certain isoforms of ERG in prostate cancer (Foley et al., ENDOCR RELAT CANCER 11(3):477-88 (2004)), and subsequent independent study showing prevalent chromosomal rearrangements leading to the activation of ERG expression through AR-regulated TMPRSS2 gene promoter (Tomlins et al., SCIENCE 310(5748):644-8 (2005)), have highlighted ERG as an aberrant AR activated gene specific to prostate cancer. Therefore, the quantitative evaluation of ERG expression has been integrated in ARFI. The ERG read-out can be applied to TMPRSS2-ERG positive tumors, which account for greater than 60% of prostate cancer patients. (Id.)

It should be noted that although the following Examples use ERG1 as a model ERG isoform, ERG2, ERG3, ERG8, EPC1, ECP2, and combinations of those ERG isoforms can also be used, as may transcript products from the prostate cancer-specific promoter described in Example 5. Accordingly, any mention of "ERG" in the context of an ARFI readout includes not only ERG1, but also ERG2, ERG3, ERG8, EPC1, ECP2, and transcript products from the prostate cancer-specific promoter described herein, as well as their combinations, unless specifically indicated to the contrary by context or by an explicit exclusion of one or more of those isoforms. For example, ARFI readouts may employ an ERG gene that is not ERG1 or ERG2. Similarly, in some embodiments it may be desirable to include ERG8, EPC1, or EPC2 in the readout, but not ERG1 or ERG2.

Example 9

Co-Regulation of ARFI Genes Reflects Robust In Vivo Functional Linkage to AR Signaling We have recently completed a comprehensive gene expression analyses of microdissected prostate cancer cells and matched benign epithelial cells from radical prostatectomy specimens of 40 patients (80 GeneChips) (Petrovics et al., ONCOGENE 24:3847-52 (2005)). The GeneChip dataset was evaluated for androgen regulated gene expression. PSA/KLK3, PMEPA1, NKX3.1, ODC1, and AMD1, along with ERG (which can become androgen regulated in prostate cancer cells through fusion with a TMPRSS2 promoter in the majority of patients), were selected by their wide dynamic ranges of expression, as well as by their reported response to androgenic stimuli. (Heinlein et al., ENDOCRINE REV 25:276-308 (2004); Linja et al., J STEROID BIOCHEM MOL BIOL 92:255-64 (2004); Shaffer et al., LANCET ONCOL 4:407-14 (2003); Chen et al., NAT MED 10:26-7 (2004); Dehm et al., J CELL BIOCHEM 99:333-344 (2006); Segawa et al., ONCOGENE 21(57): 8749-58 (2002); Xu et al., INT J CANCER 92(3):322-8 (2001).) Moreover, some of these genes (NKX3.1, ERG, PMEPA1) may be causally linked to prostate cancer development.

Figure 12:
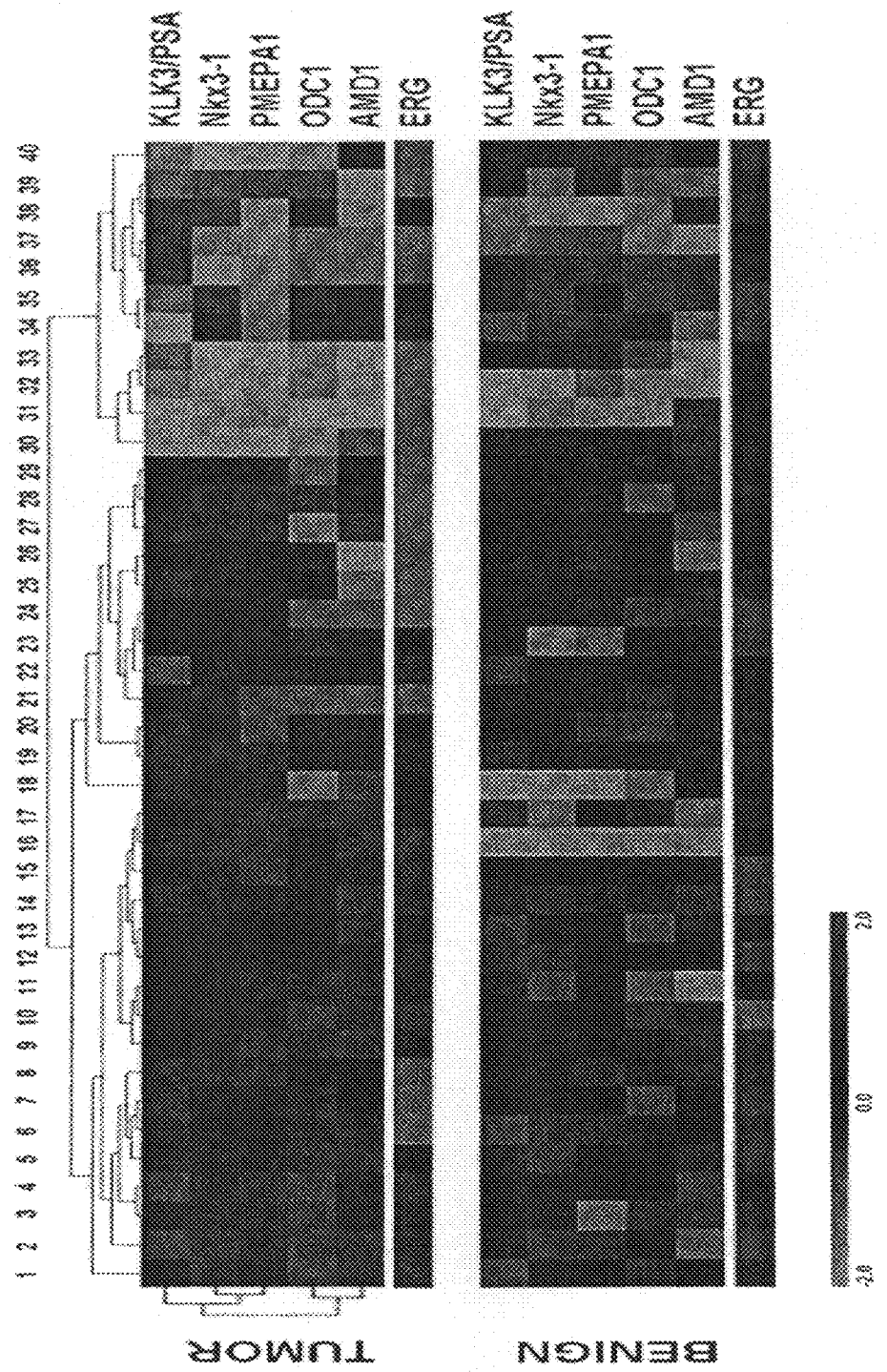
FIG. 12 compares the intensity of gene expression of the androgen regulated genes PSA/KLK3, NKX3.1, PMEPA1, ODC1, AMD1, and ERG in tumor and matched benign cells from 40 prostate cancer patients. Z-score normalized Gene-Chip derived expression intensities are depicted by heat maps on a high-to-low scale after hierarchical clustering. Patient numbers (N=40) are listed above the heat map. Matched tumor and benign specimens are listed in the same order.

The concerted expression of this gene panel (ARFI) is reflective of the functional status of in vivo AR activity. Normalized expression intensity values are depicted in a heat map format (FIG. 12). A non-supervised hierarchical cluster analysis (software from TIGR, Gaithersburg, Md.) was performed both by patients and also by genes and revealed robust in vivo co-regulation of ARFI genes in the tumor cells of prostate cancer patients, reflecting either active or dysfunctional AR (FIG. 12). Two tight gene sub-clusters emerged: PSA/KLK3, NKX3.1, PMEPA1, and ODC1, AMD1 (polyamine pathway), differing in expression only in the middle 12-patient cluster, which underlines the importance of using a panel of ARFI genes representing different downstream AR pathways. The other two large patient clusters show tight co-regulation of all ARFI genes reflecting either active AR (left 17-patient cluster), or dysfunctional AR (right 11-patient cluster) (FIG. 12). ERG also co-regulates closely with other ARFI genes in tumor cells of the majority of prostate cancer patients, where ERG is likely fused to the androgen regulated TMPRSS2 promoter, providing a highly specific tumor cell marker.

Figure 13:
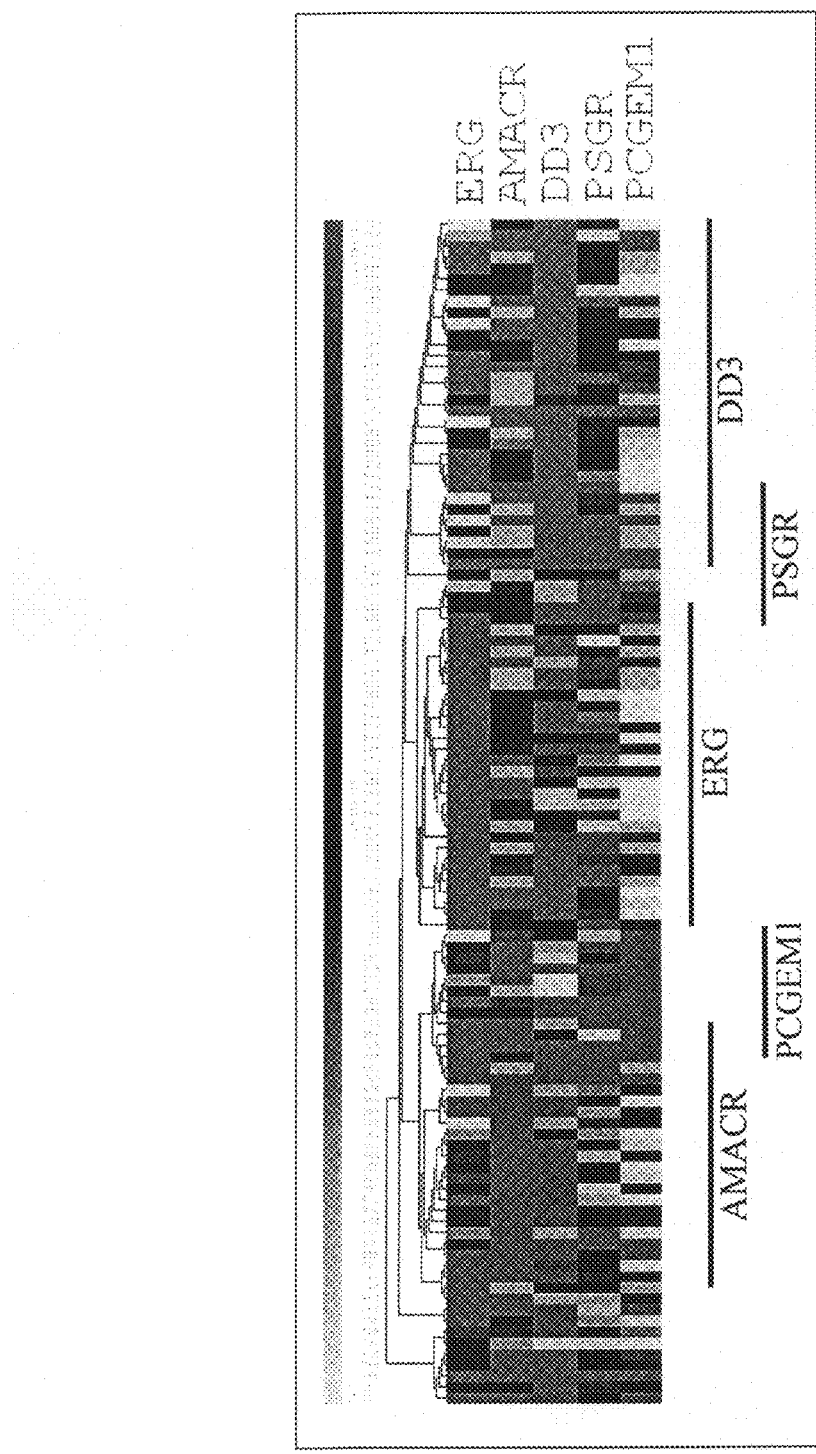
FIG. 13 shows a heat map display comparing the intensity of gene expression of the prostate cancer related genes ERG, AMACR, DD3, PSGR, and PCGEM1 in cells microdissected from prostate tissue sections.

We have also shown that ERG can be used as part of a multigene panel with other prostate cancer-associated genes that are not androgen regulated. FIG. 13 shows a heat map for a multigene panel that includes ERG, AMACR, DD3, PSGR, and PCGEM1. The heat map is a non-supervised hierarchical clustering of tumor over normal gene expression ratios derived from TaqMan QRT-PCR analysis of microdissected cell samples from prostate tissue sections. When non-AR genes were used in the multigene panel, we found strong overexpression of the various marker genes in distinct, but overlapping subsets of patients.

Example 10

Validation of In Vivo Co-Regulation of ARFI Genes by QRT-PCR

Figure 14:
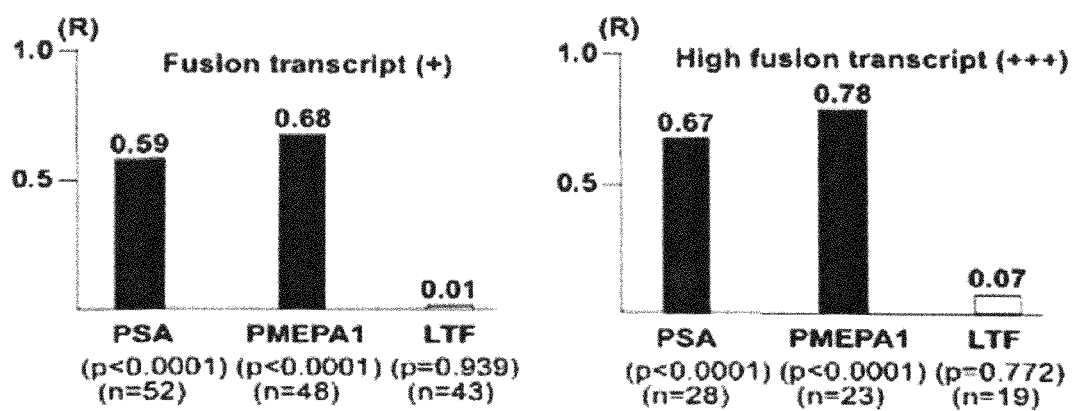
FIG. 14 shows the correlation of androgen regulated PSA/KLK3 and PMEPA1 genes with ERG expression in tumor cells of prostate cancer patients harboring TMPRSS2-ERG fusion using QRT-PCR.

Using QRT-PCR, we evaluated the expression of ERG transcripts for a relationship with the expression of the androgen-regulated genes, PSA/KLK3 and PMEPA1 (Dehm et al., J CELL BIOCHEM 99:333-344 (2006); Xu et al., CANCER RES 63(15):4299-304 (2003)), in prostate cancer cells of patients with TMPRSS2-ERG fusion. LTF (Ward et al., CELL MOL LIFE SCI 62(22):2540-8 (2005)), a non-androgen regulated control gene, was assayed in the same tumor cells (FIG. 14). In the figure, significant correlations (R>0.5) are marked by solid bars. LTF, a non-androgen regulated gene, was used as a negative control. The Pearson correlation coefficient (R) is shown above the bars. P values and the number of patients (n) assessed in the experiments are indicated under the bars.

Sixty five patients with detectable TMPRSS2-ERG fusion transcript in prostate cancer cells were selected for this study. Striking co-regulation was observed between the expression levels of ERG, tissue PSA/KLK3 ($p<0.0001$) and PMEPA1 ($p<0.0001$) in patients with detectable TMPRSS2-ERG transcripts. The co-regulation is even stronger in the subset of these patients where the expression level of the TMPRSS2-ERG fusion transcript is above the median ("High fusion transcript," FIG. 14 right panel). These data indicate that the level of co-regulation within the ARFI genes (including TMPRSS2-ERG) reflects the overall functional status of AR in prostate cancer cells and that decreased expression of ARFI genes correlates with compromised or diminished androgen receptor signaling in prostate tumor cells. Furthermore, the data indicate that the expression levels of ARFI genes are reduced in advanced prostate cancer, such as pT3 stage prostate cancer.

Example 11

Figure 15:
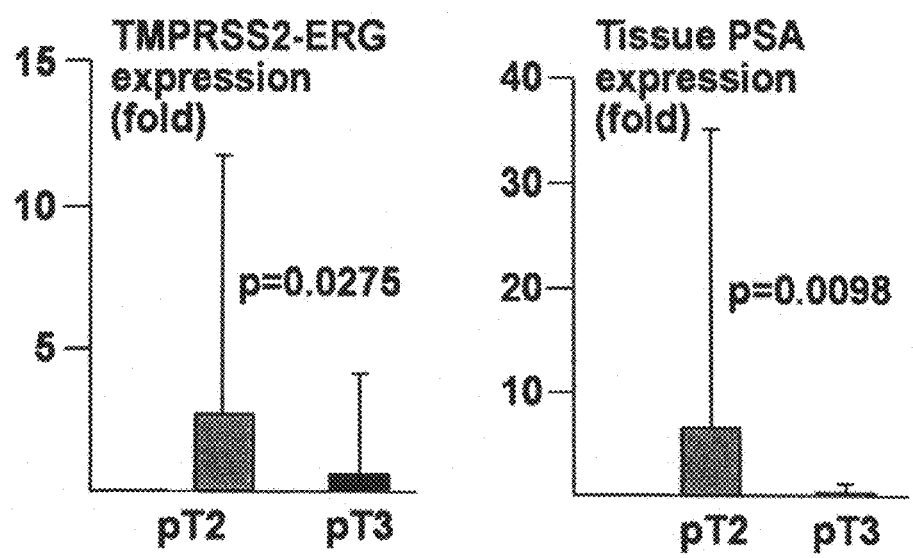
FIG. 15 demonstrates that ERG expression mirrors androgen signaling in prostate cancer tissue. TMPRSS2-ERG fusion (left panel) and PSA/KLK3 (right panel) transcript levels were compared in prostate cancer cells of pT3 and pT2 stage tumors by quantitative PCR. Y-axis scales represent fold changes of tissue expression levels relative to the expression of the GAPDH housekeeping gene.

PSA/KLK3 and TMPRSS2-ERG Indicate a Decrease of In Vivo AR Activity During Prostate Cancer Progression PSA/KLK3 and ERG mRNA expression were further analyzed for their relationship to prostate cancer progression in a larger patient cohort. As shown in FIG. 15, patients with pT3 prostate cancer (locally invasive tumor growing outside the capsule) had significantly ($p=0.0098$) lower expression of PSA/KLK3 transcript levels as compared to patients with pT2 stage disease (organ confined). Moreover, decreased TMPRSS2-ERG fusion transcript levels were also apparent in the prostate cancer cells of pT3 patients ($p=0.0275$).

Figure 16:
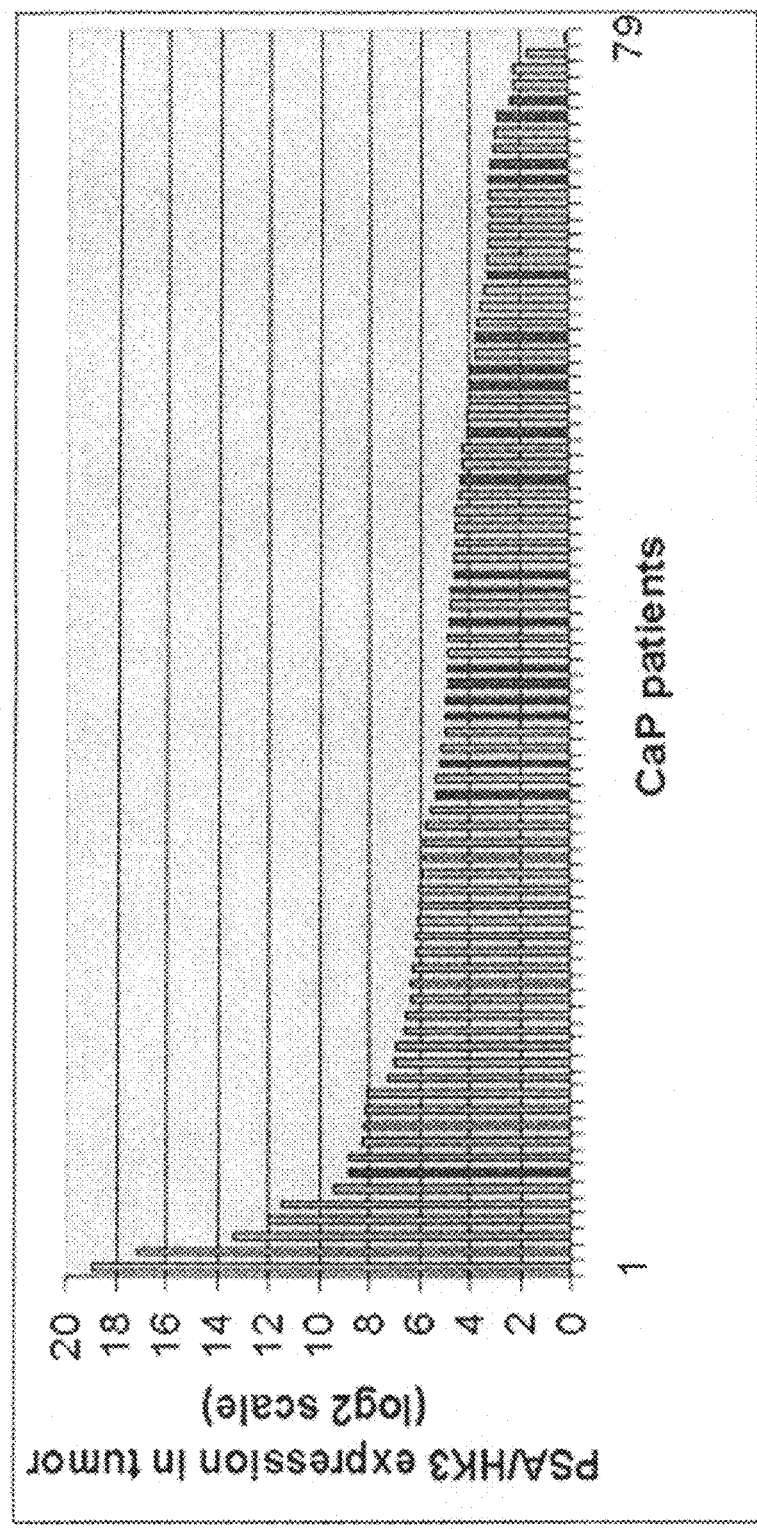
FIG. 16 shows the distribution of biochemical recurrence and tissue PSA/KLK3 mRNA expression in tumor cells of prostate cancer (CaP) patients. Relative expression of PSA/KLK3 mRNA in tumor cells, represented by vertical bars, is shown on a log 2 scale. Darkened bars indicate patients with biochemical recurrence.

To study patients with intermediate serum PSA levels, further analysis was limited to patients with serum PSA from 2 to 10 ng/mL (n=79). Based on serum PSA levels, these patients have an uncertain prognosis. FIG. 16 shows the distribution of PSA/KLK3 mRNA expression levels in tumor cells of prostate cancer patients with biochemical recurrence.

Figure 17:
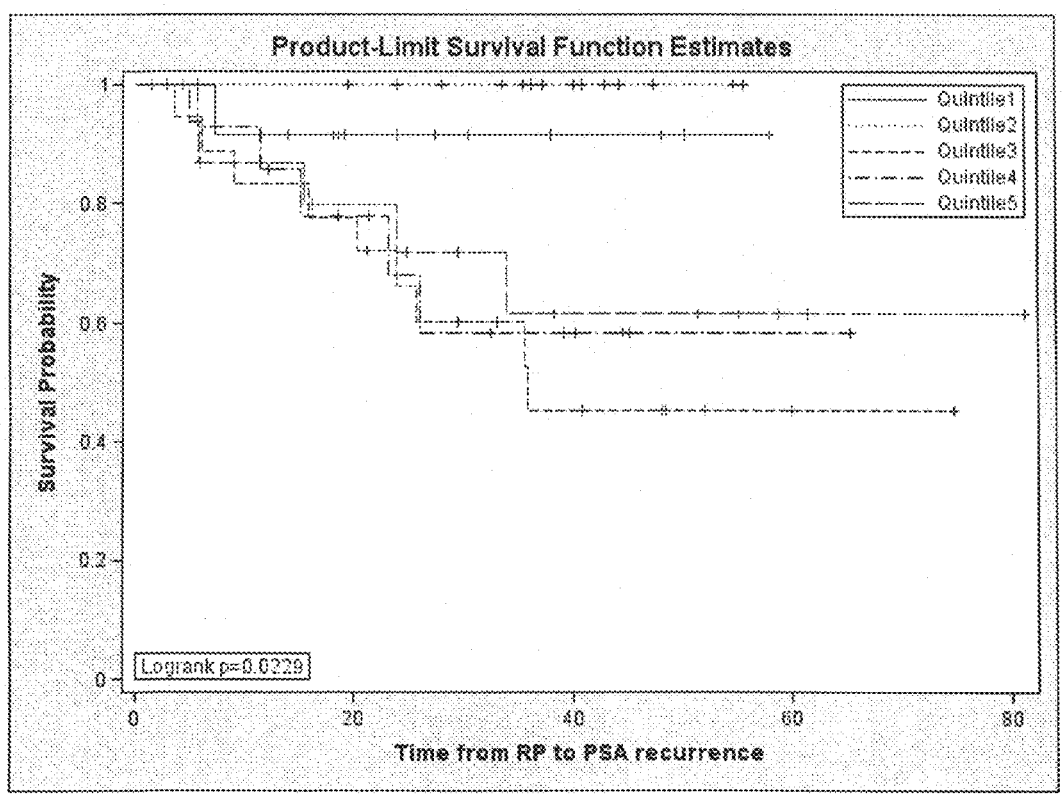
FIG. 17 shows a Kaplan-Meier survival estimation curve for time to PSA recurrence-free survival by tumor tissue PSA/KLK3 mRNA quintiles among patients with serum PSA 2-10 ng/ml. Quintiles are presented in decreasing order with quintile 1 referring to the highest and quintile 5 to the lowest PSA/KLK3 expression (N=79). Lower tissue PSA/KLK3 mRNA expression in prostate tumor cells correlates with an increased risk of biochemical recurrence.

Statistical analysis of the data presented in FIG. 16 demonstrates that the expression of tissue PSA/KLK3 mRNA in tumor cells of biochemical recurrence free patients was significantly higher than in patients with biochemical recurrence ($p=0.0062$, Student t-test). PSA/KLK3 mRNA expression in benign epithelial cells did not show such correlation. This prostate cancer patient cohort was divided into quintiles based on tissue PSA/KLK3 mRNA expression levels in tumor cells, and was compared with respect to time to biochemical relapse. As seen in FIG. 17, an unadjusted Kaplan-Meier analysis demonstrates improved biochemical survival for patients with the highest tissue PSA/KLK3 mRNA expression (Quintiles 1 and 2) (p=0.0229). Thus, PSA/KLK3 mRNA expression in tumor cells of prostate cancer patients inversely correlates with disease recurrence. High expression levels of tumor PSA/KLK3 mRNA correlates with biochemical recurrence free survival, whereas with low expression levels of PSA/KLK3 mRNA reflect an alteration of AR signaling in the tumor cell microenvironment, leading to an increased likelihood of tumor recurrence after prostatectomy.

Example 12

ERG Activates C-MYC, a Central Target of ERG in Prostate Cancer

Figure 18:
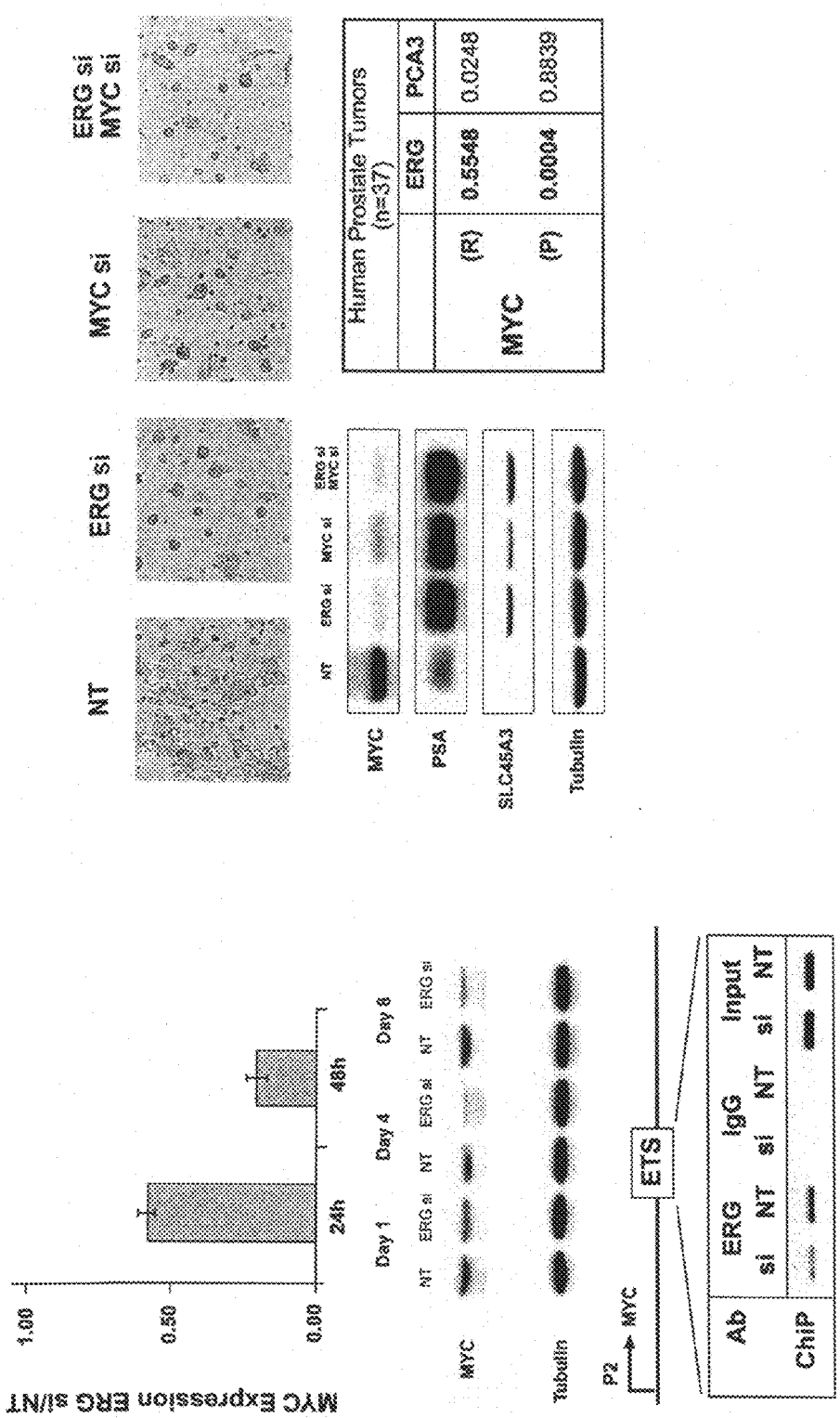
FIG. 18 shows the activation of the oncogene C-MYC by ERG. The left panel shows the result of RT-PCR analysis of VCaP cells treated with ERG siRNA. The top right panel shows the morphology of the VCaP cells after eight days of treatment with control ("NT"), ERG siRNA, MYC siRNA, and both ERG siRNA and MYC siRNA. The bottom right panel shows a Western blot analysis of the effect of ERG siRNA on C-MYC expression in VCaP cells. It also shows the correlation between ERG expression and MYC expression in microdissected human prostate tumors.

Inhibiting ERG decreased C-MYC expression and upregulated the prostate differentiation marker genes PSA and prostein. Furthermore, inhibiting C-MYC recapitulated the ERG siRNA phenotype. A double knockdown of ERG and C-MYC using 50-50% doses of inhibitory ERG and C-MYC siRNA molecules effectively controlled cell growth and rescued the differentiation program in prostate cancer cells (FIG. 18). C-MYC expression significantly correlated with ERG expression in human prostate tumor cells (FIG. 18).

Small interfering RNA ("siRNA") oligo duplexes designed to interfere with ERG function were based on the human ERG having the NCBI locus ID GXL__163565 and Accession No. NM__004440. The ERG siRNA 5'-CGACATCCTTCTCT-CACAT-3' (SEQ ID NO: 29) was purchased from Dharmacon, Lafayette, Colo.). The siRNA pool against human C-MYC (L-003282-00) (Locus ID: GXL__67312, Accession: NM__002467) and non-target ("NT") siRNA duplexes (D-001206-13-20) were both from Dharmacon, Lafayette, Colo.

VCaP cells were seeded into 10 cm tissue culture dishes in medium containing 10% charcoal-treated fetal bovine serum ("cFBS") (Gemini Bio-Products, Calabasas, Calif.) for three days. The cells were transfected with 50 nM NT, 50 nM ERG siRNA, 50 nM MYC siRNA, or the combination of 25 nM ERG siRNA and 25 nM MYC siRNA. Cotransfection of siRNAs and plasmids was carried out with Lipofectamine 2000 (Invitrogen, Carlsbad, Calif.), as described by the manufacturer for HEK 293 cells.

The coding region of ERG (NM__004440) was sub-cloned into an adenoviral transfer vector containing an internal ribosome entry site ("IRES"), wherein green fluorescent protein ("GFP") is expressed from the IRES translation initiation sequence ("IRES-GFP"). The generation of recombinant adenovirus plasmid and production of recombinant adenovirus were performed as described by Sun et al., ONCOGENE 25, 3905-13 (2006). Adenovirus titer was determined by GFP assay and plaque forming assay. VCaP and LNCaP cells were infected with the Ad-ERG or Ad-Control vectors and the proteins were detected by Western blot. A wild type ERG3 (NCBI Accession No. NM__182918) expression vector (pIRES-EGFP-ERG3) was generated by amplifying the coding sequences with the primers 5'-GGCTTTGAT-GAAAGCTCTAAACAAC-3' (SEQ ID NO: 50) and TCAAAAGTGCCTCAAGAGGA-3' (SEQ ID NO: 51) from a human normal prostate cDNA library (Catalog No. AM 3337, Ambion, Austin, Tex.) and was verified by DNA sequencing. HEK293 cells were transfected with wild type ERG3 or TM-ERG3-expressing vectors and the proteins were detected by Western blot.

Twelve hours after transfection with siRNA, the cells were treated with 100 pM R1881 and processed for the subsequent analyses. To knockdown ectopic ERG protein, TMPRSS2-ERG2 and TMPRSS2-ERG3 plasmids (pIRES-EGFP, Clontech, Palo Alto, Calif.) were generated by PCR amplification of human TMPRESS2 and ERG cDNA with the primers 5'-TAGGCGCGAGCTAAGCAGGAG-3' (SEQ ID NO: 8) and 5'-CCCTCCCAAGAGTCTTTGGATCTC-3' (SEQ ID NO: 12). The sequences were verified by DNA sequencing. Cotransfection of siRNAs and plasmids was carried out with Lipofectamine 2000 (Invitrogen, Carlsbad, Calif.), as described by the manufacturer for HEK 293 cells.

C-MYC expression in response to inhibition by ERG siRNA was measured by QRT-PCR and Western blot. In the QRT-PCR analysis, VCaP cells were transfected with siRNAs and harvested two or four days after transfection. Total RNA preparation and RT-PCR were performed as described by Gao et al., CLIN CAN RES 9:2545-50 (2003). Each RNA sample was evaluated for ERG knockdown by ERG siRNA in triplicate RT-PCR reactions and one control reaction performed in the absence of reverse transcriptase. The ERG PCR forward primer 5'-ACCGTTGGGATGAACTACGGCA-3' (SEQ ID NO: 10) and reverse primer 5'-TGGAGATGTGAGAGAAG-GATGTCG-3' (SEQ ID NO: 53) were used in the reaction. GAPDH gene expression was detected using forward primer 5'-GAGCCACATCGCCTCAGACACC-3' (SEQ ID NO: 54) and reverse primer 5'-GTTCTCAGCTTGACGGTGCC-3' (SEQ ID NO: 55). RT-PCR derived ERG or GAPDH fragments were separated by electrophoresis on Tris-borate EDTA-1% agarose gels and visualized by ethidium bromide staining. Band densities were quantified with Quantity One (Bio-Rad Laboratories, Hercules, Calif.) and ERG expression was normalized to GAPDH levels.

In the Western blot analysis, cells were lysed in M-PER mammalian protein extraction reagent (Pierce, Rockford, Ill.) supplemented with protease and phosphatase inhibitor cocktails (Sigma, St. Louis, Mo.). Immunoblot assays were performed according to standard procedures, for example, probing NuPAGE Bis-Tris gels (Invitrogen, Carlsbad, Calif.) with antibodies. Antibodies used in Western blot experiments include an immunoaffinity purified anti-ERG peptide polyclonal antibody prepared in our laboratory to the peptide having the amino acid sequence DFHGIAQALQPHPPESS-LYKYPSDLPYMGSYHAHPQKMNFVAPHPPAL (SEQ ID NO: 52), anti-PSA (Dako, Carpinteria, Calif.), anti-MYC (Upstate Biotechnology, Lake Placid, N.Y.), anti-SLC45A3 (Dako, Carpinteria, Calif.) or anti-GAPDH antibodies (SantaCruz, Santa Cruz, Calif.). To detect the endogenous ERG protein in VCaP cells, 80 µg cell lysate were loaded into each lane of the gel.

Reduced recruitment of ERG to the MYC P2 promoter downstream ETS element was assessed at 48 hours post-transfection by chromatin immunoprecipitation ("ChIP") assay, using an anti-ERG antibody (FIG. 18, bottom left panel). IgG and control genomic DNA amplicons ("Input") were used as controls.

ChIP assays were performed according to Masuda et al. J MOL BIOL 353:763-71 (2005). To detect specific ChIP products, 38 amplification cycles were performed. ETS binding sites within the target regions were identified by matrix match analysis using the GEMS Launcher software (Genomatix GmbH, Munich, Germany). ERG protein was detected with the polyclonal anti-ERG antibody sc-353 (SantaCruz Biotechnology, Inc., Santa Cruz, Calif.). Promoters directed to NCBI Accession No. GLX_67312/NM_002467 amplified the human C-MYC gene. The primer pair directed to the ETS binding site V$ETSF/PDEF0.1 P2 downstream promoter 5'-GCCCCTTGCATCCTGAGCTCC-3' (SEQ ID NO: 56) directed the 5'-GGTCGGACATTCCTGCTTTA-3' (SEQ ID NO: 57) and 5'-ACCCAACACCACGTCCTAAC-3' (SEQ ID NO: 58) was used as described in Meulia et al. MOL CELL BIOL 12:4590-600 were used. The androgen receptor ("AR") was immunoprecipitated with anti-AR antibodies and the PSA (KLK3) AREIII enhancer target region was amplified as described. (Masuda et al. J MOL BIOL 353:763-71 (2005)). The SLC45A3 gene (NCBI Accession No. GXL_151340/XM_001490454) promoter upstream ARE (V$GREF_ARE0.2) and ETS (V$ETSF_PDEF0.1) binding site containing region (5'-AGAGCACAGAAAGGCTGCCCTGG AAGTGGCTGGGCATCC TGTCAGCT-3') (SEQ ID NO: 59) was amplified by the 5'-TGTGGGACTTCTCTGC TGAA-3' (SEQ ID NO: 60) and 5'-CAACGTTCAAGGGGAAGAAA-3' (SEQ ID NO: 61) primers.

Cell morphology was also examined. Photomicrographs of VCaP cells at day 8 are shown in the top right panel of FIG. 18. PSA mRNA and protein expression were also measured by QRT-PCR and Western blot assays, respectively, and are shown in the bottom panel of FIG. 18. Cell lysates were prepared and assayed by Western blot with anti-C-MYC, anti-PSA, or anti-SLC45A3 (prostein) antibodies. Tubulin was used as a control.

ERG-MYC correlation analysis was performed by assessing quantitative gene expression data of C-MYC and ERG or C-MYC and PCA3 from 37 laser capture microdissected human tumors. The results were expressed as R and P-values, as shown in the table in the bottom right panel of FIG. 18. The correlation of ERG with C-MYC is highly significant; R=0.5548, p=0.0004.

Example 13

GeneChip® Data Analysis

VCaP cells were plated in medium containing 10% cFBS (Gemini Bio-Products, Calabasas, Calif.) for three days. Cells were transfected with 50 nM of siERG or 50 nM of control NT and grown in FBS containing media for 24 or 48 hours. Total RNA was isolated, five micrograms of RNA from each of the VCaP transfectants were biotin labeled, and GeneChip® HG U133 Plus 2.0 chips were hybridized with the labeled probes. Expression data were normalized by Robust Multi-array Averages (RMA) and fold changes in ERGsi/NT (24 h) and ERGsi/NT (48 h) treatment groups were calculated. A two fold cut-off criterion was applied for subsequent pathway analysis by the Bibliosphere Software using the functional co-citation-based analysis function (Genomatix GmbH, Munich, Germany) (Scherf et al., BRIEF BIOINFORM 6:287-97 (2005). Total RNA from human prostate specimens was isolated from laser capture microdissected tumor and benign epithelial cells, as described by Shaheduzzamen et al., CAN BIOL THER 6:(2007, Epub ahead of print). The RNA was quantified, amplified, biotinylated, hybridized to the high-density oligonucleotide human genome array HG U133A (Affymetrix, Santa Clara, Calif.), and normalized as described by Petrovics et al., ONCOGENE 24:3847-52 (2005). Tumor/normal ERG expression ratios were evaluated in the data set from well-differentiated prostate tumors. Gene expression changes were averaged in seven data sets where ERG expression was elevated 19-38 fold. A two-fold cut-off criterion was applied for further pathway analysis using Bibliosphere Software (Genomatix GmbH, Munich, Germany).

Normalized human ERG overexpressing tumor data was compared to the 48 h ERG siRNA treatment gene expression data. Common genes were selected for the subsequent network analysis by the Bibliosphere Software.

Figure 20:
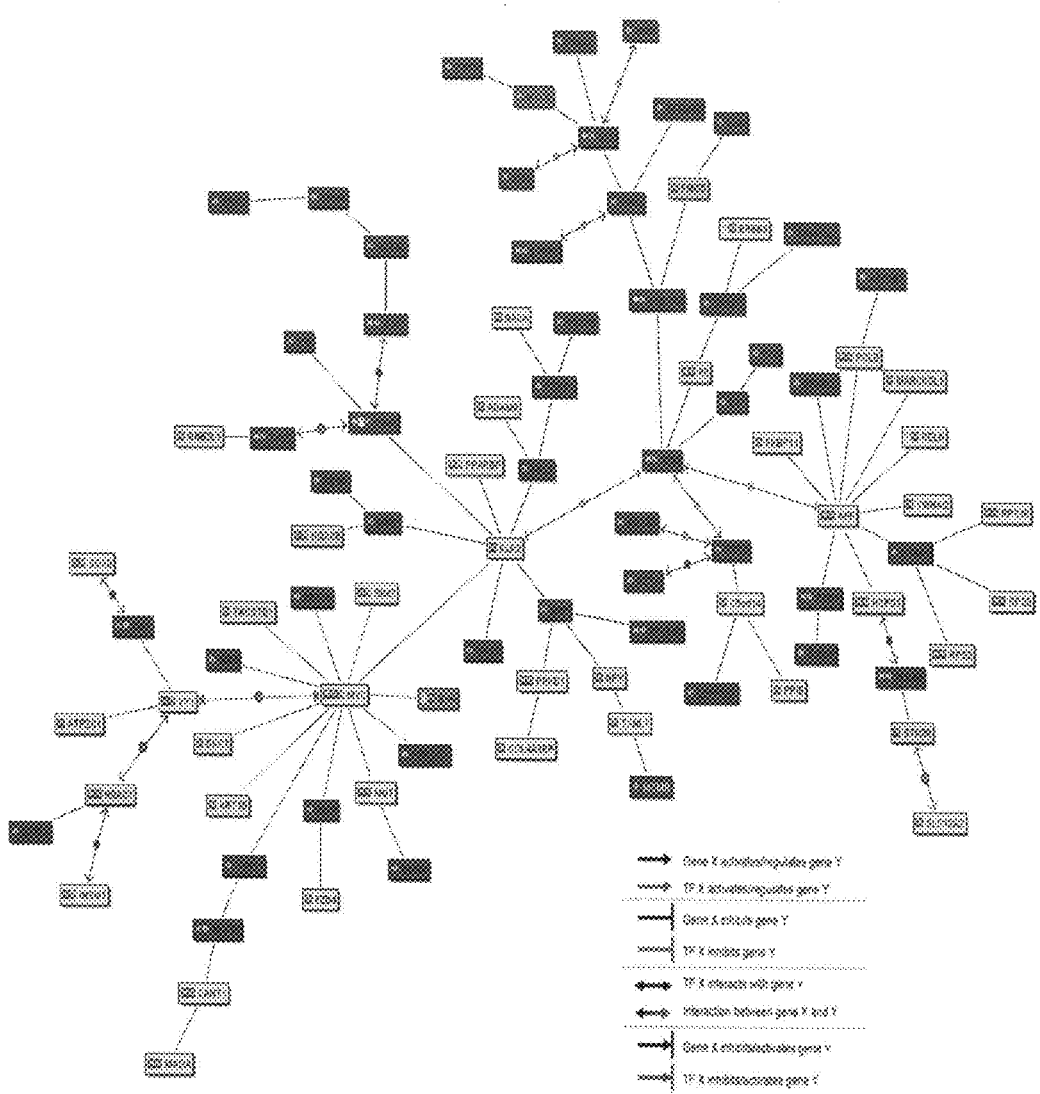
FIG. 20 shows a gene network in ERG-expressing human prostate tumors. Seven well-differentiated prostate tumors overexpressing ERG were analyzed with Bibliosphere software. Red (medium grey) and yellow (light grey) boxes indicate upregulation, shades of blue (dark grey) indicate down-regulation.

FIG. 20 shows a gene network in ERG expressing human prostate tumors. Normalized (tumor/normal) gene expression data of seven well-differentiated prostate tumors with 19-38 folds of ERG overexpression were analyzed by the Bibliosphere software (Shaheduzzamen et al., CAN BIOL THER 6:(2007, Epub ahead of print)). Red (medium grey) and yellow (light grey) boxes indicate upregulation, shades of blue (dark grey) indicate downregulation. The functional connections are disclosed in the insert to FIG. 20.

Figure 21:
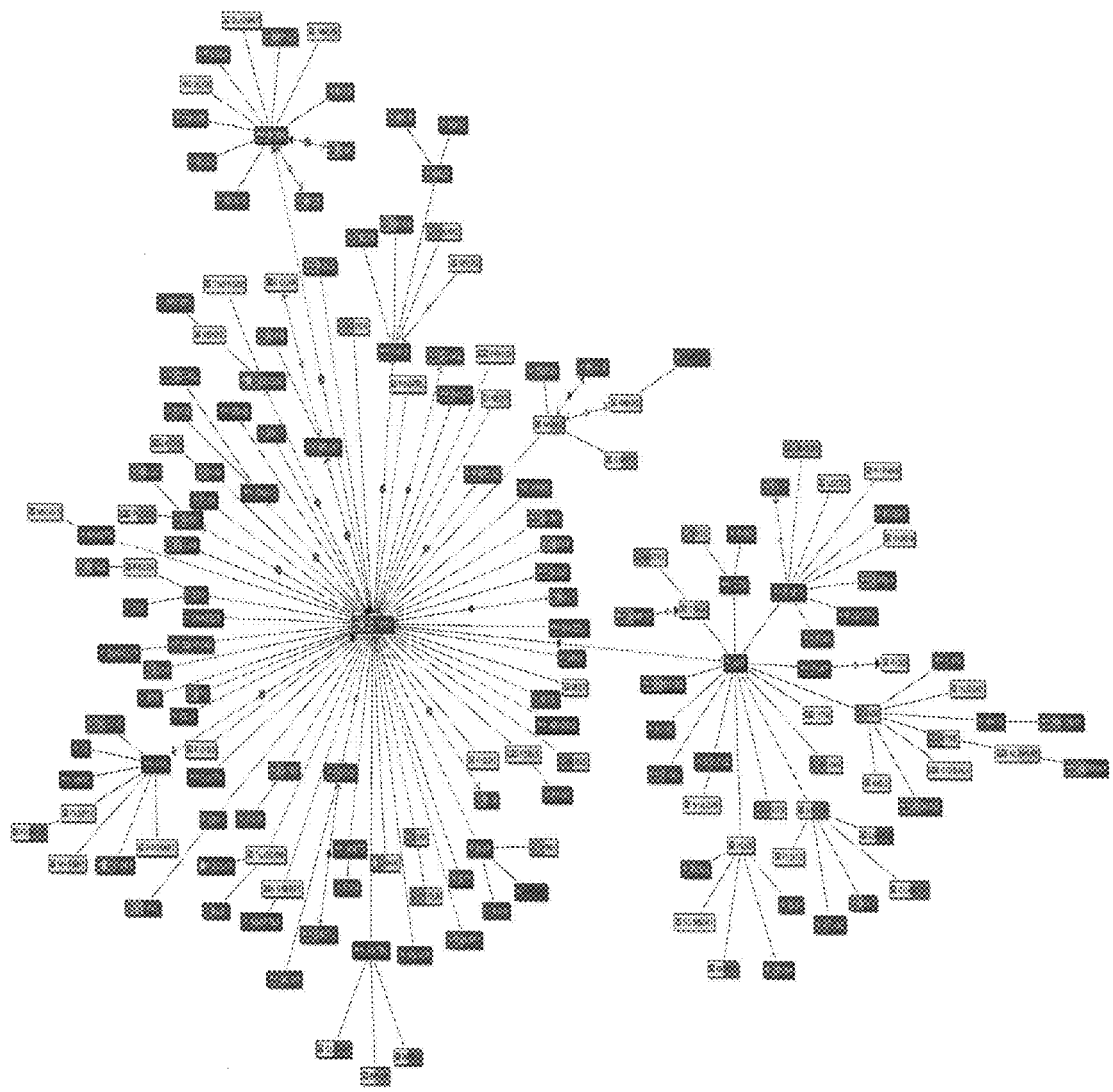
FIG. 21 shows a gene network affected in response to ERG knockdown in VCaP cells.

The network of genes affected in response to ERG knockdown in VCaP cells is shown in FIG. 21. Cells were transfected with either 50 nM of ERG siRNA or with 50 nM of NT and were incubated for 24 hours (left side codes) or 48 hour (right side codes). For probe labeling, total RNA was isolated from the cells and was labeled for hybridization. GeneChip® HG U133 Plus 2.0 chips were hybridized with the labeled probes. ERG si/NT expression ratios were calculated and a two-fold cut-off criterion was applied towards the subsequent pathway analysis by Bibliosphere Software. Gene symbols within the boxes indicate changes in gene expression (FIG. 21).

Figure 22:
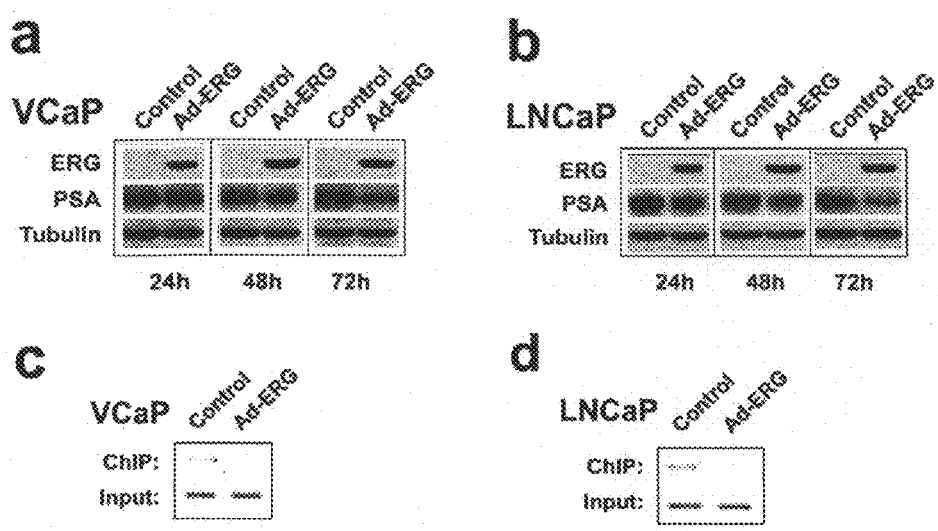
FIG. 22 shows Western blots demonstrating diminishing PSA protein levels and decreased recruitment of AR to the PSA AREIII enhancer in response to transient ERG expression.

Transient ERG expression diminished PSA protein levels and decreased recruitment of AR to the PSA AREIII enhancer. VCaP and LNCaP cells were infected with adenoviral ERG (Ad-ERG) or Ad-Control (Control) vectors. Cell lysates prepared at 24, 48, and 72 hours post-infection were analyzed in immunoblot assays with anti-ERG, anti-PSA, and anti-tubulin antibodies. ChIP assessment of AR recruitment to the KLK3/PSA gene AREIII enhancer in VCaP and LNCaP cells in response to the transient expression of ERG by adenoviral Ad-ERG or Control vectors (FIG. 22).

Example 14

Prostate Differentiation Genes are Repressed by ERG

Figure 23:
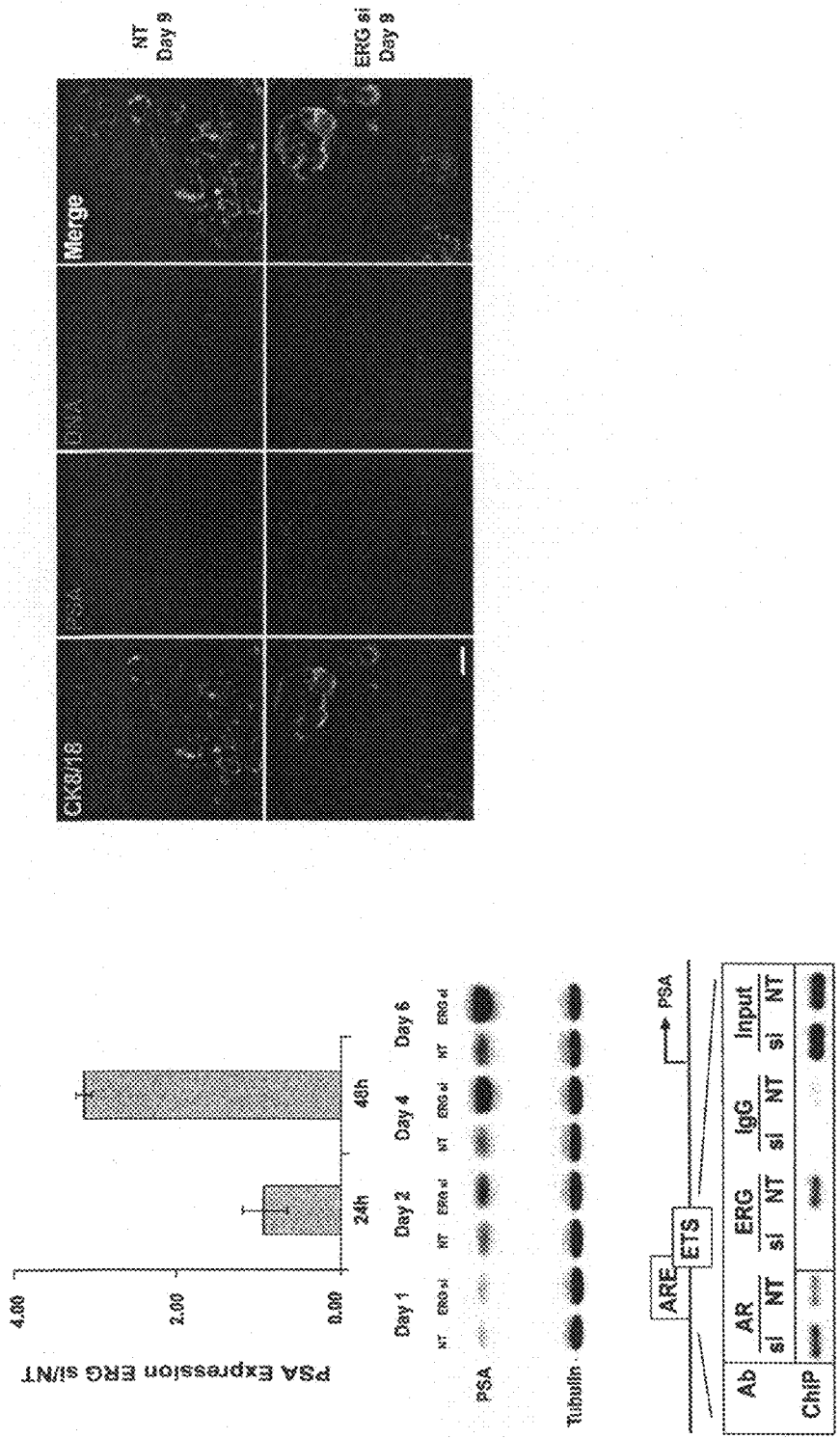
FIG. 23 shows the repression of prostate differentiation genes by ERG. The top left panel shows the increase in PSA mRNA expression resulting from ERG siRNA transfection of VCaP cells, measured by QRT-PCR. The top middle panel shows a corresponding increase in PSA protein expression, measured by Western blot. The bottom left panel shows increased AR binding to the PSA enhancer ("ARE") and decreased ERG recruitment to the overlapping ETS cognate element, measured by ChIP assay. The right panel shows an immunofluorescence micrograph of VCaP cells nine days after treatment with ERG siRNA. The cells were stained with antibodies to cytokeratin ("CK8/18") or PSA, or stained for DNA; the right panel compares merged images. The scale bar represents 25 microns.

ERG siRNA treatment resulted in the recruitment of androgen receptor to the PSA AREIII enhancer (FIG. 23). PSA mRNA and protein expression were measured by QRT-PCR and Western blot assays, respectively. Increased AR binding to the PSA enhancer (ARE) and decreased ERG recruitment to the overlapping ETS cognate element was measured by ChIP assay 48 hours after transfection. After 9 days of ERG siRNA treatment, VCaP cells were stained for cytokeratin CK8/18, PSA, and DNA (FIG. 23).

Figure 24:
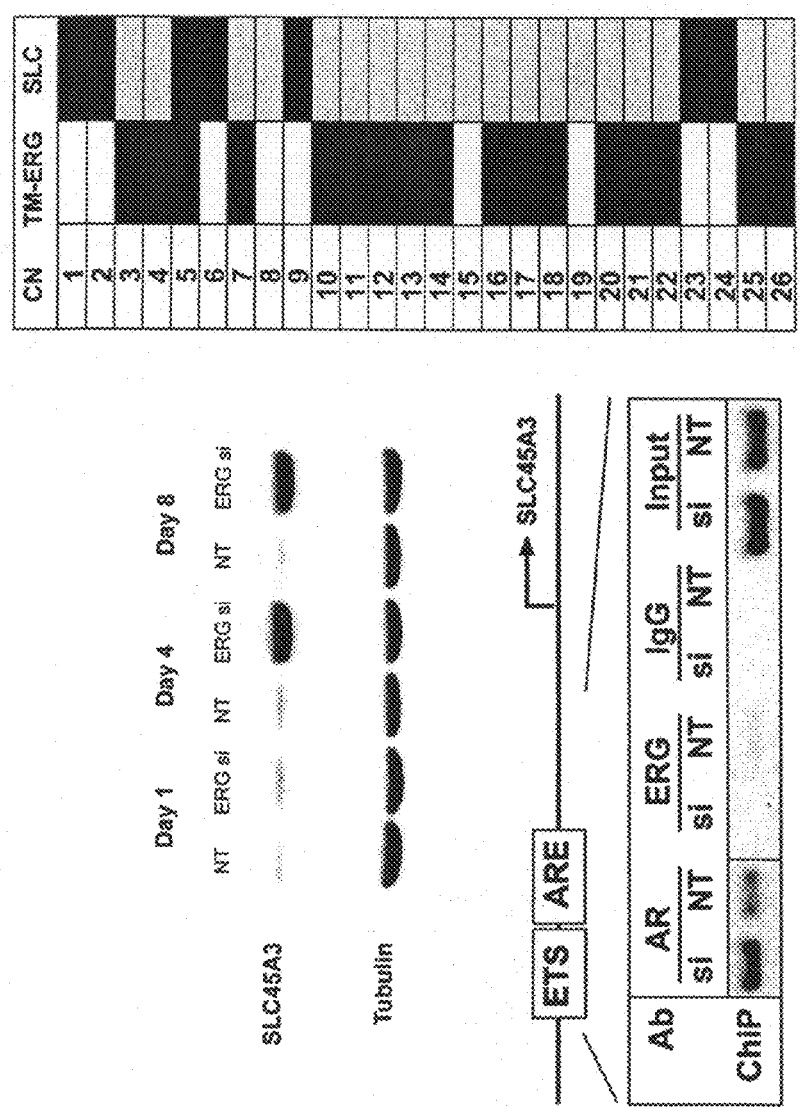
FIG. 24 shows the increase in prostein ("SLC45A3") expression in VCaP cells resulting from transfection with ERG siRNA. The top left panel shows a Western blot with antibodies to SLC45A3 and tubulin (control). The bottom left panel assesses recruitment of AR and ERG to the SLC45A3 promoter upstream ARE and ETS elements by ChIP assay. The right panel shows a matrix of immunostaining results from 26 prostate tumors examined with an antibody to SLC45A3. "CN" indicates the case number of the tumor tissue. "TM-ERG" indicates the presence (black bar) or absence (white bar) of the TMPRSS2-ERG gene fusion in the tumor. "SLC" indicates strong (dark grey bars) or weak (light grey bars) immunohistochemical staining with an antibody to SLC45A3.

ERG siRNA treatment also resulted in the recruitment of androgen receptor to the prostein (SLC45A3) gene upstream enhancer. Expression of TMPRSS2-ERG negatively correlated with prostein (SLC45A3) expression in human specimens (FIG. 24). SLC45A3 (Prostein) expression in ERG siRNA transfected VCaP cells was measured by Western blot. Recruitment of AR and ERG to the SLC45A3 promoter upstream ARE and ETS elements was assessed by ChIP assay 48 hours post-transfection. A matrix representation of TMPRSS2-ERG expression and SLC45A3 immunostaining of prostate tumors of 26 patients demonstrated a correlation between ERG siRNA treatment and prostein expression. Sections of whole mounted radical prostatectomy specimens were assessed by immunohistochemistry with anti-SLC45A3 (SLC) antibody.

Radical prostatectomy specimens from 26 patients were fixed in 10% buffered formalin and embedded as whole mounts in paraffin. Each prostate was sectioned at 0.22 cm intervals in a transverse plane perpendicular to the long axis of the posterior surface of the prostate and completely embedded as whole mounts. The volume of each tumor was calculated in three dimensions (apex to base, right to left, and anterior to posterior) using the largest dimension in each direction to determine the index tumor. Index tumor was analyzed for the presence or absence of TMPRSS2-ERG fusion transcripts as described by Furusato et al., MOD PATHOL 21(2):67-75 (2008), and for Prostein immunohistochemical staining on adjacent four-micron sections of the whole-mounted blocks. Slides were incubated with anti-SLC45A3 antibody (Dako North America, Carpinteria, Calif.), diluted 1:160. Vector VIP (purple) was used as the chromogen substrate (Vector Laboratories, Burlingame, Calif.) and the slides were counterstained with hematoxylin. SLC45A3 expression was assessed based on both the amount and intensity of immunopositive cells. Intensities were scored as "0" if not stained, "1" if stained weakly, and "2" if stained strongly. The percentage of positively stained area was also estimated and scored as "1" if less than 25% of the area stained positive, "2" if 25-50% stained positive, "3" if 51-75% stained positive, and "4" if more than 75% stained positive. The final score was determined by multiplying the intensity score and the percentage of positively stained area.

VCaP cells were fixed with 4% paraformaldehyde and centrifuged onto silanized slides (Sigma, St. Louis, Mo.) with a cytospin centrifuge. Cells were immunostained with anti-cytokeratin 8/18 and anti-PSA (both from Dako, Carpinteria, Calif.) followed by goat anti-mouse Alexa-488 and goat anti-rabbit Alexa-594 secondary antibodies (Invitrogen, Carlsbad, Calif.). Images were captured using a 40×/0.65 N-Plan objective lens on a Leica DMLB upright microscope with a QImaging Retiga-EX CCD camera (Burnaby, BC, Canada) controlled by OpenLab software (Improvision, Lexington, Mass.). Images were converted into color and merged by using Adobe Photoshop.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

What is claimed is:

1. A method of detecting the expression of Ets Related Gene 8 (ERG8) mRNA in a biological sample comprising nucleic acid sample isolated from human prostate epithelial cells, the method comprising:

(a) combining the nucleic acid sample isolated from human prostate epithelial cells with at least a first and a second oligonucleotide primer under hybridizing conditions, wherein the first and the second oligonucleotide primers amplify a target sequence comprising a 3' non-coding region within nucleotides 1311 to 2441 of SEQ ID NO: 30, and wherein the entire nucleotide sequence of at least one of the first or the second oligonucleotide primers hybridizes to a region within said nucleotides 1311 to 2441 of SEQ ID NO:30 or a nucleic acid strand complementary to said region;

(b) amplifying a plurality of amplification products when said nucleotides 1311 to 2441 of SEQ ID NO:30 are present in the nucleic acid sample by adding at least one polymerase activity to the biological sample containing the first and second oligonucleotide primers, wherein the amplification products comprises the region within nucleotides 1311 to 2441 of SEQ ID NO: 30 to which the entire nucleotide sequence of at least one of the first or the second oligonucleotide primers hybridizes;

(c) immobilizing the plurality of amplification products;

(d) combining an oligonucleotide probe with the immobilized plurality of amplification products to thereby permit the probe to hybridize to at least one immobilized amplification product;

(e) detecting whether a signal results from hybridization between the oligonucleotide probe and at least one amplification product, and (f) detecting expression of ERG8 mRNA in the biological sample if the signal is detected in step (e).

2. The method of claim 1, wherein the 3' non-coding region comprises nucleotides 1744 to 1848 of SEQ ID NO:30.

3. The method of claim 1, wherein the 3' non-coding region comprises nucleotides 2087 to 2176 of SEQ ID NO:30.

4. The method of claim 1, wherein the 3' non-coding region comprises nucleotides 2253 to 2343 of SEQ ID NO:30.

5. The method of claim 1, wherein the entire sequence of the first oligonucleotide primer hybridizes to a first region within said nucleotides 1311 to 2441 of SEQ ID NO:30 and the entire sequence of the second oligonucleotide primer hybridizes to a nucleic acid strand complementary to a second region within said nucleotides 1311 to 2441 of SEQ ID NO:30.

* * * * *

SEQUENCE LISTING

```
<160> NUMBER OF SEQ ID NOS: 62

<210> SEQ ID NO 1
<211> LENGTH: 1168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
taggcgcgag ctaagcagga ggcggaggcg gaggcggagg gcgaggggcg gggagcgccg      60
cctggagcgc ggcaggaagc cttatcagtt gtgagtgagg accagtcgtt gtttgagtgt     120
gcctacggaa cgccacacct ggctaagaca gagatgaccg cgtcctcctc cagcgactat     180
ggacagactt ccaagatgag cccacgcgtc cctcagcagg attggctgtc tcaaccccca     240
gccagggtca ccatcaaaat ggaatgtaac cctagccagg tgaatggctc aaggaactct     300
cctgatgaat gcagtgtggc caaaggcggg aagatggtgg gcagcccaga caccgttggg     360
atgaactacg gcagctacat ggaggagaag cacatgccac ccccaaacat gaccacgaac     420
gagcgcagag ttatcgtgcc agcagatcct acgctatgga gtacagacca tgtgcggcag     480
tggctggagt gggcggtgaa agaatatggc cttccagacg tcaacatctt gttattccag     540
aacatcgatg ggaaggaact gtgcaagatg accaaggacg acttccagag gctcaccccc     600
agctacaacg ccgacatcct tctctcacat ctccactacc tcagagagac tcctcttcca     660
catttgactt cagatgatgt tgataaagcc ttacaaaact ctccacggtt aatgcatgct     720
agaaacacag ggggtgcagc ttttattttc ccaaatactt cagtatatcc tgaagctacg     780
caaagaatta caactaggcc aggtacgaaa acacccctgt gtgatctctt cattgagaga     840
catcccagat gtcctgctga gatccgtgcc ctaagtcacg tgatacaaag agagctgatc     900
ccggagctga agccagtccc agacagtctt attctgcctc tgttgatttg gagactaaat     960
ccactcaaac catttcattc aaagaccaca ctaaaggaat taagagcaga ttagcccttt    1020
aactagcttt tcagaaagac agatgggcaa agaaggcatc ctggatgcct ggcagttagg    1080
aataggccga cttttgaact aacagaagga tctgtccctc ctcggggaa gagcacaaaa     1140
```
caaggacact ccccagattc acagtgac 1168

<210> SEQ ID NO 2
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Thr Ala Ser Ser Ser Asp Tyr Gly Gln Thr Ser Lys Met Ser
 1               5                  10                  15

Pro Arg Val Pro Gln Gln Asp Trp Leu Ser Gln Pro Pro Ala Arg Val
                20                  25                  30

Thr Ile Lys Met Glu Cys Asn Pro Ser Gln Val Asn Gly Ser Arg Asn
                35                  40                  45

Ser Pro Asp Glu Cys Ser Val Ala Lys Gly Gly Lys Met Val Gly Ser
            50                  55                  60

Pro Asp Thr Val Gly Met Asn Tyr Gly Ser Tyr Met Glu Glu Lys His
65                  70                  75                  80

Met Pro Pro Pro Asn Met Thr Thr Asn Glu Arg Arg Val Ile Val Pro
                85                  90                  95

Ala Asp Pro Thr Leu Trp Ser Thr Asp His Val Arg Gln Trp Leu Glu
                100                 105                 110

Trp Ala Val Lys Glu Tyr Gly Leu Pro Asp Val Asn Ile Leu Leu Phe
            115                 120                 125

Gln Asn Ile Asp Gly Lys Glu Leu Cys Lys Met Thr Lys Asp Asp Phe
130                 135                 140

Gln Arg Leu Thr Pro Ser Tyr Asn Ala Asp Ile Leu Leu Ser His Leu
145                 150                 155                 160

His Tyr Leu Arg Glu Thr Pro Leu Pro His Leu Thr Ser Asp Asp Val
                165                 170                 175

Asp Lys Ala Leu Gln Asn Ser Pro Arg Leu Met His Ala Arg Asn Thr
            180                 185                 190

Gly Gly Ala Ala Phe Ile Phe Pro Asn Thr Ser Val Tyr Pro Glu Ala
        195                 200                 205

Thr Gln Arg Ile Thr Thr Arg Pro Gly Thr Lys Thr Pro Leu Cys Asp
    210                 215                 220

Leu Phe Ile Glu Arg His Pro Arg Cys Pro Ala Glu Ile Arg Ala Leu
225                 230                 235                 240

Ser His Val Ile Gln Arg Glu Leu Ile Pro Glu Leu Lys Pro Val Pro
                245                 250                 255

Asp Ser Leu Ile Leu Pro Leu Leu Ile Trp Arg Leu Asn Pro Leu Lys
            260                 265                 270

Pro Phe His Ser Lys Thr Thr Leu Lys Glu Leu Arg Ala Asp
        275                 280                 285

<210> SEQ ID NO 3
<211> LENGTH: 1019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gcaggaggcg gaggcggagg cggagggcga ggggcgggga gcgccgcctg gagcgcggca      60
ggaagcctta tcagttgtga gtgaggacca gtcgttgttt gagtgtgcct acggaacgcc     120
acacctggct aagacagaga tgaccgcgtc ctcctccagc gactatggac agacttccaa     180
gatgagccca cgcgtccctc agcaggattg gctgtctcaa cccccagcca gggtcaccat     240
caaaatggaa tgtaacccta gccaggtgaa tggctcaagg aactctcctg atgaatgcag     300
tgtggccaaa ggcggggaga tggtgggcag cccagacacc gttgggatga actacggcag     360
ctacatggag gagaagcaca tgccaccccc aaacatgacc acgaacgagc gcagagttat     420
cgtgccagca gatcctacgc tatggagtac agaccatgtg cggcagtggc tggagtgggc     480
ggtgaaagaa tatggccttc cagacgtcaa catcttgtta ttccagaaca tcgatgggaa     540
ggaactgtgc aagatgacca aggacgactt ccagaggctc accccagct acaacgccga     600
catccttctc tcacatctcc actacctcag agagactcct cttccacatt tgacttcaga     660
tgatgttgat aaagccttac aaaactctcc acggttaatg catgctagaa acacaggggg     720
tgcagctttt attttcccaa atacttcagt atatcctgaa gctacgcaaa gaattacaac     780
taggccagtc tcttacagat aaaacaacag aaccagtgcc agaaagcagc cttcccttac     840
atgggcactt ctgccaagca tatgagttca ttgccttgaa gatcaaagtc aaagagaaat     900
ggagagggtg ttgaaatgat cagcgaaaat taaatgtaaa atatattctt attggaagtc     960
tgatgctcta ttatcaataa aggacacata gcaaagataa aaaaaaaaa aaaaaaaa      1019
```

<210> SEQ ID NO 4
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Ala Ser Ser Ser Asp Tyr Gly Gln Thr Ser Lys Met Ser
 1               5                  10                  15

Pro Arg Val Pro Gln Gln Asp Trp Leu Ser Gln Pro Pro Ala Arg Val
                20                  25                  30

Thr Ile Lys Met Glu Cys Asn Pro Ser Gln Val Asn Gly Ser Arg Asn
            35                  40                  45

Ser Pro Asp Glu Cys Ser Val Ala Lys Gly Gly Lys Met Val Gly Ser
        50                  55                  60

Pro Asp Thr Val Gly Met Asn Tyr Gly Ser Tyr Met Glu Glu Lys His
65                  70                  75                  80

Met Pro Pro Pro Asn Met Thr Thr Asn Glu Arg Arg Val Ile Val Pro
                85                  90                  95

Ala Asp Pro Thr Leu Trp Ser Thr Asp His Val Arg Gln Trp Leu Glu
            100                 105                 110

Trp Ala Val Lys Glu Tyr Gly Leu Pro Asp Val Asn Ile Leu Leu Phe
        115                 120                 125

Gln Asn Ile Asp Gly Lys Glu Leu Cys Lys Met Thr Lys Asp Asp Phe
    130                 135                 140

Gln Arg Leu Thr Pro Ser Tyr Asn Ala Asp Ile Leu Leu Ser His Leu
145                 150                 155                 160

His Tyr Leu Arg Glu Thr Pro Leu Pro His Leu Thr Ser Asp Asp Val
                165                 170                 175

```
Asp Lys Ala Leu Gln Asn Ser Pro Arg Leu Met His Ala Arg Asn Thr
            180                 185                 190

Gly Gly Ala Ala Phe Ile Phe Pro Asn Thr Ser Val Tyr Pro Glu Ala
        195                 200                 205

Thr Gln Arg Ile Thr Thr Arg Pro Val Ser Tyr Arg
    210                 215                 220

<210> SEQ ID NO 5
<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
acatcttgtt attccagaac atcgatggga aggaactgtg caagatgacc aaggacgact      60
tccagaggct cacccccagc tacaacgccg acatccttct ctcacatctc cactacctca    120
gagagagtaa gctccccctt cctccaagga tagatggctg tggctatggt tcttatgacc    180
cgagcttcag agggttcaac caggtgtgtc gacagcatcc tcctgccctc gcccagttcc    240
cactggggat ccgagggagc cacatgcttg gtcctgcga ccaagaagat ggaatgtcaa     300
aggggaaagg aagcgttaac tggtcacaca ttagttaagt ctccatgata ccccgaatca    360
aaatagaatc attaaggctt ctctttcgta ggaattaggg ggattattct ccctaaagct    420
acatgaagcc ccactttata ttctaacctg agcacagaac aagggaagtt ttcactttgt    480
atcatgtgat tcggcttaac ctgacagaaa gggatggcat gttggcatga atccagaatg    540
tttgctgcat gctttaattt ctacaacgtc cagcatggtg agaaggaagt agtgtgacag    600
acagtgaggt ggataaattc tcctccattg ctttgcctgg catcccaacc acttcttccc    660
tgaattaaag acgggccccc atgtaggttt taacatgcta acaagtagca ggttgctgga    720
aatagttata agcttcccat gatgttagtg tgggagtggg ggaacggttt ctttcttttct    780 ttttctttct tttttttttt ttttttt                                         807

<210> SEQ ID NO 6
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Thr Lys Asp Asp Phe Gln Arg Leu Thr Pro Ser Tyr Asn Ala Asp
1               5                   10                  15

Ile Leu Leu Ser His Leu His Tyr Leu Arg Glu Ser Lys Leu Pro Leu
            20                  25                  30

Pro Pro Arg Ile Asp Gly Cys Gly Tyr Gly Ser Tyr Asp Pro Ser Phe
        35                  40                  45

Arg Gly Phe Asn Gln Val Cys Arg Gln His Pro Pro Ala Leu Ala Gln
    50                  55                  60

Phe Pro Leu Gly Ile Arg Gly Ser His Met Leu Gly Ser Cys Asp Gln
65                  70                  75                  80

Glu Asp Gly Met Ser Lys Gly Lys Gly Ser Val Asn Trp Ser His Ile
                85                  90                  95

Ser
```

<210> SEQ ID NO 7
<211> LENGTH: 650
<212> TYPE: DNA
<213> ORGANISM: Homo sapiens

<400> SEQUENCE: 7

```
tctgtcgcca gtctggagtg cagtggcatg atctcagctc actgcaacct ccacctcccg    60
gattcaagca attttcctgc ctcagcctcc tgagtagctg ggactacagg catgcccagc   120
taattttgt atttttagta gagacggggt ttcaccatgt tggccaggat ggtctggatc   180
tcttgacctc atgatccgcc cacctcggca tcccaaagtg ttgggactac aggcatgagc   240
cacggcaccc cgcctgtatt tggcttttca cacttgtcct ttctccccca gtctcttccg   300
ccttgccctt ctttggttct ctctgtgtat tgtgagaagt cgatggagac atgctctttg   360
attgctgtta taatggaaga atatttcttc tcctccagga actctcctga tgaatgcagt   420
gtggccaaag gcgggaagat ggtgggcagc ccagacaccg ttgggatgaa ctacggcagc   480
tacatggagg agaagcacat gccaccccca aacatgacca cgaacgagcg cagagttatc   540
gtgccagcag tcaggtgcc cacagcttca ctgccctcgg cagatcgcaa cttccccaag   600
gctaggctga gcctcaggga gctcttctcc cccacctgtg gcattgatca              650
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
taggcgcgag ctaagcagga g                                              21
```

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ccaggatgcc ttctttgccc atc                                            23
```

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
accgttggga tgaactacgg ca                                             22
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaggatgcc ttctttgccc atc                                           23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccctcccaag agtctttgga tctc                                          24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cctggatttg caaggcggct act                                           23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctctccacgg ttaatgcatg ctag                                          24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagaaagcag ccttccctta                                               20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttgataatag agcatcagac ttcca                                         25

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

-continued ttcagaaaga cagatgggca aa                                          22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttcaaaagt cggcctattc ctaa                                        24

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaggcatcct ggatgcctgg ca                                          22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcacttctgc caagcatatg agt                                         23

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgctgatcat ttcaacaccc t                                           21

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgccttgaag atcaaagtca aagagaaatg ga                               32

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttcagatgat gttgataaag ccttaca                                     27

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tccaggctga tctcctggg                                                19

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgcatgcta gaaacacaga tttaccat                                      28

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggcgttgtag ctgggggtga g                                             21

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caatgaattc gtctgtactc catagcgtag ga                                 32

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgatgttgat aaagcctta                                                19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgacatcctt ctctcacat                                                19

<210> SEQ ID NO 30
<211> LENGTH: 2441
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
taggcgcgag ctaagcagga ggcggaggcg gaggcggagg gcgagggcg gggagcgccg      60
cctggagcgc ggcaggaagc cttatcagtt gtgagtgagg accagtcgtt gtttgagtgt     120
gcctacggaa cgccacacct ggctaagaca gagatgaccg cgtcctcctc cagcgactat     180
ggacagactt ccaagatgag cccacgcgtc cctcagcagg attggctgtc tcaaccccca     240
gccagggtca ccatcaaaat ggaatgtaac cctagccagg tgaatggctc aaggaactct     300
cctgatgaat gcagtgtggc caaaggcggg aagatggtgg gcagcccaga caccgttggg     360
atgaactacg cagctacat ggaggagaag cacatgccac ccccaaacat gaccacgaac       420
gagcgcagag ttatcgtgcc agcagatcct acgctatgga gtacagacca tgtgcggcag     480
tggctggagt gggcggtgaa agaatatggc cttccagacg tcaacatctt gttattccag     540
aacatcgatg ggaaggaact gtgcaagatg accaaggacg acttccagag gctcaccccc     600
agctacaacg ccgacatcct tctctcacat ctccactacc tcagagagac tcctcttcca     660
catttgactt cagatgatgt tgataaagcc ttacaaaact ctccacggtt aatgcatgct     720
agaaacacag gggtgcagc ttttattttc ccaaatactt cagtatatcc tgaagctacg       780
caaagaatta aactaggcc aggtacgaaa acaccctgt gtgatctctt cattgagaga        840
catcccagat gtcctgctga gatccgtgcc ctaagtcacg tgatacaaag agagctgatc     900
ccggagctga agccagtccc agacagtctt attctgcctc tgttgatttg agactaaat      960
ccactcaaac catttcattc aaagaccaca ctaaaggaat taagagcaga ttagcccttt    1020
aactagcttt tcagaaagac agatgggcaa agaaggcatc ctggatgcct ggcagttagg    1080
aataggccga cttttgaact aacagaagga tctgtccctc ctcggggaa gagcacaaaa     1140
caaggacact cccagattc acagtgaccg attatcagta tgtcacaaga agccagtctt     1200
gcagagcaga agcatgcaac cagtagtatt tacatctgaa tcttactgcc tgtcctccaa    1260
atgatttaat taggtaataa atttacatgc cattcatgca aaaataaaca tctatcaagt    1320
gcccattagt gccaagcgtg tgttagact ctgggaatat atagatgaac caggcttcag     1380
taagcttcct gtcttcagaa agtttacttc ttcattcagc ttggtttgtt catttgctga    1440
gtgcctcctc tgtgccagcc acggatggta tgatggtgaa caaaccgaaa tgttttgcct    1500
ccagttctag atgtttcagt agagtgacct agagccagag agacacatat gtacacataa    1560
atgtttcccc taatgtgata gattttatgg tagaggaacc acttctagca atacagggcg    1620
taggagcagg ggtggggagg aactcaatcc cccatgaaag gcataaagtt gctttccaga    1680
ggaatggcca catggcaaag gggaattaga tgtttgccag acgaataatg agcagggaga    1740
gagggcattt cccagaaggg tatagcttgc ctttagcatt tgtcctctcc ctggacttta    1800
catcagcccg ataagctagg tatcattgta ccagcctcac agctgatgac attgtgttca    1860
gggtggtggg atggtttctc catattcata catgcttcca gaattcatgt taaactctat    1920
cacatatccg gaatacacaa gtctcagttc gaactggttc aagatctagg cttggcaact    1980
actctttctt tctaatgaga aagactgggg gcccagggag ctaaagagaa tgaatgagga    2040
```

```
agcttctcag gctgttcaaa tactgacact gccctggtta ctgcctagtg acttcaggct    2100
ggcaattttc tcttctctaa cgtcagagaa aaagtttact gtcttgctcc tgggaagcat    2160
gatggaaagg cttagcagct aagggtact aagaggtagt aagtcatctc tgtcatgtaa     2220
aagatttcac aggccattga acatgggca agacccagtg cctagagtct gcaagattgg     2280
tcctaaagac atccaccacg tgtattgcga gtggaaaata gaaattcatg tttgactcaa    2340
gctttagaga ttttgtaatt ctgtgagcat ttaaaaaata tttccatata aactaaaaaa    2400
ataaaaacta tttccaaaaa aaaaaaaaaa aaaaactcga g                        2441
```

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gagcgccgcc tggagcgcgg cag                                              23

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttcagaaaga cagatgggc                                                   19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cacggatggt atgatggtg                                                   19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agcaatacag ggcgtaggag                                                  20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggcatttccc agaagggtat                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
catcagctgt gaggctggta                                           20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agtgacttca ggctggcaat                                           20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gctaagcctt tccatcatgc                                           20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acccagtgcc tagagtctgc                                           20

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aagcttgagt caaacatgaa tttct                                     25

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggaaccactt ctagcaata                                            19

```
<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgaataatga gcagggaga                                                       19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ccagggagct aaagagaat                                                       19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctgggaagca tgatggaaa                                                       19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gactcaagct ttagagatt                                                       19

<210> SEQ ID NO 46
<211> LENGTH: 1613
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gtacgaaaac acccctgtgt gatctcttca ttgagagaca tcccagatgt cctgctgaga          60
tccgtgccct aagtcacgtg atacaaagag agctgatccc ggagctgaag ccagtcccag         120
acagtcttat tctgcctctg ttgatttgga gactaaatcc actcaaacca tttcattcaa         180
agaccacact aaaggaatta agagcagatt agcccttaa ctagcttttc agaaagacag          240
atgggcaaag aaggcatcct ggatgcctgg cagttaggaa taggccgact tttgaactaa         300
cagaaggatc tgtccctcct cggggaaga gcacaaaaca aggacactcc ccagattcac          360
agtgaccgat tatcagtatg tcacaagaag ccagtcttgc agagcagaag catgcaacca         420
gtagtattta catctgaatc ttactgcctg tcctccaaat gatttaatta ggtaataaat         480
ttacatgcca ttcatgcaaa aataaacatc tatcaagtgc ccattagtgc caagcgtggt         540
```

```
gttagactct gggaatatat agatgaacca ggcttcagta agcttcctgt cttcagaaag    600
tttacttctt cattcagctt ggtttgttca tttgctgagt gcctcctctg tgccagccac    660
ggatggtatg atggtgaaca aaccgaaatg ttttgcctcc agttctagat gtttcagtag    720
agtgacctag agccagagag acacatatgt acacataaat gttttcccta atgtgataga    780
ttttatggta gaggaaccac ttctagcaat acagggcgta ggagcagggg tggggaggaa    840
ctcaatcccc catgaaaggc ataaagttgc tttccagagg aatggccaca tggcaaaggg    900
gaattagatg tttgccagac gaataatgag cagggagaga gggcatttcc cagaagggta    960
tagcttgcct ttagcatttg tcctctccct gggacttaca tcagcccgat aagctaggta   1020
tcattgtacc agcctcacag ctgatgacat tgtgttcagg gtggtgggat ggtttctcca   1080
tattcataca tgcttccaga attcatgtta aactctatca catatccgga atacacaagt   1140
ctcagttcga actggttcaa gatctaggct tggcaactac tctttctttc taatgagaaa   1200
gactgggggc ccagggagct aaagagaatg aatgaggaag cttctcaggc tgttcaaata   1260
ctgacactgc cctggttact gcctagtgac ttcaggctgg caattttctc ttctctaacg   1320
tcagagaaaa agtttactgt cttgctcctg ggaagcatga tggaaaggct tagcagctaa   1380
ggggtactaa gagtagtaa gtcatctctg tcatgtaaaa gatttcacag gccattgaaa   1440
catgggcaag acccagtgcc tagagtctgc aagattggtc ctaaagacat ccaccacgtg   1500
tattgcgagt ggaaaataga aattcatgtt tgactcaagc tttagagatt ttgtaattct   1560
gtgagcattt aaaaaatatt tccatataaa ctaaaaaaat aaaaactatt tcc          1613
```

<210> SEQ ID NO 47
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Thr Lys Thr Pro Leu Cys Asp Leu Phe Ile Glu Arg His Pro Arg
 1               5                  10                  15

Cys Pro Ala Glu Ile Arg Ala Leu Ser His Val Ile Gln Arg Glu Leu
            20                  25                  30

Ile Pro Glu Leu Lys Pro Val Pro Asp Ser Leu Ile Leu Pro Leu Leu
        35                  40                  45

Ile Trp Arg Leu Asn Pro Leu Lys Pro Phe His Ser Lys Thr Thr Leu
    50                  55                  60

Lys Glu Leu Arg Ala Asp
 65                  70

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aaaaataaac a                                                           11

<210> SEQ ID NO 49
<211> LENGTH: 11

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aaaaaaaaaa a                                                               11

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggctttgatg aaagctctaa acaac                                                25

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcaaaagtgc ctcaagagga                                                      20

<210> SEQ ID NO 52
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Phe His Gly Ile Ala Gln Ala Leu Gln Pro His Pro Pro Glu Ser
 1               5                  10                  15

Ser Leu Tyr Lys Tyr Pro Ser Asp Leu Pro Tyr Met Gly Ser Tyr His
            20                  25                  30

Ala His Pro Gln Lys Met Asn Phe Val Ala Pro His Pro Pro Ala Leu
        35                  40                  45

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tggagatgtg agagaaggat gtcg                                                 24

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
```
gagccacatc gcctcagaca cc                                              22

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gttctcagct tgacggtgcc                                                 20

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gccccttgca tcctgagctc c                                               21

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggtcggacat tcctgcttta                                                 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
acccaacacc acgtcctaac                                                 20

<210> SEQ ID NO 59
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agagcacaga aaggctgccc tggaagtggc tgggcatcct gtcagct                   47

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

```
tgtgggactt ctctgctgaa                                                  20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
caacgttcaa ggggaagaaa                                                  20

<210> SEQ ID NO 62
<211> LENGTH: 1460
<212> TYPE: DNA
<213> ORGANISM: Homo sapiens

<400> SEQUENCE: 62
cccccgaggg acatgagaga agaggagcgg cgctcaggtt attccaggat ctttggagac      60
ccgaggaaag ccgtgttgac caaaagcaag acaaatgact cacagagaaa aaagatggca    120
gaaccaaggg caactaaagc cgtcaggttc tgaacagctg gtagatgggc tggcttactg    180
aaggacatga ttcagactgt cccggaccca gcagctcata tcaaggaagc cttatcagtt    240
gtgagtgagg accagtcgtt gtttgagtgt gcctacggaa cgccacacct ggctaagaca    300
gagatgaccg cgtcctcctc cagcgactat ggacagactt ccaagatgag cccacgcgtc    360
cctcagcagg attggctgtc tcaaccccca gccagggtca ccatcaaaat ggaatgtaac    420
cctagccagg tgaatggctc aaggaactct cctgatgaat gcagtgtggc caaaggcggg    480
aagatggtgg gcagcccaga caccgttggg atgaactacg gcagctacat ggaggagaag    540
cacatgccac ccccaaacat gaccacgaac gagcgcagag ttatcgtgcc agcagatcct    600
acgctatgga gtacagacca tgtgcggcag tggctggagt gggcggtgaa agaatatggc    660
cttccagacg tcaacatctt gttattccag aacatcgatg ggaaggaact gtgcaagatg    720
accaaggacg acttccagag gctcacccc agctacaacg ccgacatcct tctctcacat    780
ctccactacc tcagagagac tcctcttcca catttgactt cagatgatgt tgataaagcc    840
ttacaaaact ctccacggtt aatgcatgct agaaacacag ggggtgcagc ttttattttc    900
ccaaatactt cagtatatcc tgaagctacg caaagaatta caactaggcc aggtacgaaa    960 acaccctgt gtgatctctt cattgagaga catcccagat gtcctgctga gatccgtgcc   1020
ctaagtcacg tgatacaaag agagctgatc ccggagctga agccagtccc agacagtctt   1080
attctgcctc tgttgatttg gagactaaat ccactcaaac catttcattc aaagaccaca   1140
ctaaaggaat taagagcaga ttagccctt aactagcttt tcagaaagac agatgggcaa   1200
agaaggcatc ctggatgcct ggcagttagg aataggccga cttttgaact aacagaagga   1260
tctgtccctc ctcggggaa gagcacaaaa caaggacact ccccagattc acagtgaccg   1320
attatcagta tgtcacaaga agccagtctt gcagagcaga agcatgcaac cagtagtatt   1380
tacatctgaa tcttactgcc tgtcctccaa atgatttaat taggtaataa atttacatgc   1440
cattcatgca aaaaaaaaaa                                               1460
```